(12) United States Patent
Djurovich et al.

(10) Patent No.: US 11,920,070 B2
(45) Date of Patent: Mar. 5, 2024

(54) LUMINESCENT JANUS-TYPE, TWO-COORDINATED METAL COMPLEXES

(71) Applicant: The University of Southern California, Los Angeles, CA (US)

(72) Inventors: Peter I. Djurovich, Long Beach, CA (US); Mark E. Thompson, Anaheim Hills, CA (US); Narcisse Ukwitegetse, Los Angeles, CA (US); Tian-Yi Li, Los Angeles, CA (US); Rasha Hamze, Los Angeles, CA (US)

(73) Assignee: The University of Southern California

( * ) Notice: Subject to any disclaimer, the term of this patent is extended or adjusted under 35 U.S.C. 154(b) by 577 days.

(21) Appl. No.: 16/901,087

(22) Filed: Jun. 15, 2020

(65) Prior Publication Data

US 2021/0009895 A1    Jan. 14, 2021

Related U.S. Application Data

(60) Provisional application No. 62/873,310, filed on Jul. 12, 2019, provisional application No. 62/957,938, filed on Jan. 7, 2020.

(51) Int. Cl.
| | | |
|---|---|---|
| C09K 11/06 | (2006.01) | |
| C07D 233/06 | (2006.01) | |
| C07D 239/10 | (2006.01) | |
| H10K 85/30 | (2023.01) | |
| H10K 50/11 | (2023.01) | |
| H10K 101/10 | (2023.01) | |

(52) U.S. Cl.
CPC ............ *C09K 11/06* (2013.01); *C07D 233/06* (2013.01); *C07D 239/10* (2013.01); *H10K 85/361* (2023.02); *H10K 85/371* (2023.02); *C09K 2211/188* (2013.01); *H10K 50/11* (2023.02); *H10K 2101/10* (2023.02)

(58) Field of Classification Search
None
See application file for complete search history.

(56) References Cited

U.S. PATENT DOCUMENTS

| | | |
|---|---|---|
| 4,769,292 A | 9/1988 | Tang |
| 5,061,569 A | 10/1991 | Vanslyke |
| 5,247,190 A | 9/1993 | Friend |

(Continued)

FOREIGN PATENT DOCUMENTS

| | | | |
|---|---|---|---|
| CN | 107652313 A | * | 2/2018 |
| EP | 0650955 | | 5/1995 |

(Continued)

OTHER PUBLICATIONS

Machine English translation of Pu et al. (CN-107652313-A). Jun. 28, 2023.*

(Continued)

*Primary Examiner* — Jay Yang
*Assistant Examiner* — J. L. Yang
(74) *Attorney, Agent, or Firm* — Riverside Law LLP

(57) ABSTRACT

The co-linear or near co-linear structure of bimetallic Janus-type two-coordinated metal complexes may allow for a large transition dipole moment that can enhance the radiative lifetime. The symmetric nature of the bimetallic Janus complexes diminishes or eliminates the polar nature of the monometallic carbene-metal-amide/arene complexes.

8 Claims, 14 Drawing Sheets

(56) References Cited

U.S. PATENT DOCUMENTS

| | | |
|---|---|---|
| 5,703,436 A | 12/1997 | Forrest |
| 5,707,745 A | 1/1998 | Forrest |
| 5,834,893 A | 11/1998 | Bulovic |
| 5,844,363 A | 12/1998 | Gu |
| 6,013,982 A | 1/2000 | Thompson |
| 6,087,196 A | 7/2000 | Sturm |
| 6,091,195 A | 7/2000 | Forrest |
| 6,097,147 A | 8/2000 | Baldo |
| 6,294,398 B1 | 9/2001 | Kim |
| 6,303,238 B1 | 10/2001 | Thompson |
| 6,337,102 B1 | 1/2002 | Forrest |
| 6,468,819 B1 | 10/2002 | Kim |
| 6,528,187 B1 | 3/2003 | Okada |
| 6,687,266 B1 | 2/2004 | Ma |
| 6,835,469 B2 | 12/2004 | Kwong |
| 6,921,915 B2 | 7/2005 | Takiguchi |
| 7,087,321 B2 | 8/2006 | Kwong |
| 7,090,928 B2 | 8/2006 | Thompson |
| 7,154,114 B2 | 12/2006 | Brooks |
| 7,250,226 B2 | 7/2007 | Tokito |
| 7,279,704 B2 | 10/2007 | Walters |
| 7,332,232 B2 | 2/2008 | Ma |
| 7,338,722 B2 | 3/2008 | Thompson |
| 7,393,599 B2 | 7/2008 | Thompson |
| 7,396,598 B2 | 7/2008 | Takeuchi |
| 7,431,968 B1 | 10/2008 | Shtein |
| 7,445,855 B2 | 11/2008 | Mackenzie |
| 7,534,505 B2 | 5/2009 | Lin |
| 7,968,146 B2 | 6/2011 | Wagner |
| 8,409,729 B2 | 4/2013 | Zeng |
| 9,773,986 B2 | 9/2017 | Thompson |
| 2002/0034656 A1 | 3/2002 | Thompson |
| 2002/0134984 A1 | 9/2002 | Igarashi |
| 2002/0158242 A1 | 10/2002 | Son |
| 2003/0129449 A1* | 7/2003 | Parton et al. ............. 428/690 |
| 2003/0138657 A1 | 7/2003 | Li |
| 2003/0152802 A1 | 8/2003 | Tsuboyama |
| 2003/0162053 A1 | 8/2003 | Marks |
| 2003/0175553 A1 | 9/2003 | Thompson |
| 2003/0230980 A1 | 12/2003 | Forrest |
| 2004/0036077 A1 | 2/2004 | Ise |
| 2004/0137267 A1 | 7/2004 | Igarashi |
| 2004/0137268 A1 | 7/2004 | Igarashi |
| 2004/0174116 A1 | 9/2004 | Lu |
| 2005/0025993 A1 | 2/2005 | Thompson |
| 2005/0112407 A1 | 5/2005 | Ogasawara |
| 2005/0238919 A1 | 10/2005 | Ogasawara |
| 2005/0244673 A1 | 11/2005 | Satoh |
| 2005/0260441 A1 | 11/2005 | Thompson |
| 2005/0260449 A1 | 11/2005 | Walters |
| 2006/0008670 A1 | 1/2006 | Lin |
| 2006/0202194 A1 | 9/2006 | Jeong |
| 2006/0240279 A1 | 10/2006 | Adamovich |
| 2006/0251923 A1 | 11/2006 | Lin |
| 2006/0263635 A1 | 11/2006 | Ise |
| 2006/0280965 A1 | 12/2006 | Kwong |
| 2007/0190359 A1 | 8/2007 | Knowles |
| 2007/0278938 A1 | 12/2007 | Yabunouchi |
| 2008/0015355 A1 | 1/2008 | Schafer |
| 2008/0018221 A1 | 1/2008 | Egen |
| 2008/0106190 A1 | 5/2008 | Yabunouchi |
| 2008/0124572 A1 | 5/2008 | Mizuki |
| 2008/0220265 A1 | 9/2008 | Xia |
| 2008/0297033 A1 | 12/2008 | Knowles |
| 2009/0008605 A1 | 1/2009 | Kawamura |
| 2009/0009065 A1 | 1/2009 | Nishimura |
| 2009/0017330 A1 | 1/2009 | Iwakuma |
| 2009/0030202 A1 | 1/2009 | Iwakuma |
| 2009/0039776 A1 | 2/2009 | Yamada |
| 2009/0045730 A1 | 2/2009 | Nishimura |
| 2009/0045731 A1 | 2/2009 | Nishimura |
| 2009/0101870 A1 | 4/2009 | Prakash |
| 2009/0108737 A1 | 4/2009 | Kwong |
| 2009/0115316 A1 | 5/2009 | Zheng |
| 2009/0165846 A1 | 7/2009 | Johannes |
| 2009/0167162 A1 | 7/2009 | Lin |
| 2009/0179554 A1 | 7/2009 | Kuma |
| 2013/0026452 A1 | 1/2013 | Kottas |
| 2013/0119354 A1 | 5/2013 | Ma |
| 2014/0054564 A1 | 2/2014 | Kim |
| 2015/0318487 A1 | 11/2015 | Ito |

FOREIGN PATENT DOCUMENTS

| | | |
|---|---|---|
| EP | 1238981 | 9/2002 |
| EP | 1725079 | 11/2006 |
| EP | 2034538 | 3/2009 |
| EP | 2551932 | 1/2013 |
| EP | 2977378 | 1/2016 |
| JP | 200511610 | 1/2005 |
| JP | 2007123392 | 5/2007 |
| JP | 2007254297 | 10/2007 |
| JP | 2008074939 | 4/2008 |
| JP | 2010135467 | 6/2010 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2004111066 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008044723 | 4/2008 |
| WO | 2008056746 | 5/2008 |
| WO | 2008057394 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2010011390 | 1/2010 |
| WO | 2010111175 | 9/2010 |
| WO | 2010126234 | 11/2010 |

OTHER PUBLICATIONS

Gao et al. (Organometallics 2009, 28, 5669-5681).*

Khramov, D. M.; Boydston, A. J.; Bielawski, C. W., Synthesis and study of Janus bis(carbene)s and their transition-metal complexes. Angewandte Chemie, International Edition in English 2006, 45 (37), 6186-6189 DOI: 10.1002/anie.200601583.

Guerret, O.; Solé, S.; Gornitzka, H.; Teichert, M.; Trinquier, G.; Bertrand, G., 1,2,4-Triazole-3,5-diylidene: A Building Block for Organometallic Polymer Synthesis. Journal of the American Chemical Society 1997, 119 (28), 6668-6669 DOI: 10.1021/ja964191a.

(56) References Cited

OTHER PUBLICATIONS

Hudnall, T. W .; Tennyson, A. G.; Bielawski, C. W., A Seven-Membered N,N'-Diamidocarbene. Organometallics 2010, 29 (20), 4569-4578 DOI: 10.1021/om1007665.

Schinabeck, A.; Chen, J.; Kang, L.; Teng, T.; Homeier, H. H. H.; Suleymanova, A. F.; Shafikov, M. Z.; Yu, R.; Lu, C.- Z.; Yersin, H., Symmetry-Based Design Strategy for Unprecedentedly Fast Decaying Thermally Activated Delayed Fluorescence (TADF). Application to Dinuclear Cu(I) Compounds. Chemistry of Materials 2019, DOI: 10.1021/acs.chemmater.9b00671, 13 pages.

Ivanov, M. V., Wadumethrige, S. H., Wang, D., & Rathore, R. (2017). Through-Space or Through- Bond? The Important Role of Cofaciality in Orbital Reordering and Its Implications for Hole (De)stabilization in Polychromophoric Assemblies. The Journal of Physical Chemistry C, 121(29), 15639-15643.

Prades, A.; Peris, E.; Alcarazo, M., Pyracenebis(imidazolylidene): A New Janus-Type Biscarbene and Its Coordination to Rhodium and Iridium. Organometallics 2012, 31 (12), 4623-4626 DOI: 10.1021/om3003834.

Gonell, S.; Poyatos, M.; Peris, E., Pyrene-Based Bisazolium Salts: From Luminescence Properties to Janus-Type Bis-N-Heterocyclic Carbenes. Chemistry-a European Journal 2014, 20 (31), 9716-9724 DOI: 10.1002/chem.201304952.

Ibanez, S.; Poyatos, M.; Peris, E., A D-3h-symmetry hexaazatriphenylene-tris-N-heterocyclic carbene ligand and its coordination to iridium and gold: preliminary catalytic studies. Chemical Communications 2017, 53 (26), 3733-3736 DOI: 10.1039/c7cc00525c.

Wong, Wai-Yeung, "Multifunctional Iridium Complexes Based on Carbazole Modules as Highly Efficient Electrophosphors," Angew. Chem. Int. Ed., 45:7800-7803 (2006).

Ma, Yuguang et al., "Triplet Luminescent Dinuclear-Gold(I) Complex-Based Light-Emitting Diodes with Low Turn-On voltage," Appl. Phys. Lett., 74(10): 1361-1363 (1999).

Mi, Bao-Xiu et al., "Thermally Stable Hole-Transporting Material for Organic Light-Emitting Diode: an Isoindole Derivative," Chem. Mater., 15(16):3148-3151 (2003).

Okumoto, Kenji et al., "Green Fluorescent Organic Light-Emitting Device with External Quantum Efficiency of Nearly 10%," Appl. Phys. Lett., 89:063504-1-063504-3 (2006).

Paulose, Betty Marie Jennifer S, et al., "First Examples of Alkenyl Pyridines as Organic Ligands for Phosphorescent Iridium Complexes," Adv. Mater., 16(22):2003-2007 (2004).

Tang, C.W. and VanSlyke, S.A., "Organic Electroluminescent Diodes," Appl. Phys. Lett., 51(12):913-915 (1987).

T. Ostergard et al., "Langmuir-Blodgett Light-Emitting Diodes of Poly(3-Hexylthiophene): Electro-Optical Characteristics Related to Structure," Synthetic Metals, 87:171-177 (1997).

Tung, Yung-Liang et al., "Organic Light-Emitting Diodes Based on Charge-Neutral Ru II PHosphorescent Emitters," Adv. Mater., 17(8):1059-1064 (2005).

Van Slyke, S. A. et al., "Organic Electroluminescent Devices with Improved Stability," Appl. Phys. Lett, 69(15 ):2160-2162 (1996).

Wong, Keith Man-Chung et al., "A Novel Class of Phosphorescent Gold(III) Alkynyl-Based Organic Light-Emitting Devices with Tunable Colour," Chem. Commun., 2906-2908 (2005).

Adachi, Chihaya et al., "Organic Electroluminescent Device Having a Hole Conductor as an Emitting Layer," Appl. Phys. Lett., 55(15):1489-1491 (1989).

Baldo et al., "Highly Efficient Phosphorescent Emission from Organic Electroluminescent Devices," Nature, vol. 395,151-154, (1998).

Gao, Zhiqiang et al., "Bright-Blue Electroluminescence From a Silyl-Substituted ter-(phenylenevinylene) derivative," Appl. Phys. Lett., 74(6):865-867 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Wang, Y. et al., "Highly Efficient Electroluminescent Materials Based on Fluorinated Organometallic Iridium Compounds," Appl. Phys. Lett., 79(4):449-451 (2001).

Kwong, Raymond C. et al., "High Operational Stability of Electrophosphorescent Devices," Appl. Phys. Lett., 81(1):162-164 (2002).

Holmes, R.J. et al., "Blue Organic Electrophosphorescence Using Exothermic Host-Guest Energy Transfer," Appl. Phys. Lett., 82(15):2422-2424 (2003).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

Adachi, Chihaya et al., "High-Efficiency Red Electrophosphorescence Devices," Appl. Phys. Lett., 78(11):1622-1624 (2001).

Hamada, Yuji et al., "High Luminance in Organic Electroluminescent Devices with Bis(10-hydroxybenzo[h]quinolinato)beryllium as an Emitter," Chem. Lett., 905-906 (1993).

Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4):592-593 (2005).

Baldo et al., "Very high-efficiency green organic light-emitting devices based on electrophosphorescence," Appl. Phys. Lett., vol. 75, No. 3, 4-6 (1999).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Niu, Yu-Hua et al., "Highly Efficient Electrophosphorescent Devices with Saturated Red Emission from a Neutral Osmium Complex," Chem. Mater., 17(13):3532-3536 (2005).

Lo, Shih-Chun et al., "Blue Phosphorescence from Iridium(III) Complexes at Room Temperature," Chem. Mater., 18(21):5119-5129 (2006).

Takizawa, Shin-ya et al., "Phosphorescent Iridium Complexes Based on 2-Phenylimidazo[1,2-a]pyridine Ligands: Tuning of Emission Color toward the Blue Region and Application to Polymer Light-Emitting Devices," Inorg. Chem., 46(10):4308-4319 (2007).

Lamansky, Sergey et al., "Synthesis and Characterization of Phosphorescent Cyclometalated Iridium Complexes," Inorg. Chem., 40(7):1704-1711 (2001).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Noda, Tetsuya and Shirota, Yasuhiko, "5,6-Bis(dinnesitylboryl)-2,2'-bithiophene and 5,5Δ- Bis(dimesitylbory1)-2,2':5',2"-terthiophene as a Novel Family of Electron-Transporting Amorphous Molecular Materials," J. Am. Chem. Soc., 120 (37):9714-9715 (1998).

Sakamoto, Youichi et al., "Synthesis, Characterization, and Electron-Transport Property of Perfluorinated Phenylene Dendrimers," J. Am. Chem. Soc., 122(8): 1832-1833 (2000).

Adachi, Chihaya et al., "Nearly 100% Internal Phosphorescence Efficiency in an Organic Light Emitting Device," J. Appl. Phys., 90(10):5048-5051 (2001).

Shirota, Yasuhiko et al., "Starburst Molecules Based on p-Electron Systems as Materials for Organic Electroluminescent Devices," Journal of Luminescence, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kido, Junji et al.,"1,2,4-Triazole Derivative as an Electron Transport Layer in Organic Electroluminescent Devices," Jpn. J. Appl. Phys., 32:L917-L920 (1993).

(56) References Cited

OTHER PUBLICATIONS

Guo, Tzung-Fang et al., "Highly Efficient Electrophosphorescent Polymer Light-Emitting Devices," Organic Electronics, 1:15-20 (2000).

Palilis, Leonidas C., "High Efficiency Molecular Organic Light-Emitting Diodes Based On Silole Derivatives and Their Exciplexes," Organic Electronics, 4:113-121 (2003).

Ikeda, Hisao et al., "P-185: Low-Drive-Voltage OLEDs with a Buffer Layer Having Molybdenum Oxide," SID Symposium Digest, 37:923-926 (2006).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Salbeck, J. et al., "Low Molecular Organic Glasses for Blue Electroluminescence," Synthetic Metals, 91:209-215 (1997).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

* cited by examiner

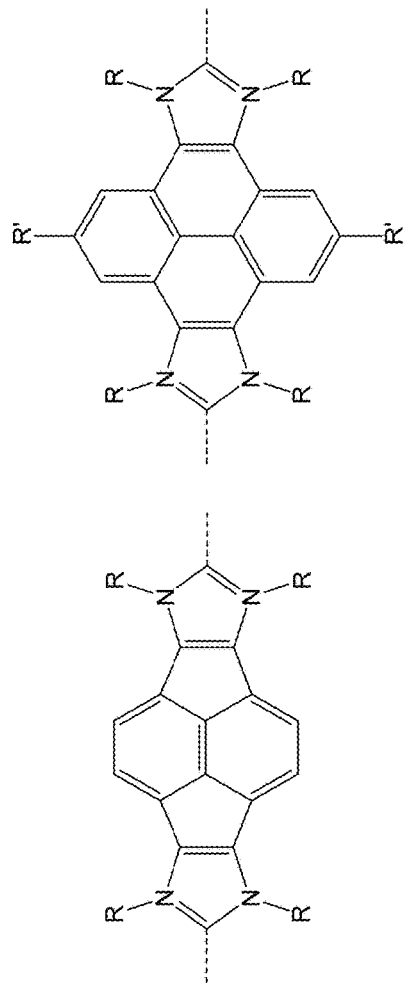
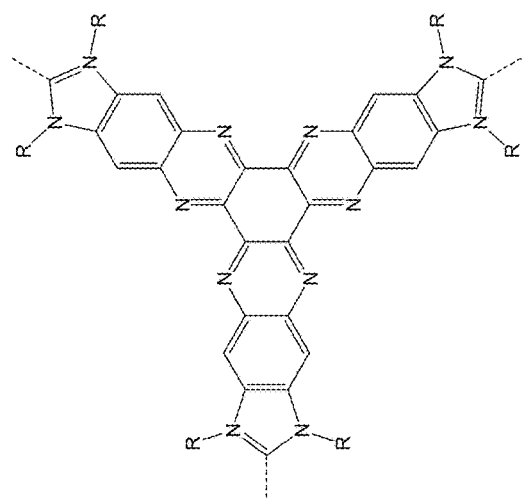
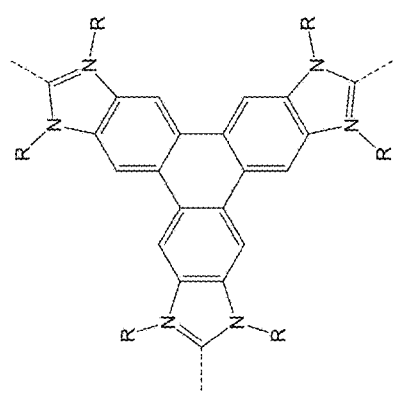
Figure 7
Figure 8

LUMINESCENT JANUS-TYPE, TWO-COORDINATED METAL COMPLEXES

CROSS-REFERENCE TO RELATED APPLICATIONS

The present application claims priority to U.S. Provisional Application No. 62/873,310, filed Jul. 12, 2019, and to U.S. Provisional Application No. 62/957,938, filed Jan. 7, 2020, both of which are incorporated by reference herein in their entireties.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

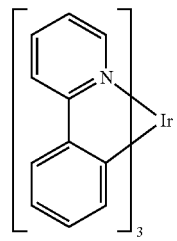

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

The present invention relates to a compound of Formula I, Formula IIa, or Formula IIb:

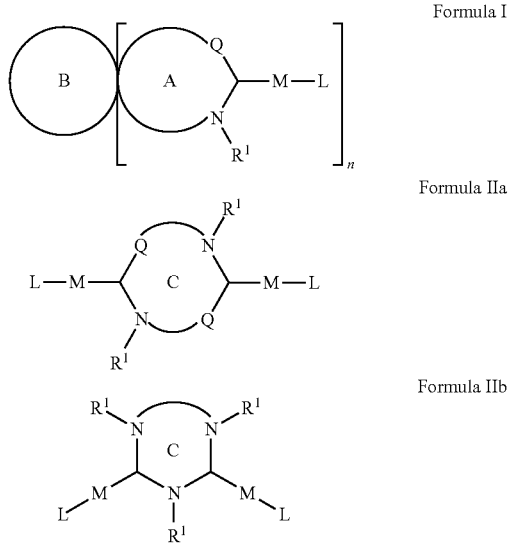

wherein each ring A is independently a 5, 6, or 7-membered N-heterocyclic carbene which is condensed with ring B, wherein each ring A may be the same or different;

n is 1, 2, or 3;

ring B is a single or fused saturated or unsaturated carbocyclic or heterocyclic ring which is fused to the n adjacent rings A at arbitrary positions;

ring C in Formula IIa is a 6, 7, or 8-membered N-heterocyclic carbene;

ring C in Formula IIb is a 5, 6, or 7-membered N-heterocyclic carbene;

Q is $NR^1$, O, or S;

each occurrence of $R^1$ is independently alkyl or aryl, wherein $R^1$ may be further substituted with a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

M is Au, Ag, or Cu; and

L is a monoanionic ligand.

The present invention also relates to a compound of Formula III or Formula IV

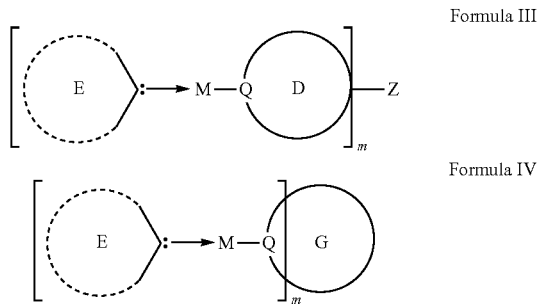

wherein E is a carbene coordinated to metal M;

each E can be the same or different;

each ring D is independently a single or fused carbocyclic ring or heterocyclic ring, which may be saturated or unsaturated, which is bound covalently bound to Z, wherein each ring D may be the same or different, and wherein each ring D is independently substituted with R;

Z is a linking group selected from the group consisting of a single bond, aryl, heteroaryl, alkyl, O, S, NR, and combinations thereof;

m is 2, 3, or 4;

G is a single or fused carbocyclic ring or heterocyclic ring, which may be saturated or unsaturated; which comprises m atoms Q; and which may be optionally substituted with one or more R.

each occurrence of R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

each occurrence of Q is independently C or N; and

M is Au, Ag, or Cu.

The invention also relates to an organic light emitting device (OLED) comprising: an anode; a cathode; and an organic layer, disposed between the anode and the cathode, comprising a compound of the present invention.

The invention also relates to a formulation comprising a compound of the present invention.

BRIEF DESCRIPTION OF THE DRAWINGS

FIG. 7 depicts exemplary bridging structures for bis-carbenes. R, R'=alkyl, aryl, alkoxy, etc.

FIG. 8 depicts exemplary bridging structures for tris-carbenes. R, R'=alkyl, aryl, alkoxy, etc.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
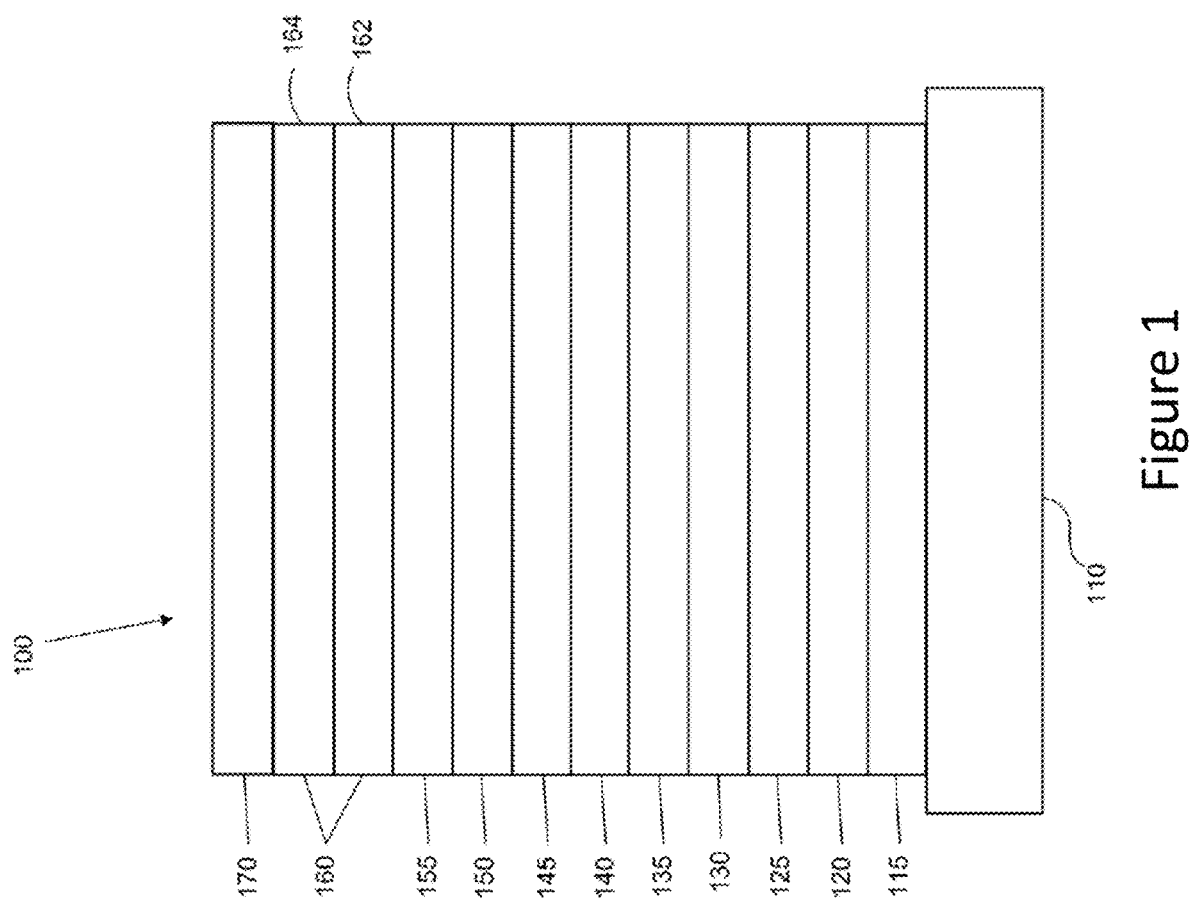
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
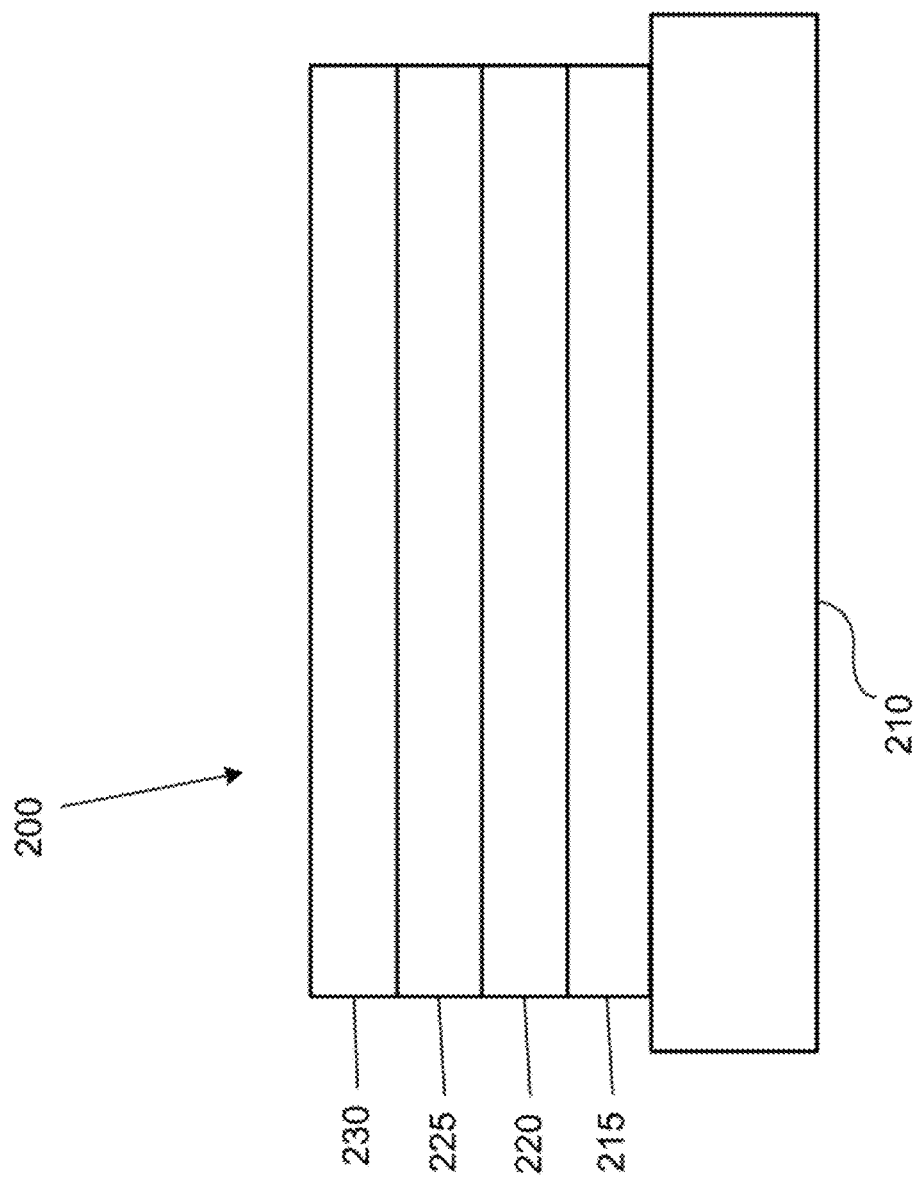
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," and "halide" are used interchangeably and refer to fluorine, chlorine, bromine, and iodine.

The term "acyl" refers to a substituted carbonyl radical (C(O)—Rs).

The term "ester" refers to a substituted oxycarbonyl (—O—C(O)—Rs or —C(O)—O—Rs) radical.

The term "ether" refers to an —ORs radical.

The terms "sulfanyl" or "thio-ether" are used interchangeably and refer to a —SRs radical.

The term "sulfinyl" refers to a —S(O)—Rs radical.

The term "sulfonyl" refers to a —SO2—Rs radical.

The term "phosphino" refers to a —P(Rs)3 radical, wherein each Rs can be same or different.

The term "silyl" refers to a —Si(Rs)3 radical, wherein each Rs can be same or different.

In each of the above, Rs can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred Rs is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo [3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when R1 represents mono-substitution, then one R1 must be other than H (i.e., a substitution). Similarly, when R1 represents di-substitution, then two of R1 must be other than H. Similarly, when R1 represents no substitution, R1, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., Tetrahedron 2015, 71, 1425-30 and Atzrodt et al., Angew. Chem. Int. Ed. (Reviews) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

In one aspect, the present invention relates to compounds of Formula I, Formula IIa, or Formula IIb:

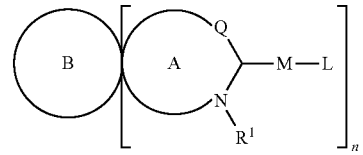

Formula I

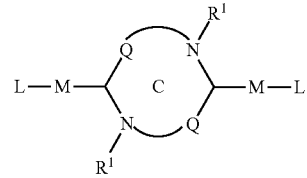

Formula IIa

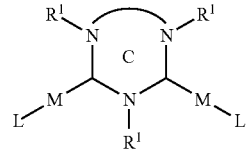

Formula IIb wherein each ring A is independently a 5, 6, or 7-membered N-heterocyclic carbene which is condensed with ring B, wherein each ring A may be the same or different;

n is 1, 2, or 3;

ring B is a single or fused saturated or unsaturated carbocyclic or heterocyclic ring which is fused to the n adjacent rings A at arbitrary positions;

ring C in Formula IIa is a 6, 7, or 8-membered N-heterocyclic carbene;

ring C in Formula IIb is a 5, 6, or 7-membered N-heterocyclic carbene;

Q is $NR^1$, O, or S;

each occurrence of $R^1$ is independently alkyl or aryl, wherein $R^1$ may be further substituted with a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

M is Au, Ag, or Cu; and

L is a monoanionic ligand.

In one embodiment, the compound of Formula I is a compound of Formula Ia or Formula Ib.

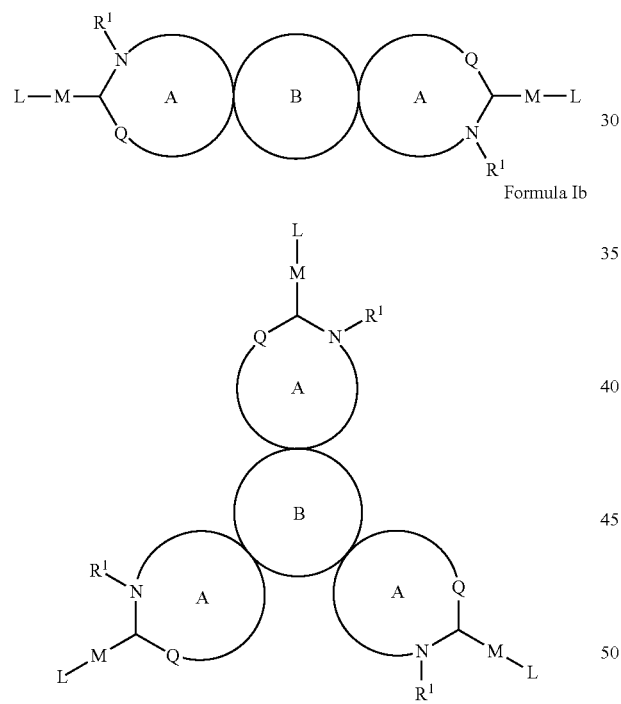

Formula Ia

Formula Ib

In one embodiment, ring B is selected from the group consisting of

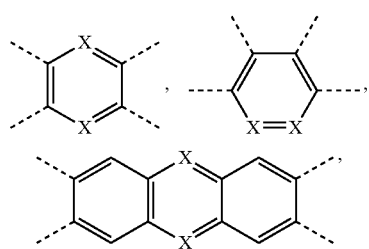

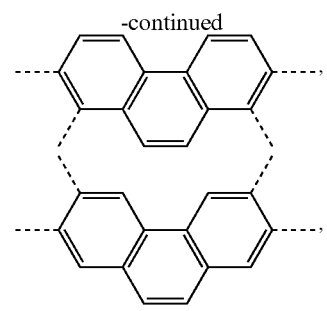

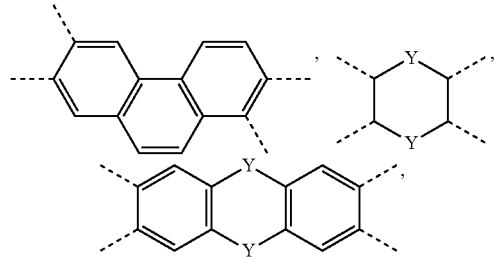

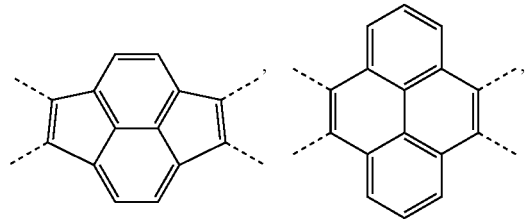

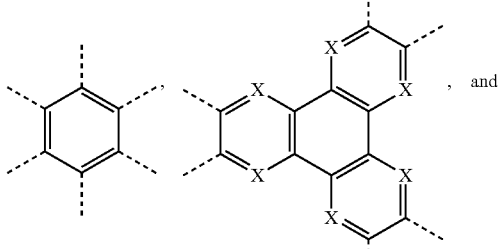

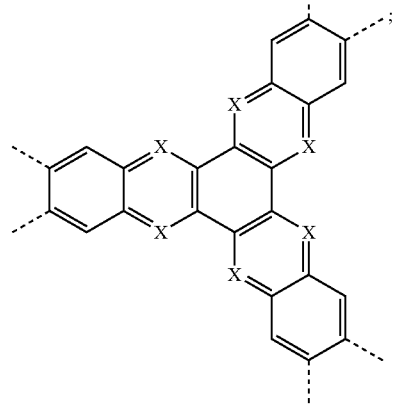

wherein each occurrence of X is independently N or $CR^2$;

each occurrence of Y is selected from the group consisting of a single bond, O, S, Se, $C(R^3)_2$, $Si(R^3)_2$, and $NR^3$;

each occurrence of $R^2$ and $R^3$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

ring B may be further substituted; and dashed lines indicate the positions of the ring fusion to ring A.

In one embodiment, ring A selected from the group consisting of

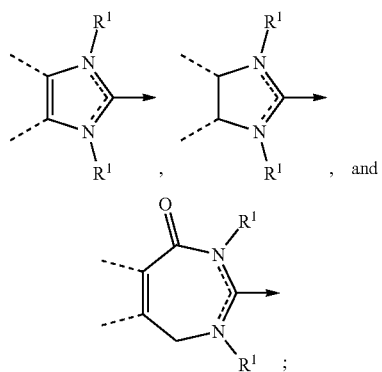

wherein dashed lines indicate the positions of the ring fusion to ring B; and arrows indicate the coordination site to M.

In one embodiment, the compound is selected from the group consisting of

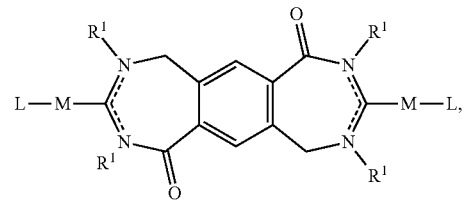

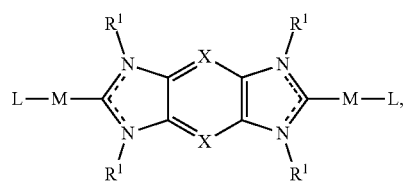

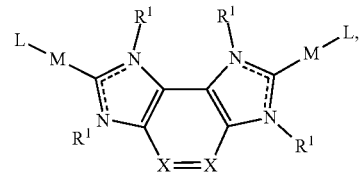

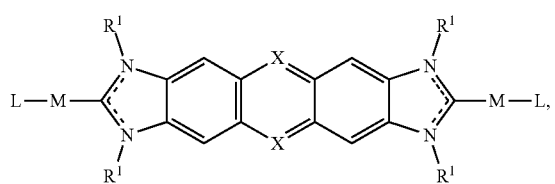

-continued

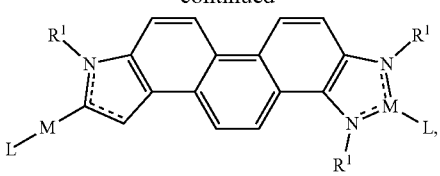

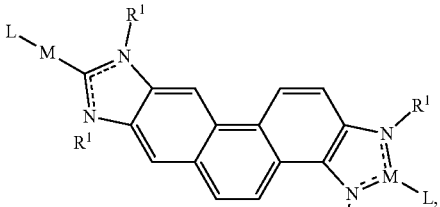

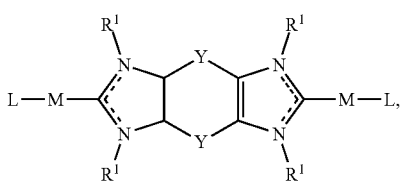

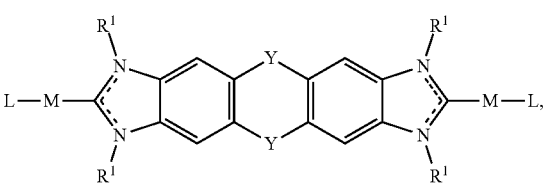

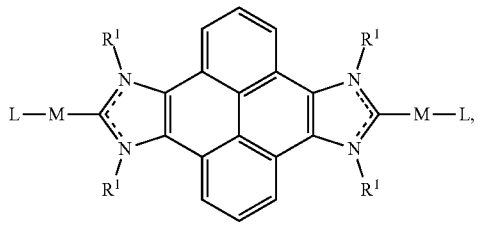

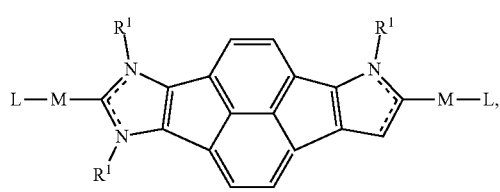

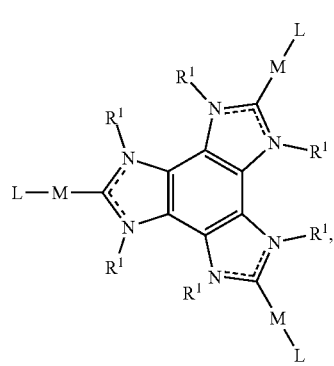

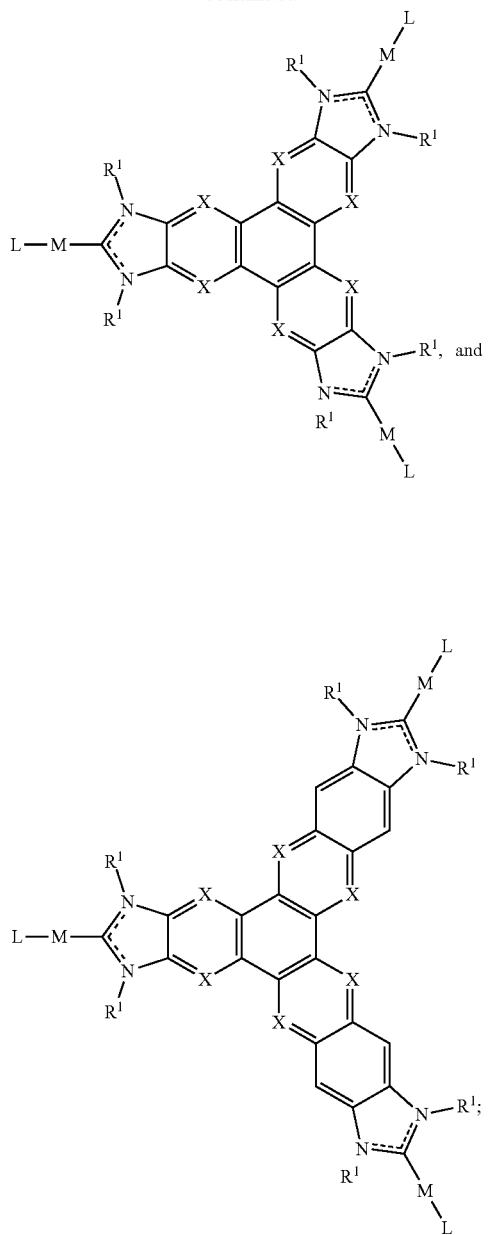

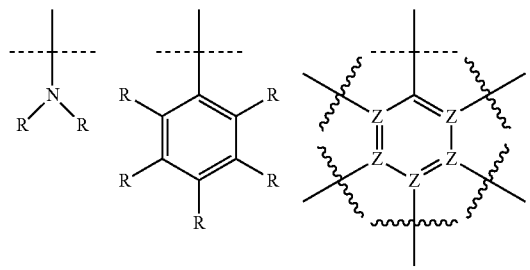

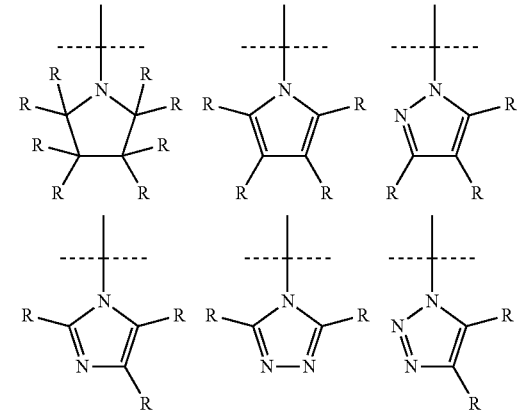

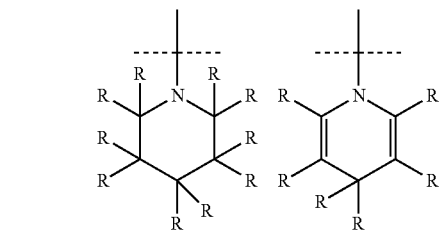

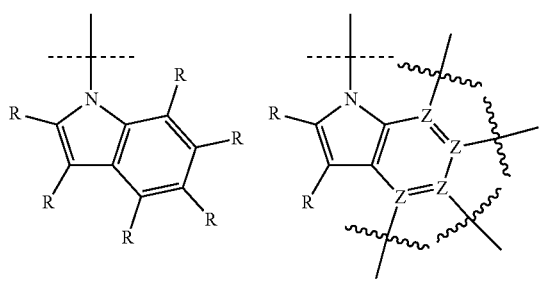

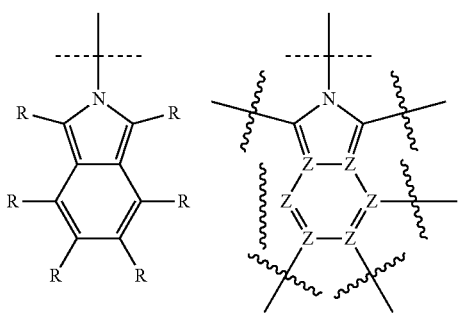

wherein each occurrence of X is independently N or CR²;

each occurrence of Y is selected from the group consisting of a single bond, O, S, Se, C(R³)₂, Si(R³)₂, and NR³;

each occurrence of R² and R³ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; ring B may be further substituted.

In one embodiment, L is a monoanionic hydrocarbon, amide, alkoxide, sulfide, or phosphide, which may be optionally further substituted. In one embodiment, L forms a 3-coordinate complex with M. In one embodiment, L forms a 4-coordinate complex with M. Exemplary groups L include, but are not limited to:

-continued

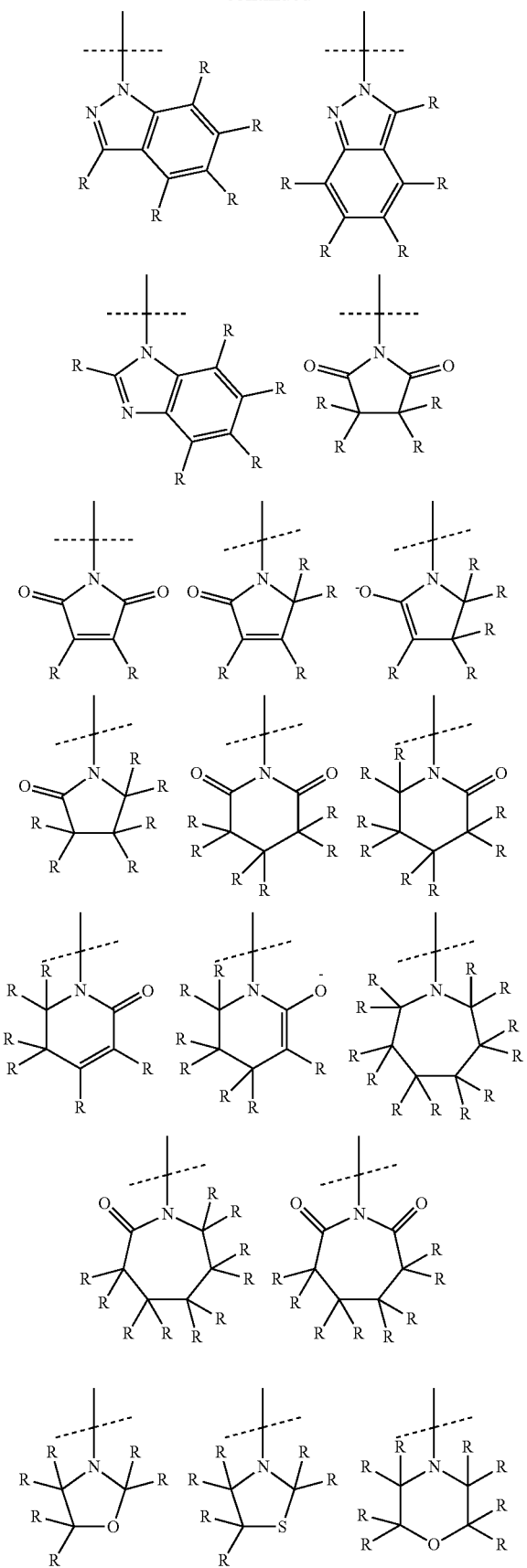

-continued

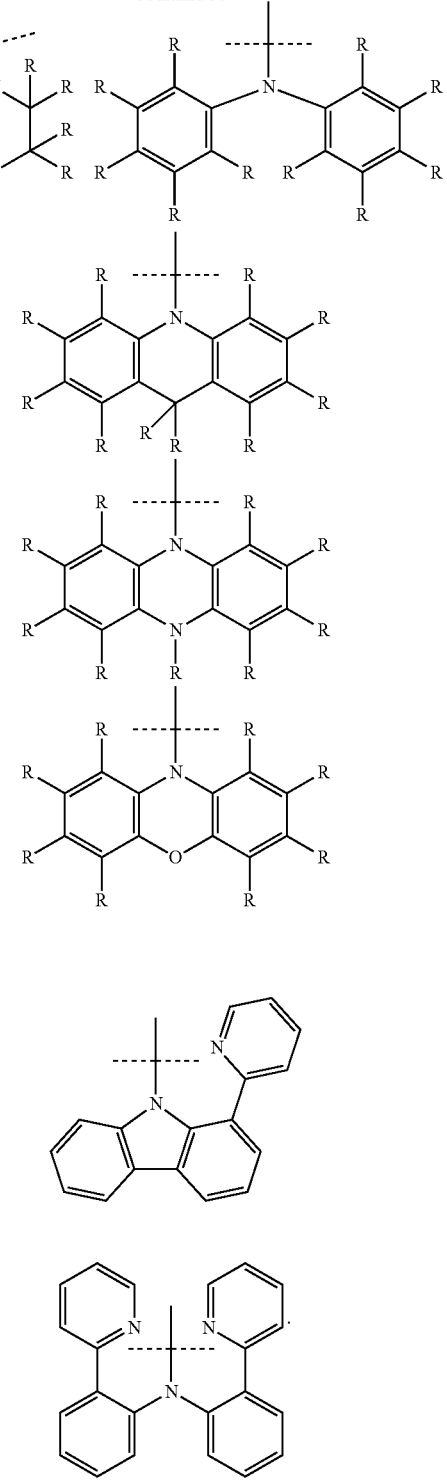

wherein each occurrence of R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and each occurrence of Z is independently C or N.

In one embodiment, ring C in Formula IIb is

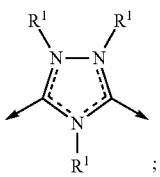

wherein arrows indicate coordination sites to M.

In another aspect, the present invention relates to compounds of Formula III or Formula IV:

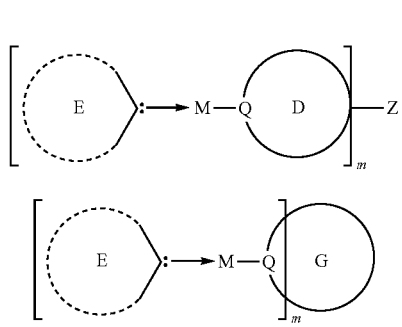

wherein E is a carbene coordinated to metal M;

each E can be the same or different;

each ring D is independently a single or fused carbocyclic ring or heterocyclic ring, which may be saturated or unsaturated, which is bound covalently bound to Z, wherein each ring D may be the same or different, and wherein each ring D is independently substituted with R;

Z is a linking group selected from the group consisting of a single bond, aryl, heteroaryl, alkyl, O, S, NR, and combinations thereof;

m is 2, 3, or 4;

G is a single or fused carbocyclic ring or heterocyclic ring, which may be saturated or unsaturated; which comprises m atoms Q; and which may be optionally substituted with one or more R.

each occurrence of R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

each occurrence of Q is independently C or N; and

M is Au, Ag, or Cu.

In one embodiment, the compound is a compound of Formula IIIa or Formula IVa

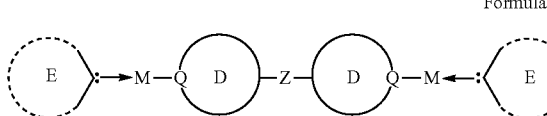

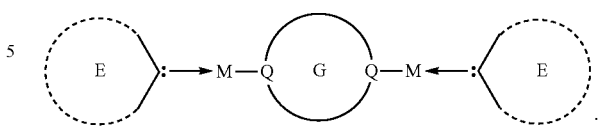

In one embodiment, each occurrence of Q is N.

In one embodiment, m is 2.

In one embodiment, E is selected from the group consisting of:

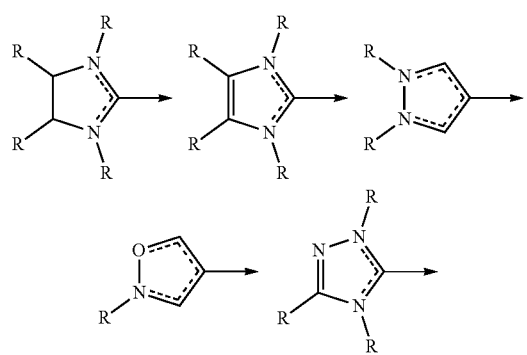

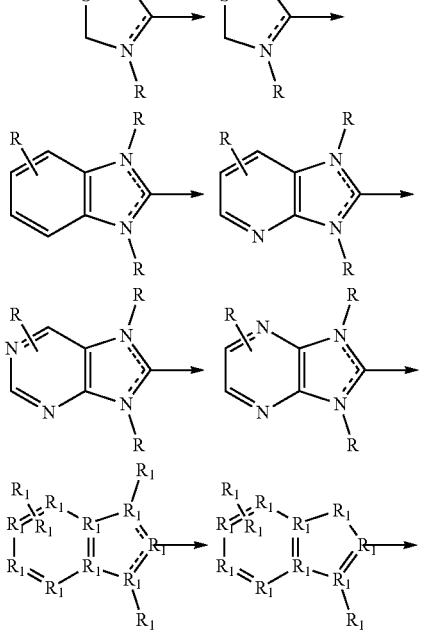

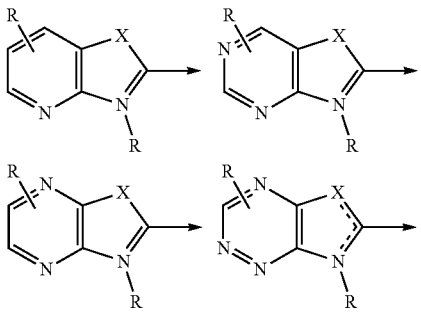

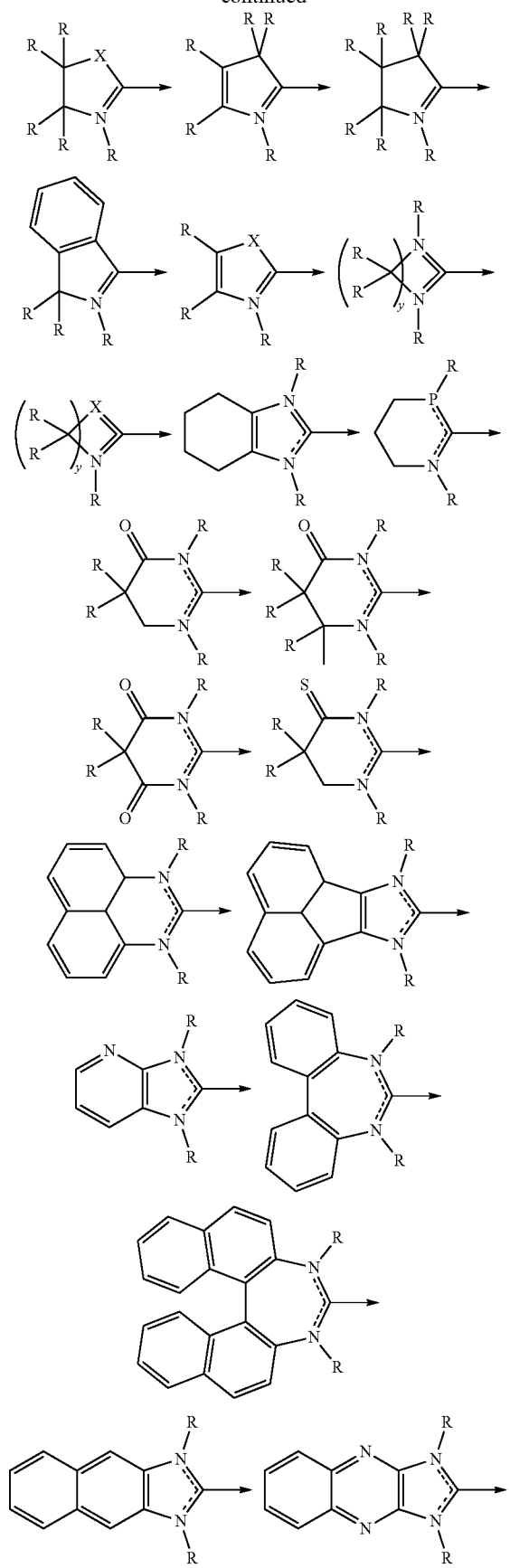
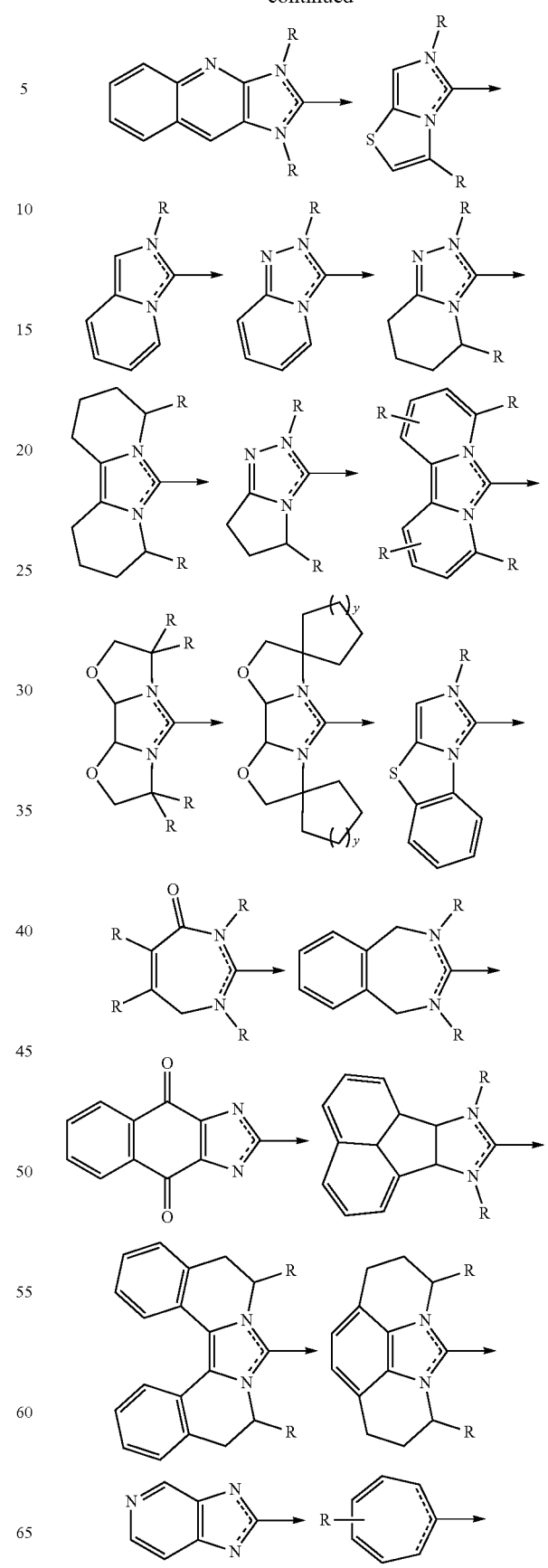

25

-continued

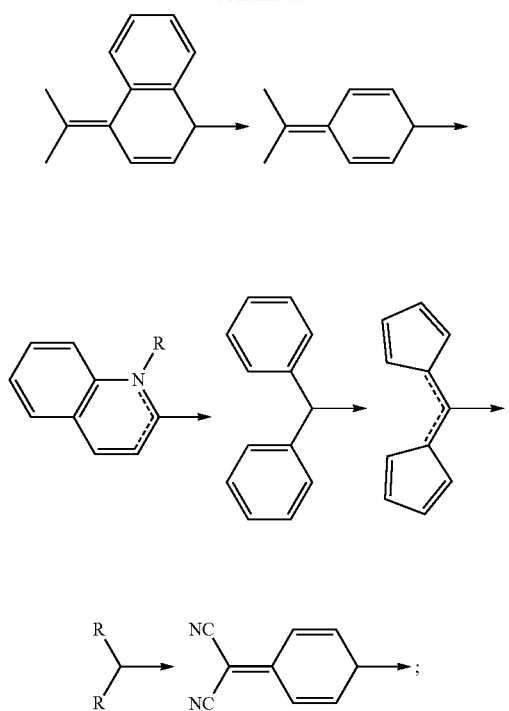

wherein each occurrence of R is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

any two adjacent groups R may together join to form a fused ring;

X represents O or S; and each occurrence of y is independently 1, 2, 3, or 4.

In one embodiment, E is

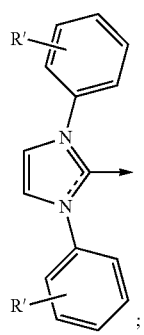

wherein each occurrence of R' is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

26

In one embodiment, G is selected from the group consisting of

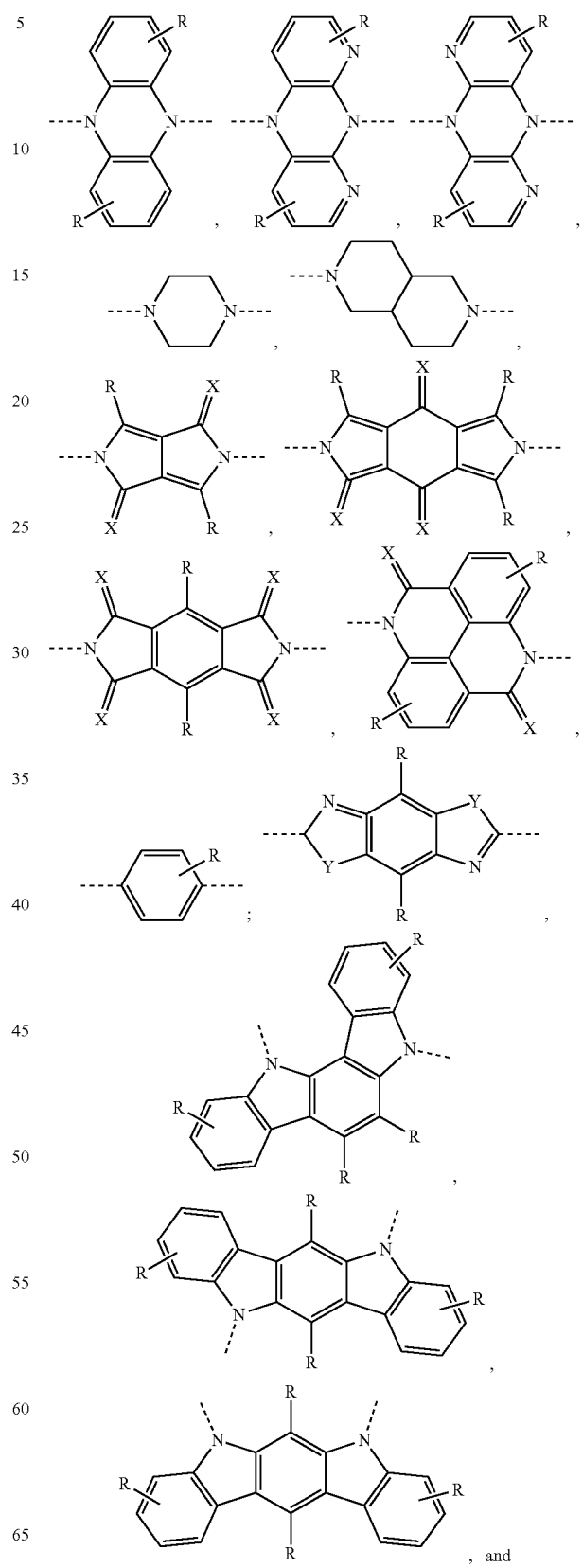

, and

-continued

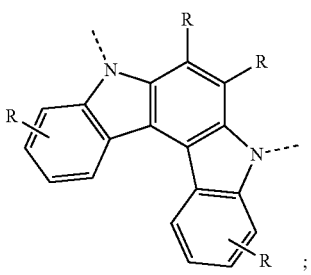

wherein dashed lines indicate coordination to the metal M;

X is O, S, or C(R$^6$)$_2$;

Y is O, S, or C(R$^6$)$_2$;

each occurrence of R$^6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and two R$^6$ may optionally together form a ring.

In one embodiment, each D is independently selected from the group consisting of phenyl, fluorene, naphthalene, triphenylene, dibenzothiophene, dibenzofuran, dibenzoselenophene, carbazole, indolocarbazole, imidazole, pyridine, triazine, and benzimidazole.

In one embodiment,

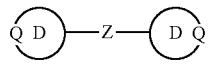

is represented by

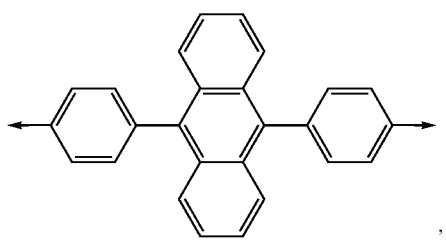

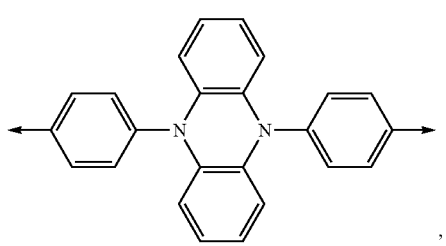

-continued

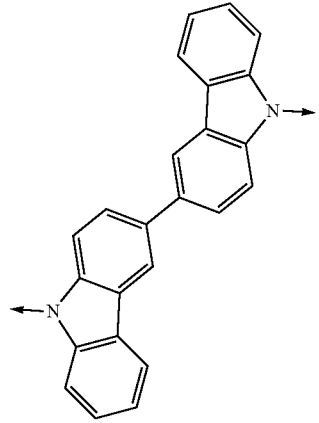

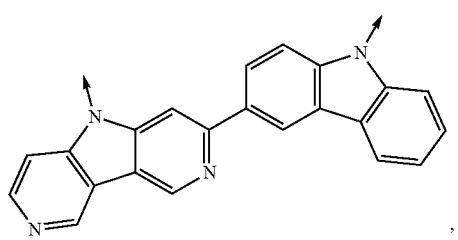

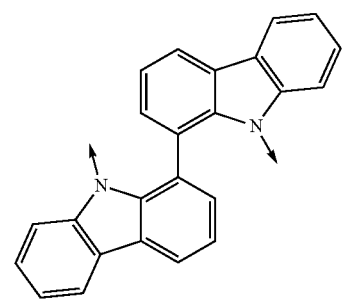

, or

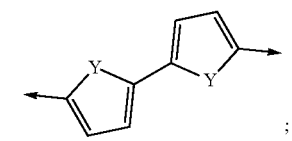

;

wherein arrows indicate coordination to the metal M;

Y is O, S, SO, SO$_2$, NR$^7$, or C(R$^7$)$_2$;

each occurrence of R$^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and two R$^7$ may optionally together form a ring.

In one embodiment, the compound of Formula III is selected from the group consisting of:
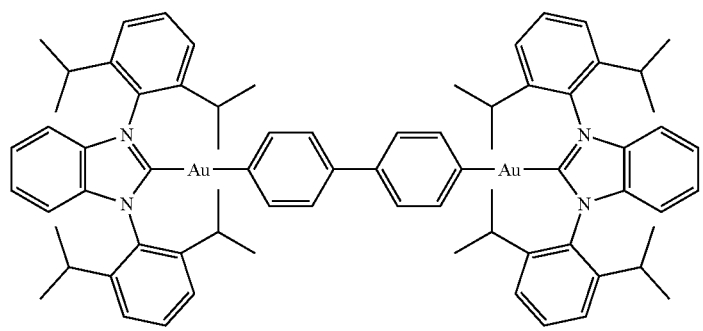
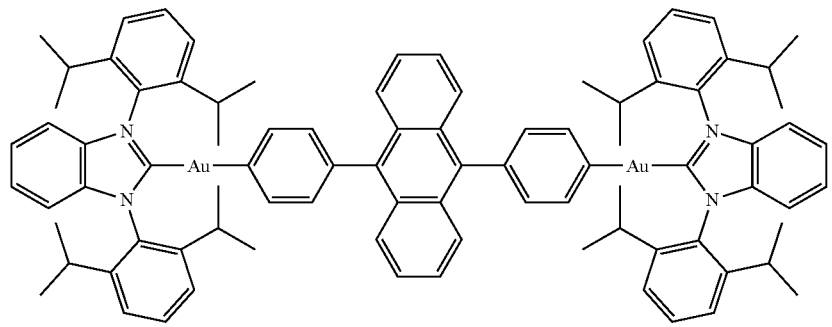
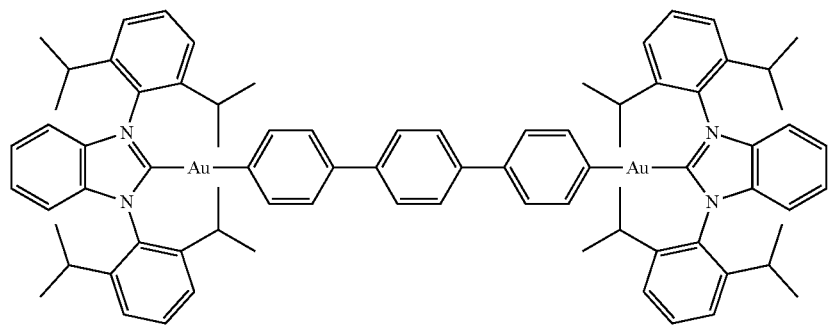
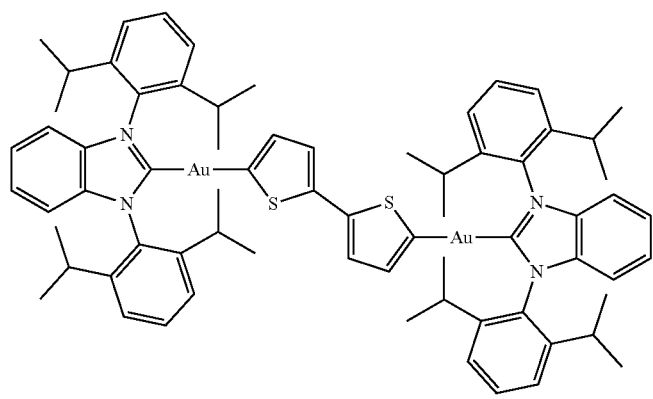

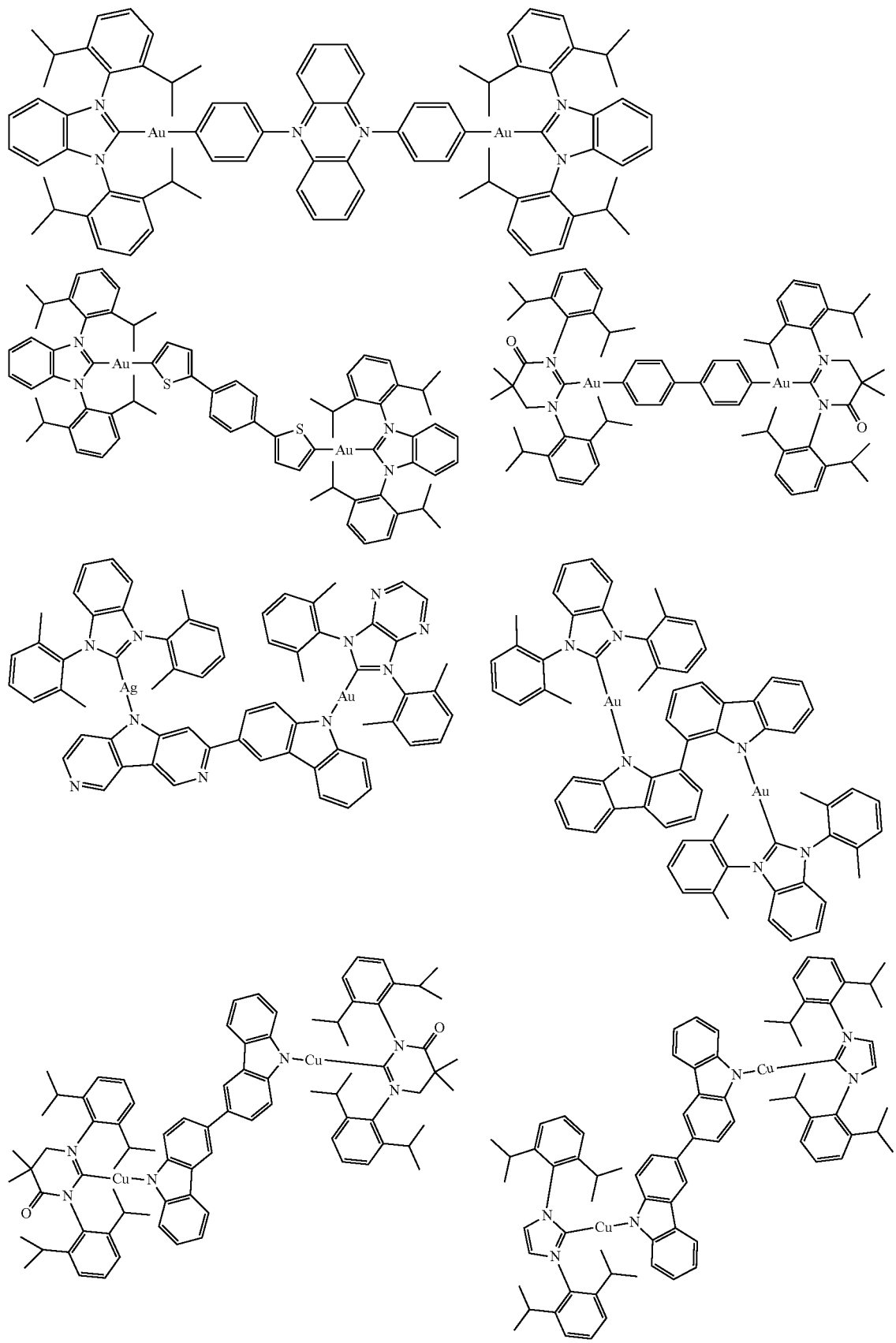

In one embodiment, the compound of Formula IV is selected from the group consisting of:
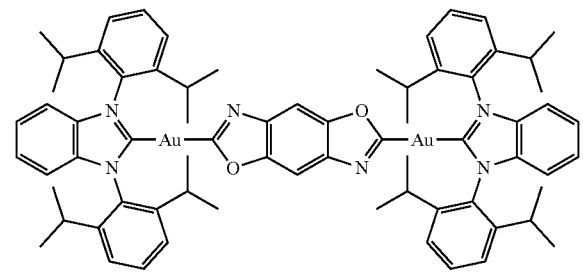
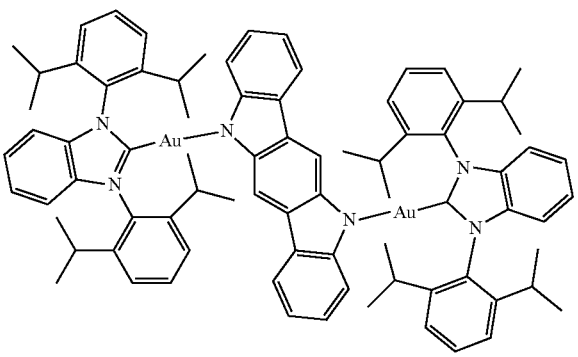
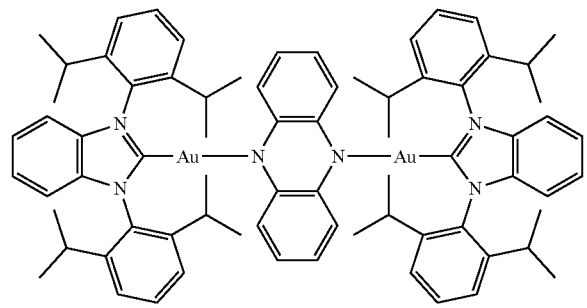
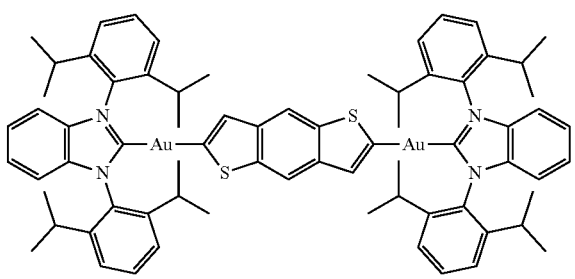
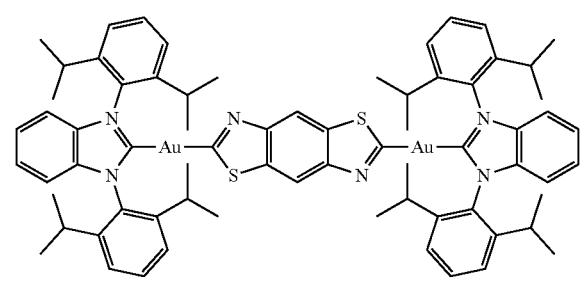
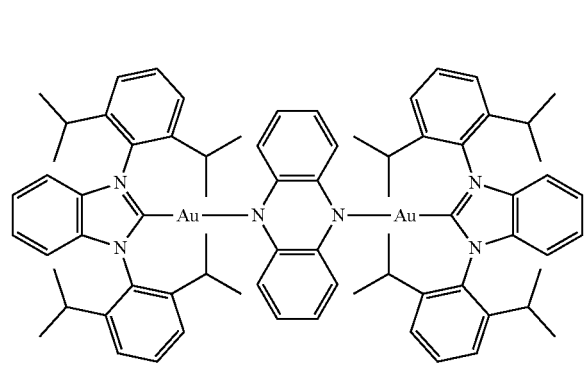
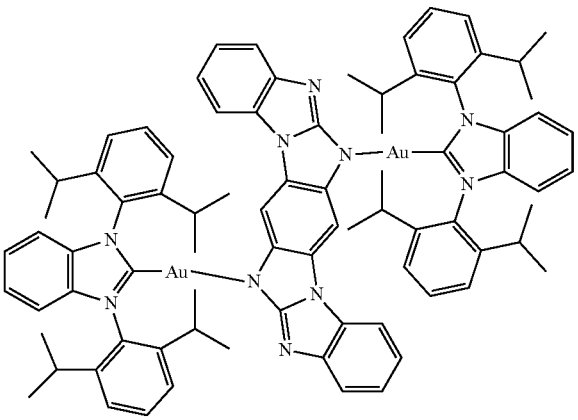
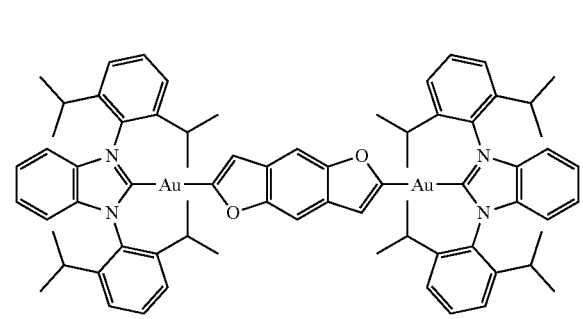
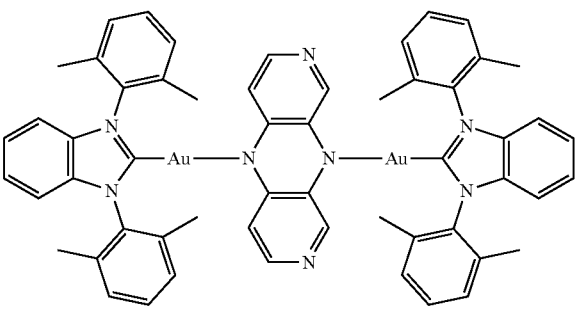

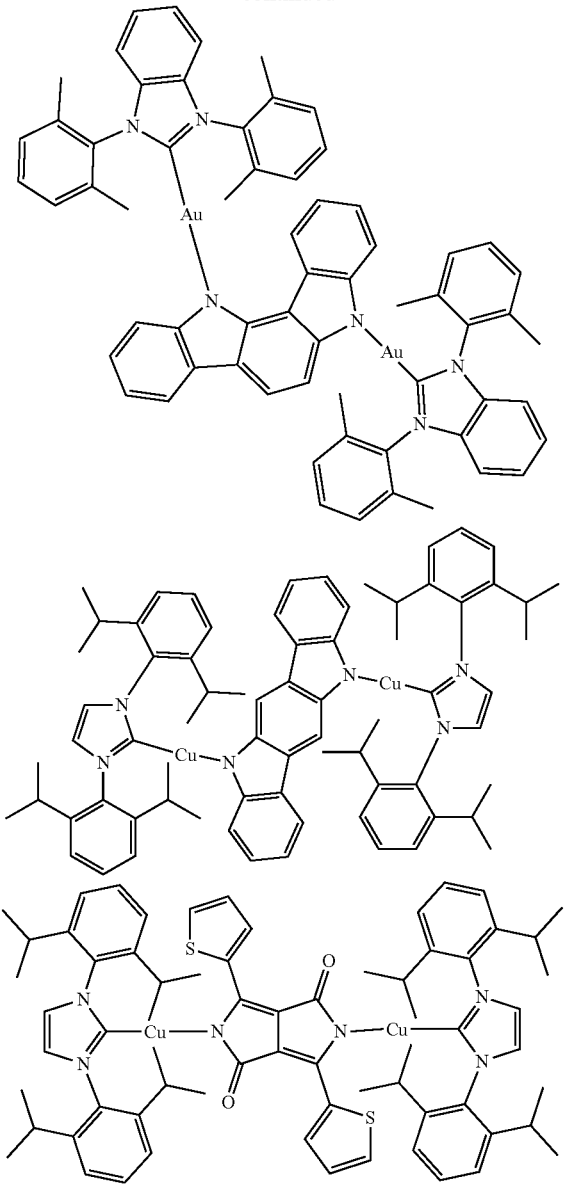

In another aspect, the present invention relates to an organic light emitting device (OLED) comprising an anode; a cathode; and an organic layer, disposed between the anode and the cathode, comprising a compound of the present invention.

A consumer product comprising an organic light-emitting device (OLED) is also described. The OLED includes an anode, a cathode, and an organic layer disposed between the anode and the cathode, wherein the organic layer includes a compound of the present invention.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer. In some embodiments, the compound can be homoleptic (each ligand is the same). In some embodiments, the compound can be heteroleptic (at least one ligand is different from others). When there are more than one ligand coordinated to a metal, the ligands can all be the same in some embodiments. In some other embodiments, at least one ligand is different from the other ligands. In some embodiments, every ligand can be different from each other. This is also true in embodiments where a ligand being coordinated to a metal can be linked with other ligands being coordinated to that metal to form a tridentate, tetradentate, pentadentate, or hexadentate ligands. Thus, where the coordinating ligands are being linked together, all of the ligands can be the same in some embodiments, and at least one of the ligands being linked can be different from the other ligand(s) in some other embodiments.

In some embodiments, the compound can be used as a phosphorescent sensitizer in an OLED where one or multiple layers in the OLED contains an acceptor in the form of one or more fluorescent and/or delayed fluorescence emitters. In some embodiments, the compound can be used as one component of an exciplex to be used as a sensitizer. As a phosphorescent sensitizer, the compound must be capable of energy transfer to the acceptor and the acceptor will emit the energy or further transfer energy to a final emitter. The acceptor concentrations can range from 0.001% to 100%. The acceptor could be in either the same layer as the phosphorescent sensitizer or in one or more different layers. In some embodiments, the acceptor is a TADF emitter. In some embodiments, the acceptor is a fluorescent emitter. In some embodiments, the emission can arise from any or all of the sensitizer, acceptor, and final emitter.

According to another aspect, a formulation comprising the compound described herein is also disclosed.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitutions. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

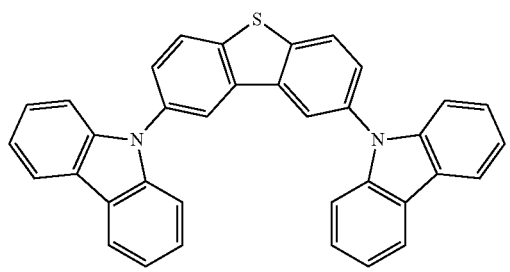

,

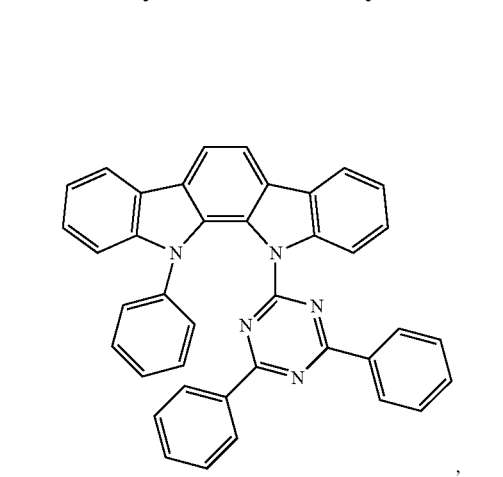

,

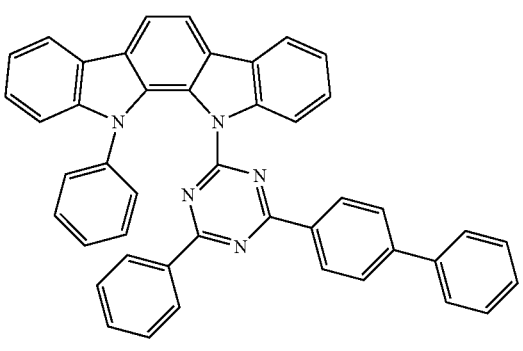

,

-continued

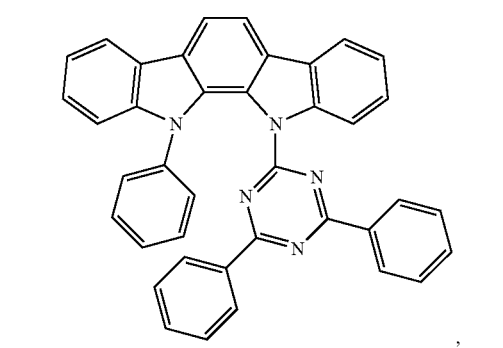

,

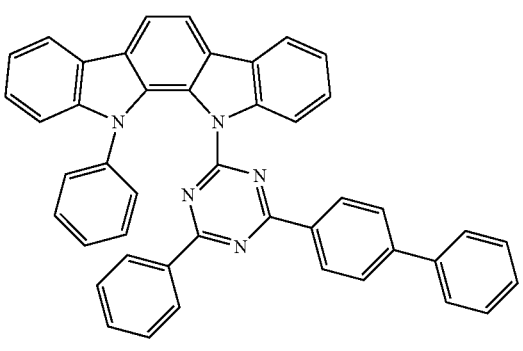

,

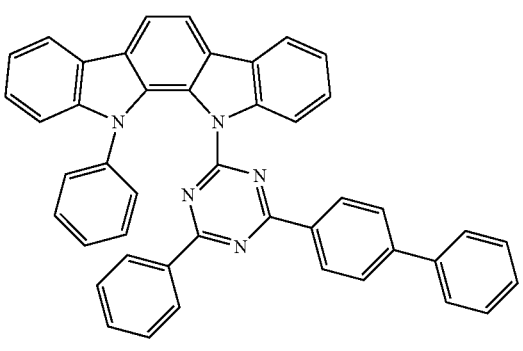

,

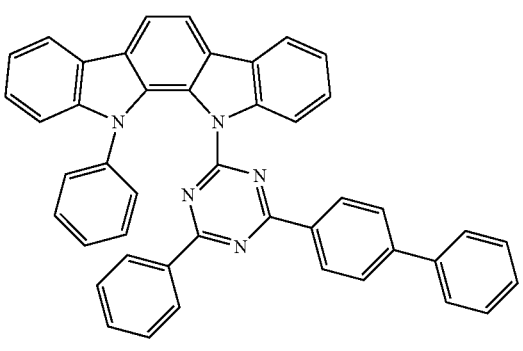

,

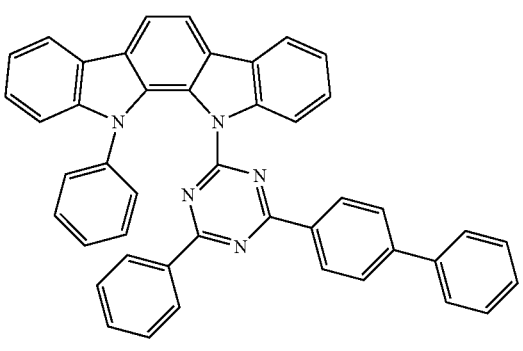

,

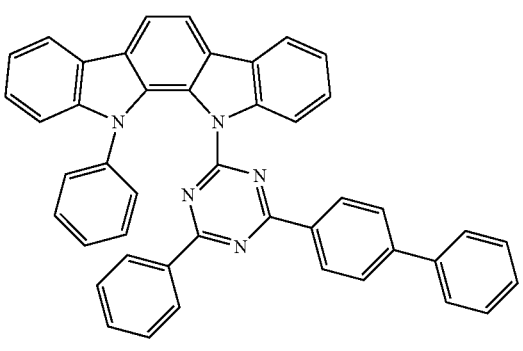

,

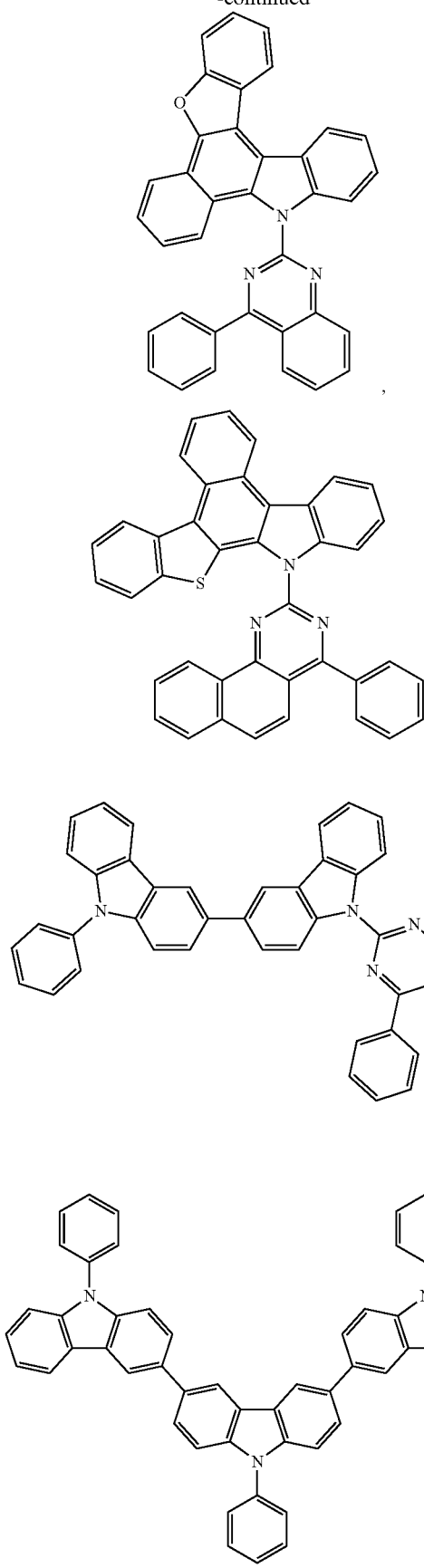
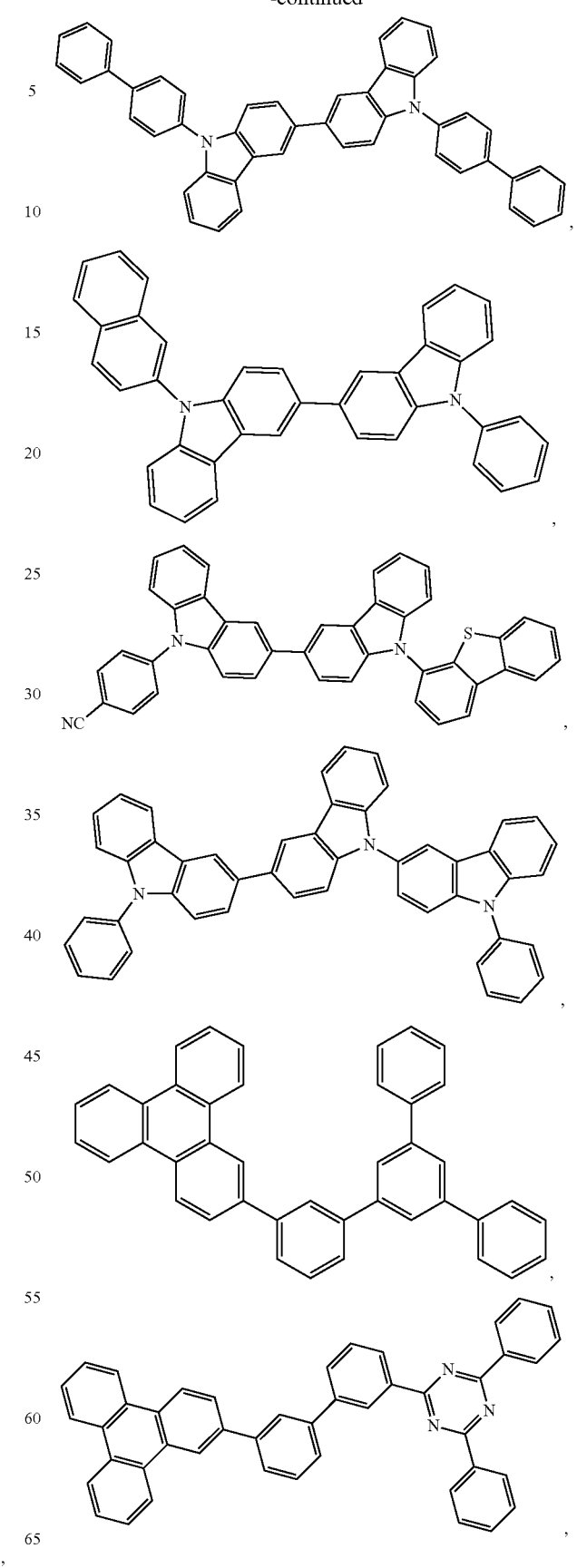

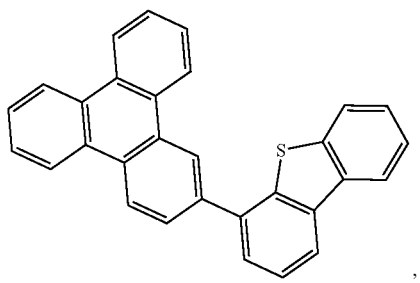

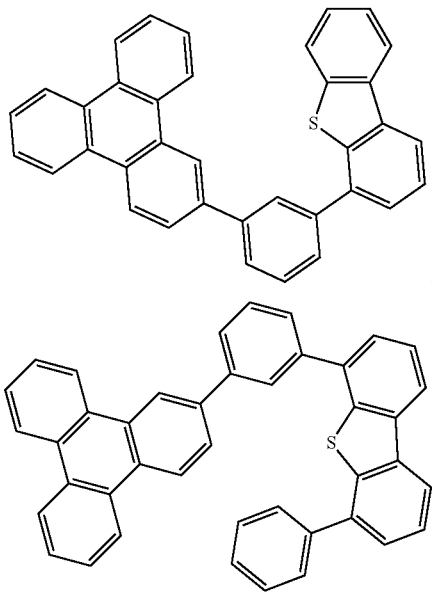

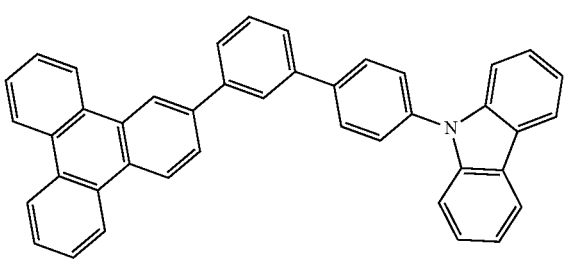

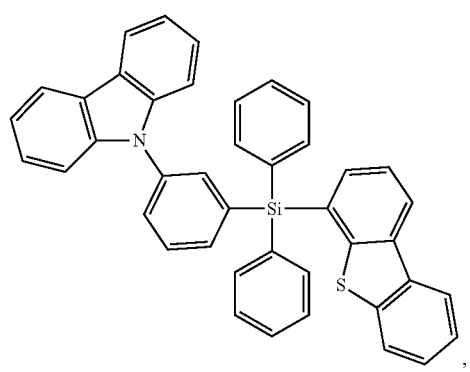

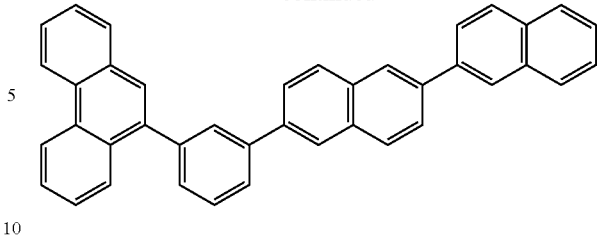

and combinations thereof.

Additional information on possible hosts is provided below.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure. In other words, a monovalent or polyvalent variant of the inventive compound can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond to the rest of the chemical structure.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.
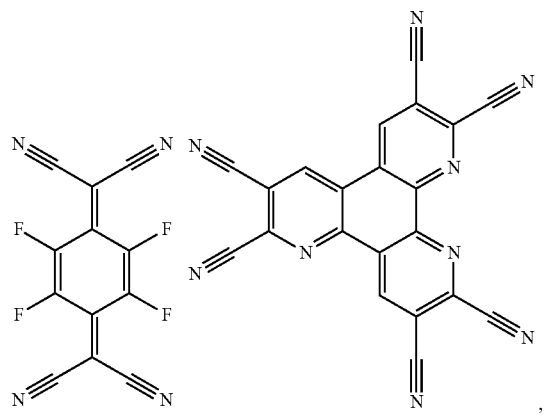
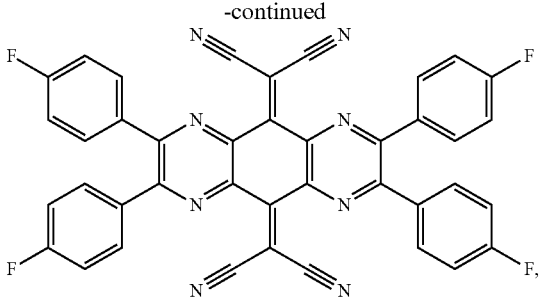
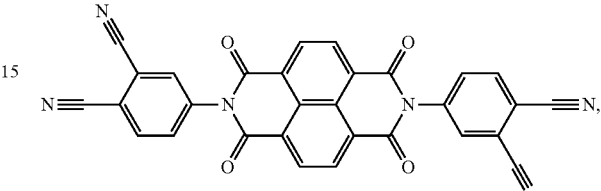
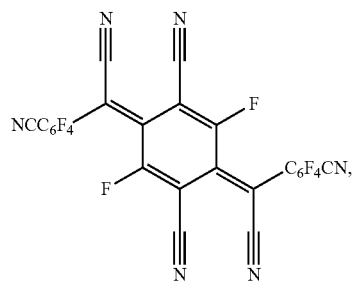
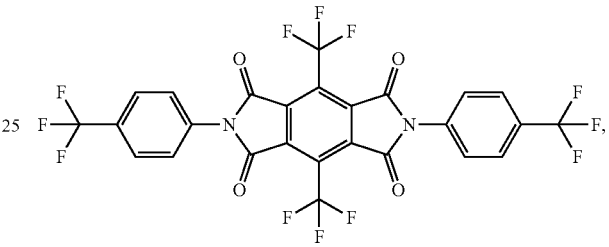
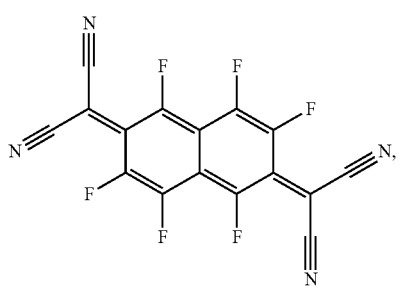
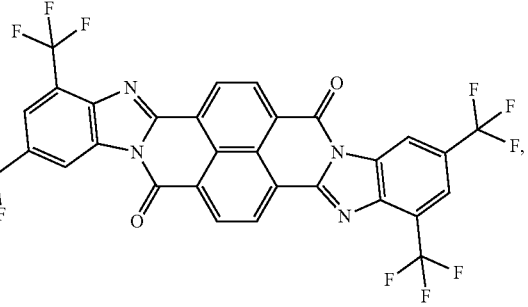
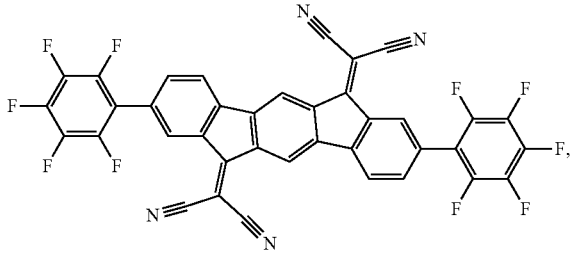
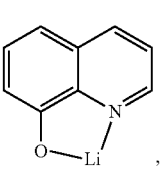, and 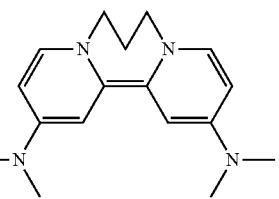

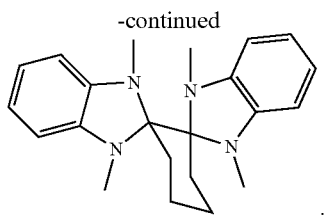

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

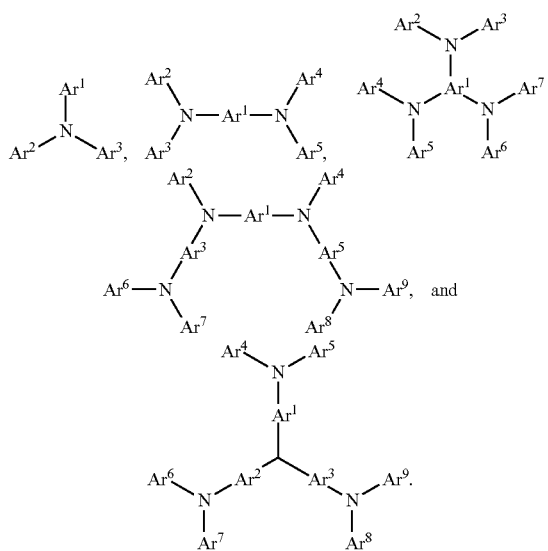

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

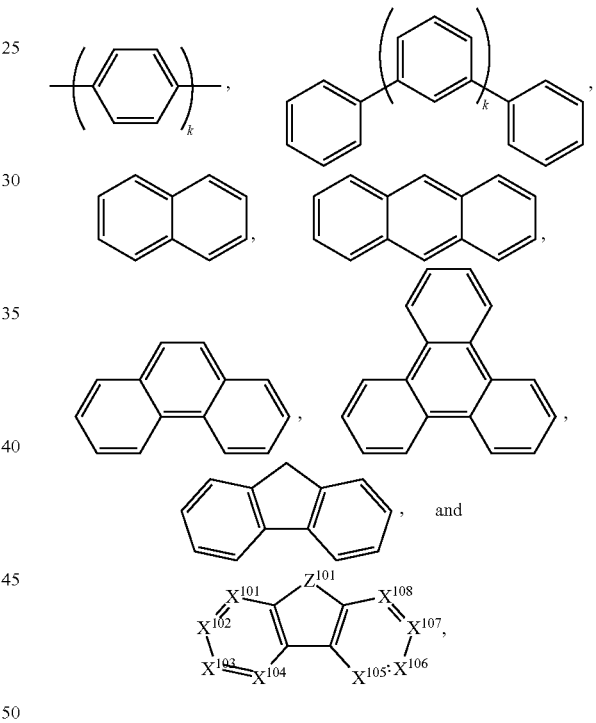

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

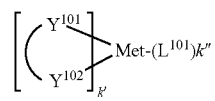

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102}))$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, US06517957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5639914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

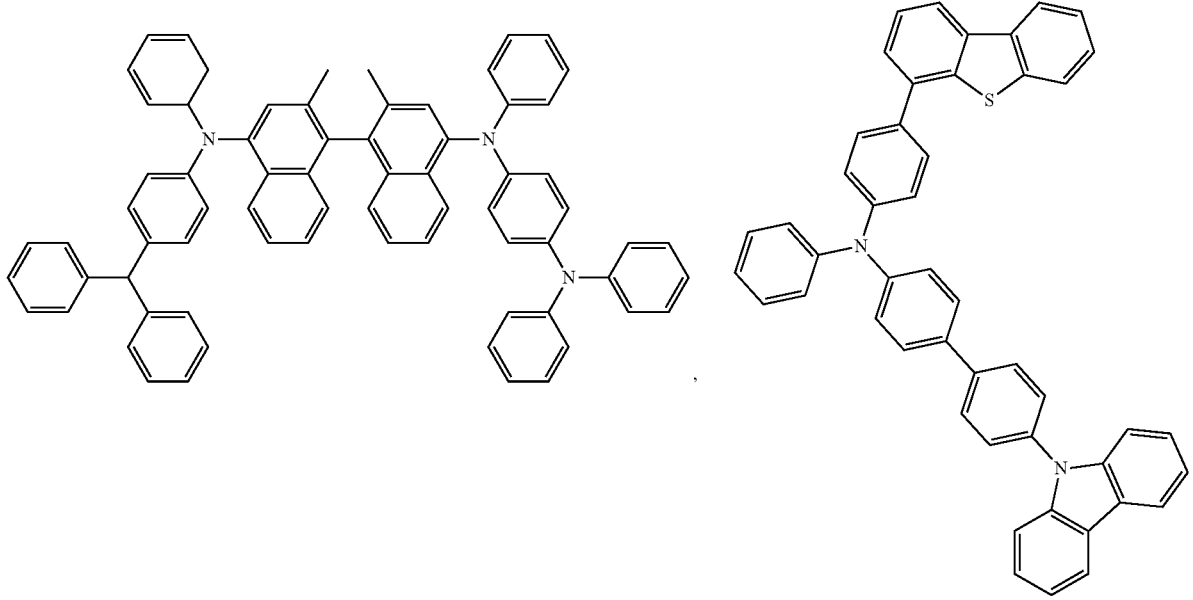

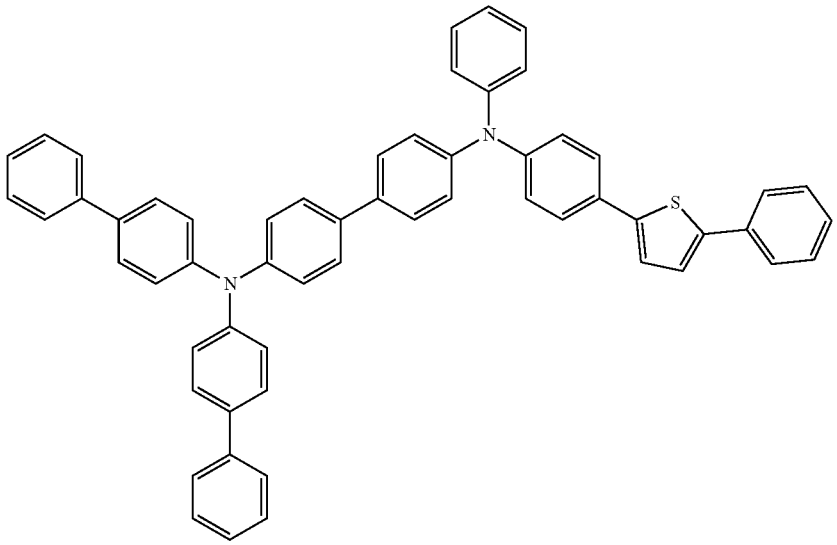

-continued
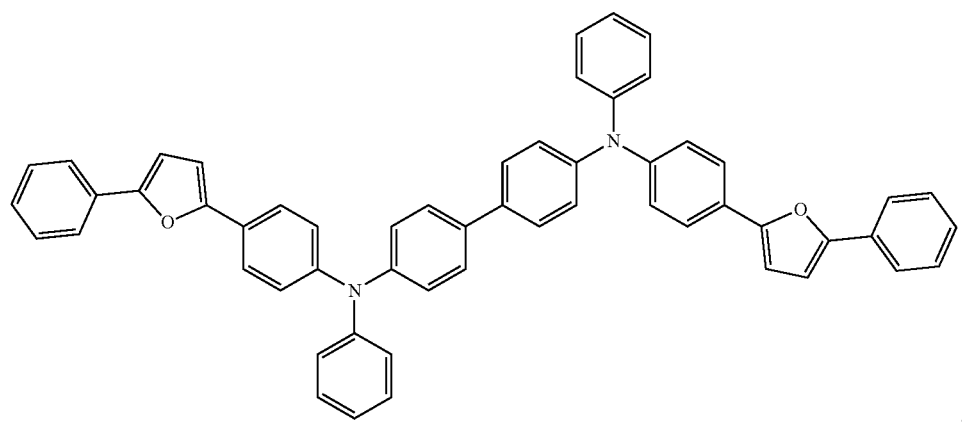
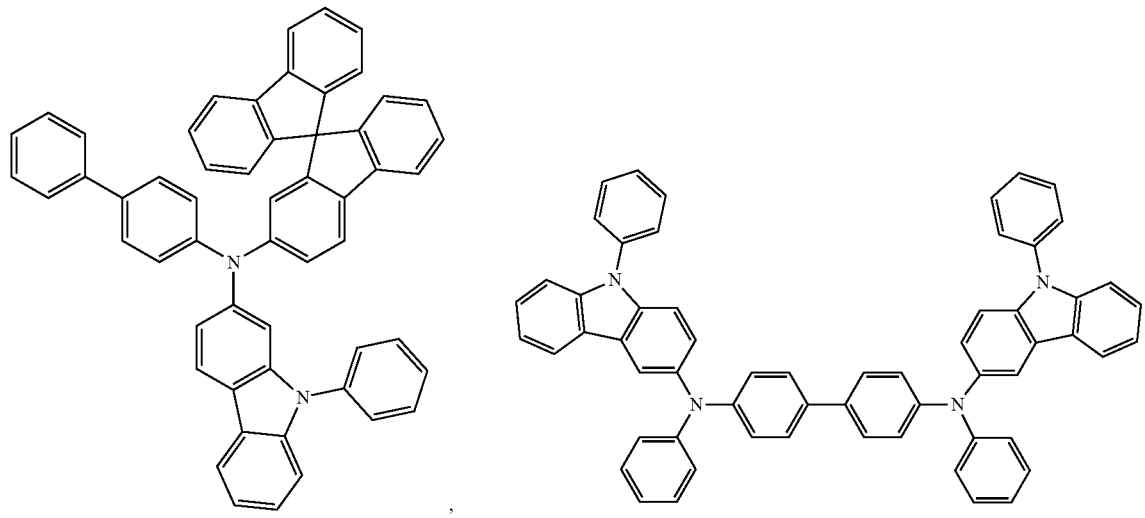
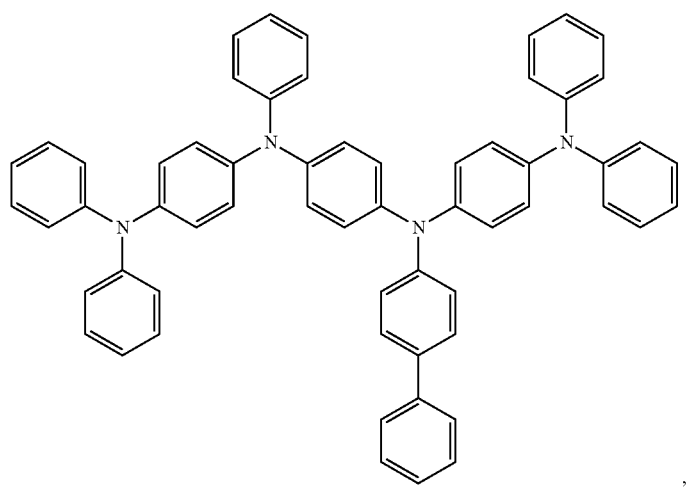

-continued
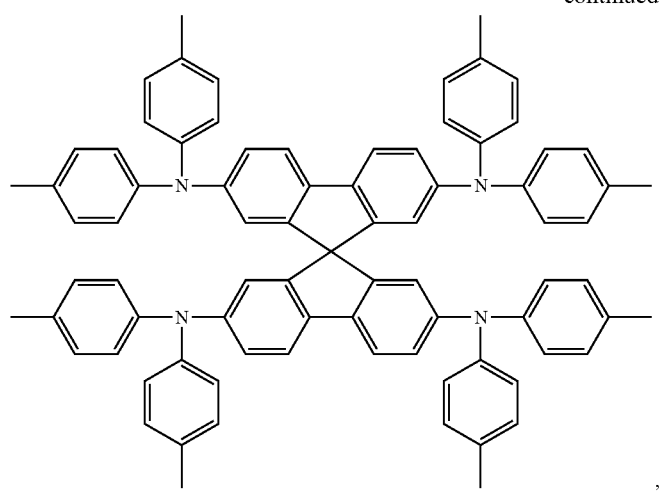
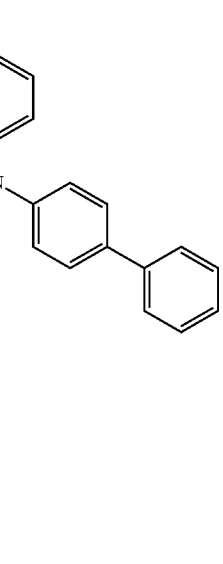
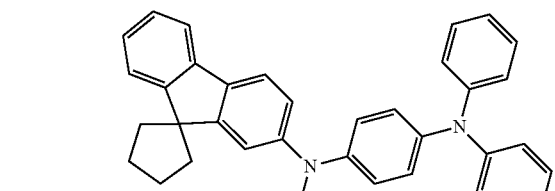
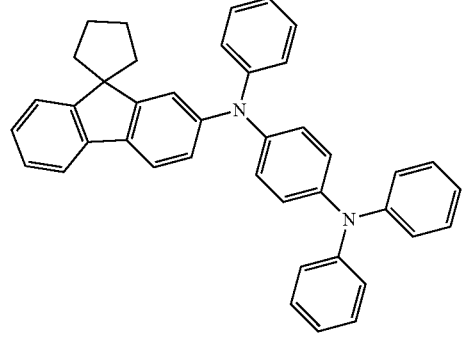
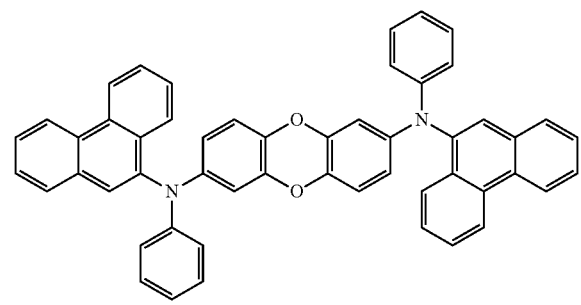

-continued
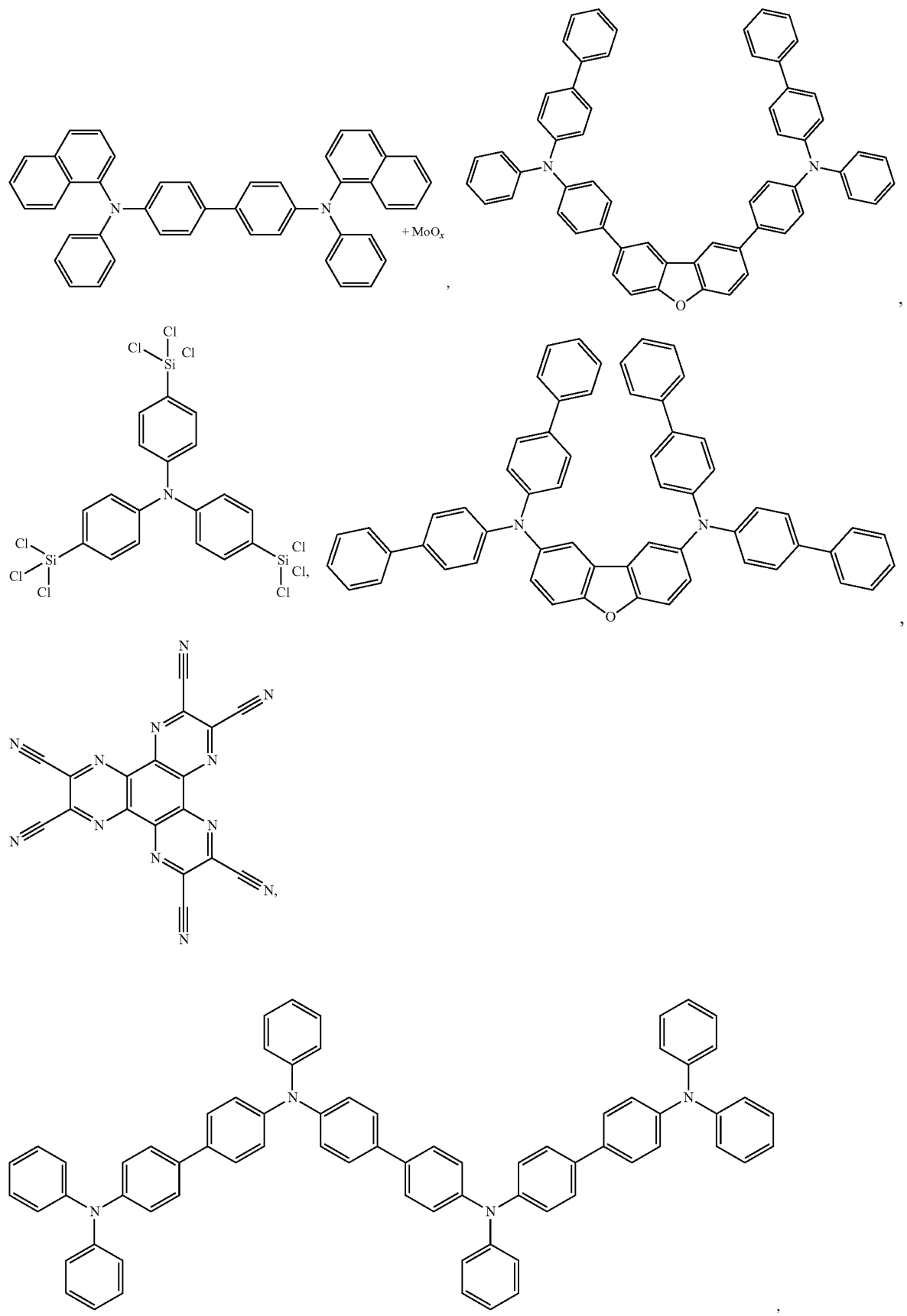

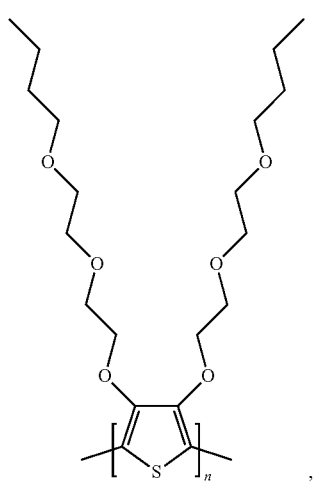
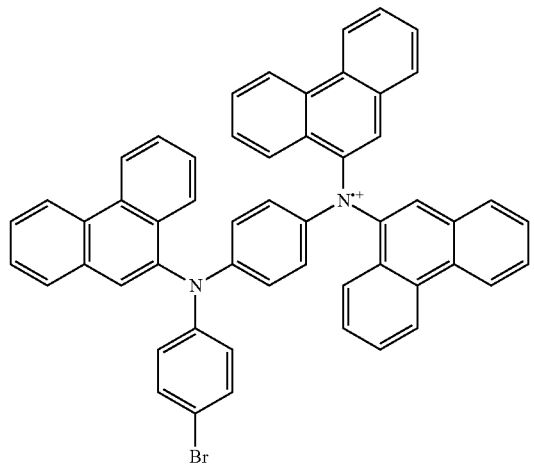
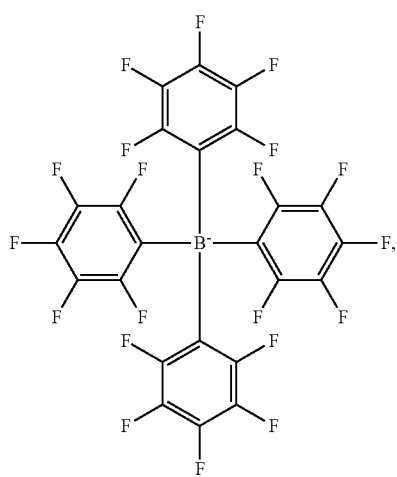
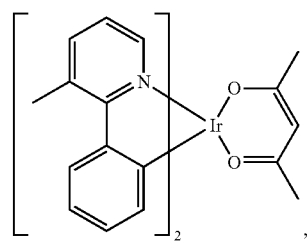
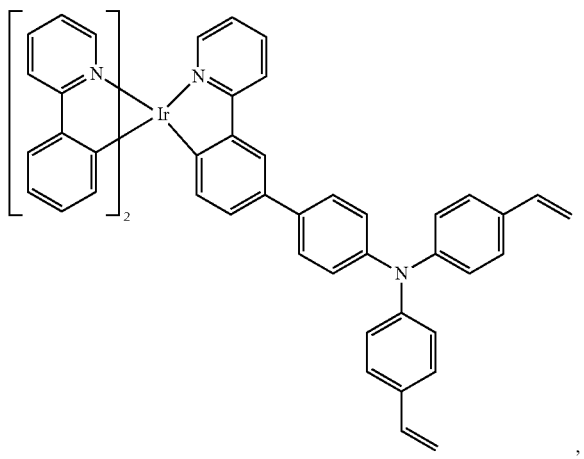
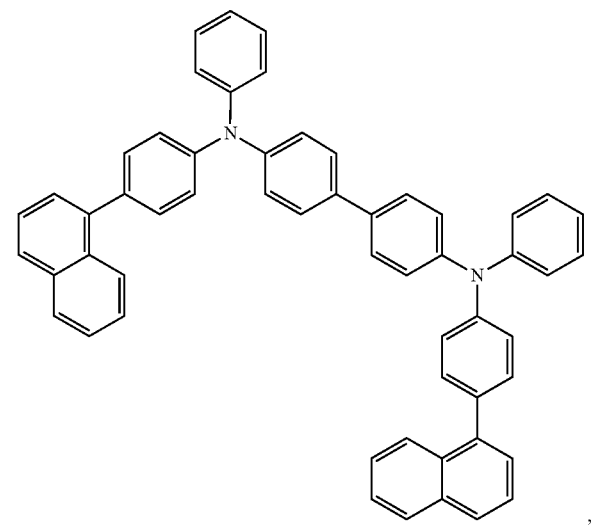

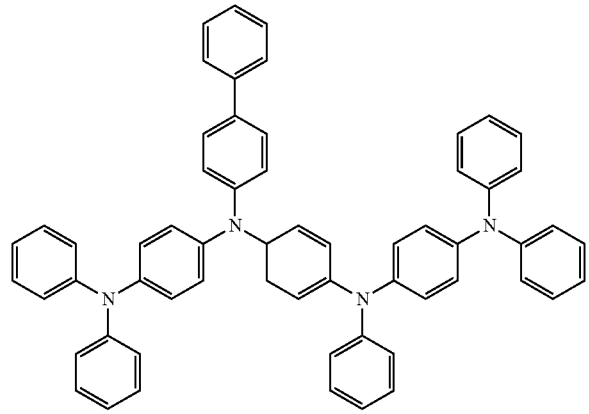
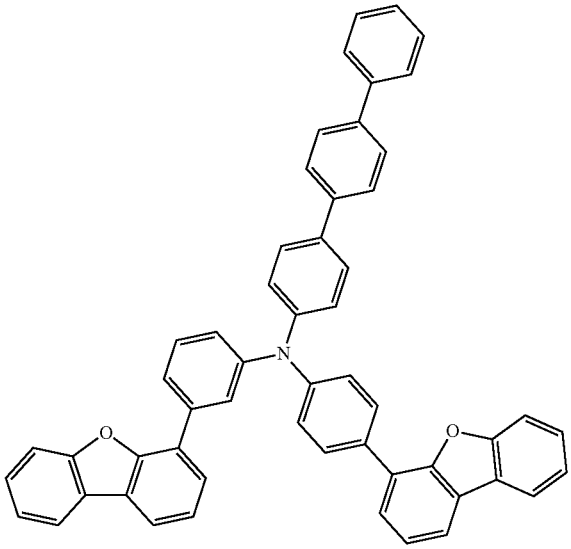
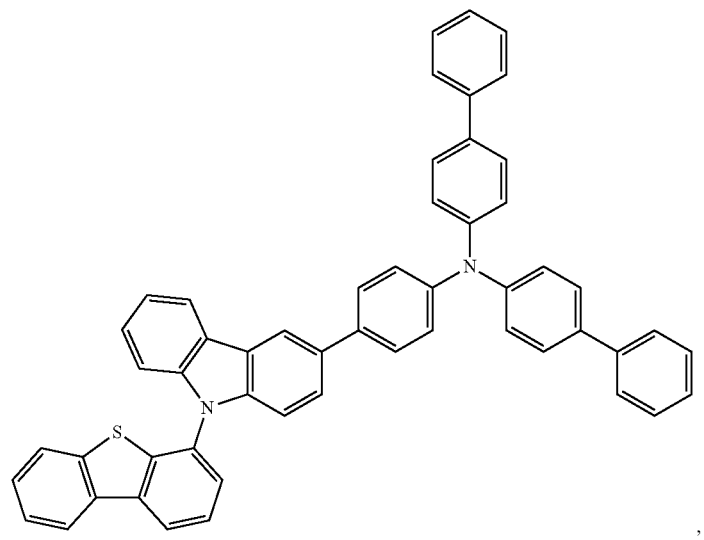
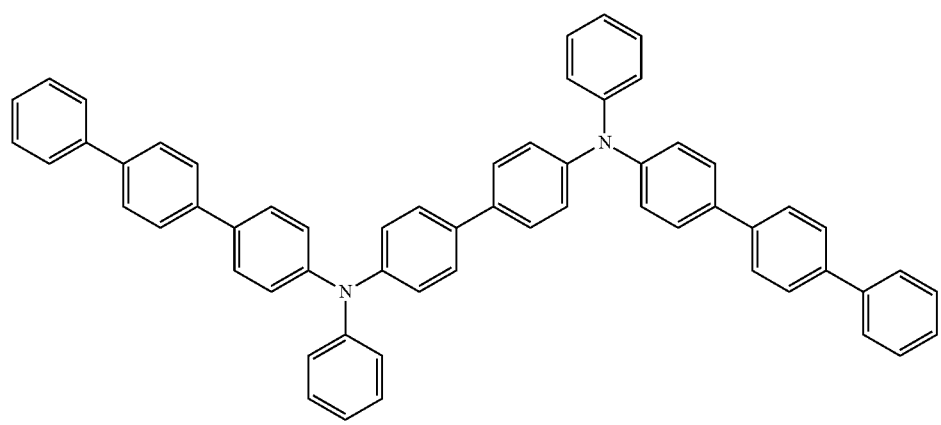

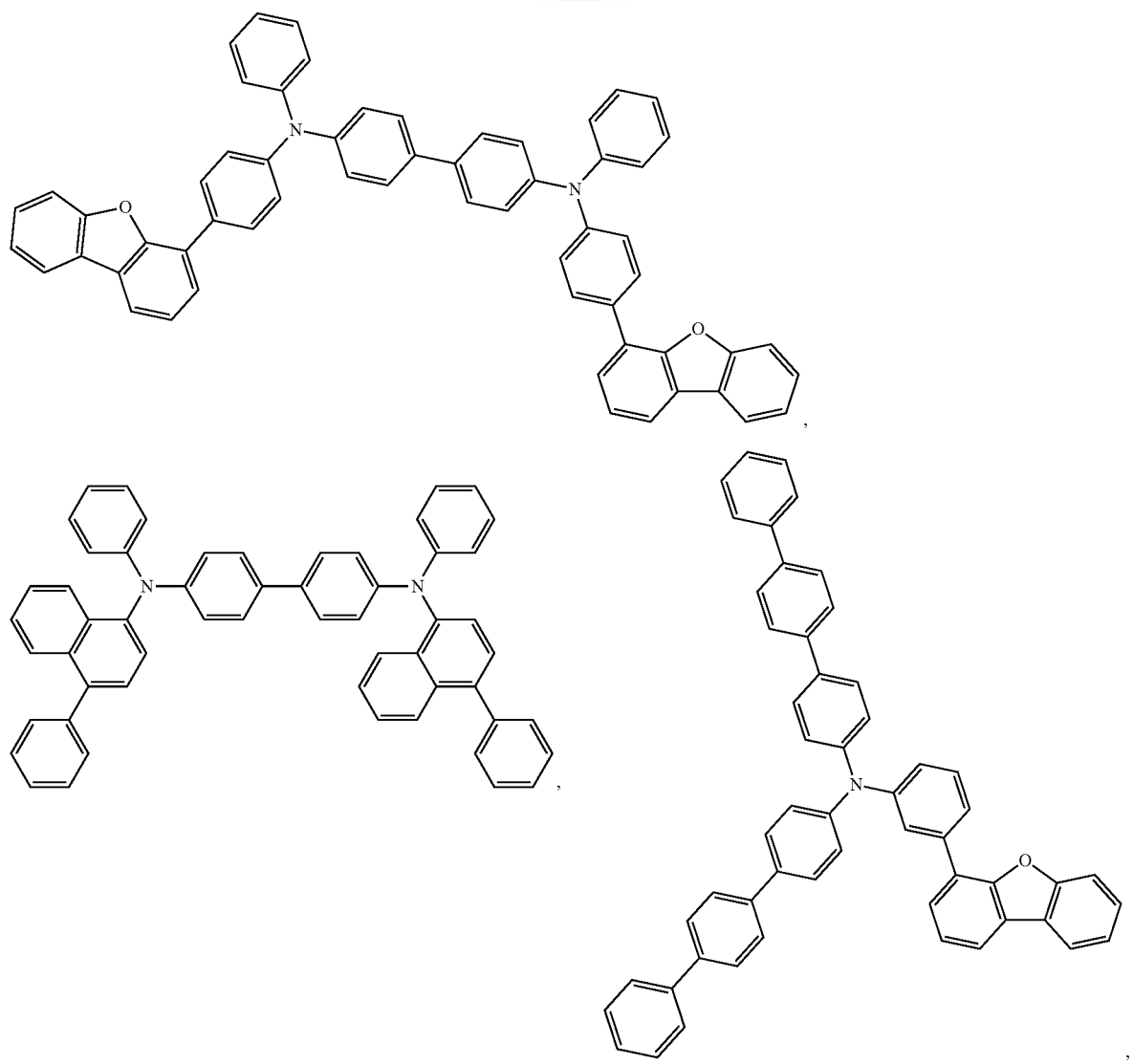
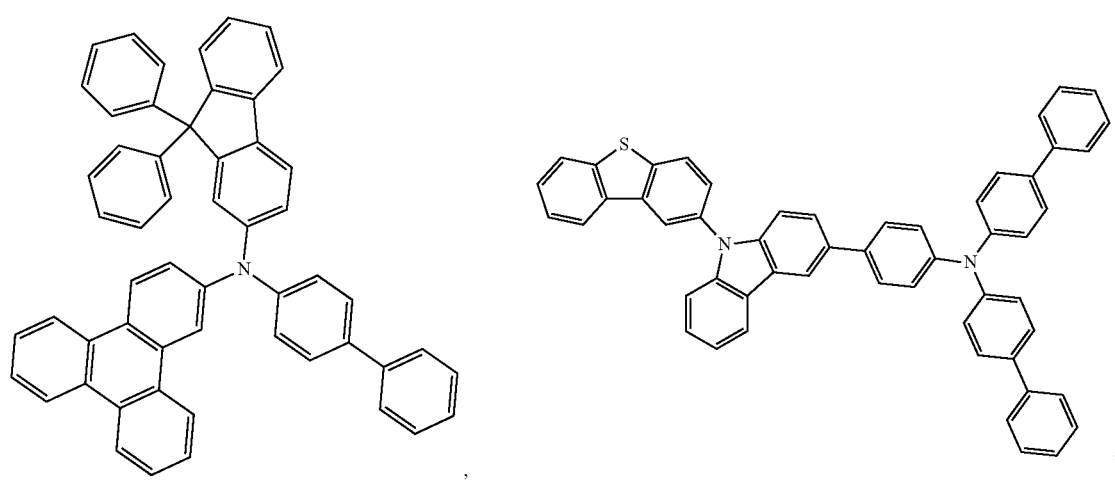

-continued
61
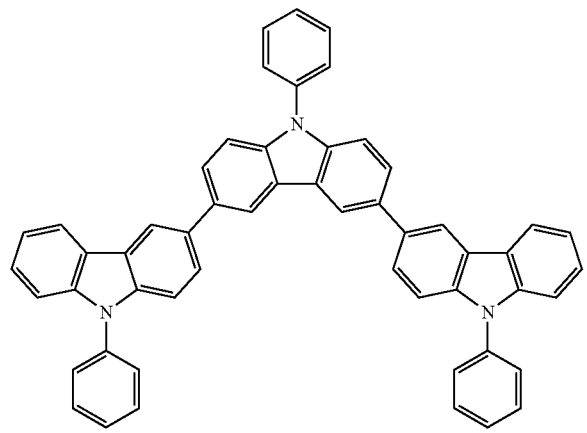
62
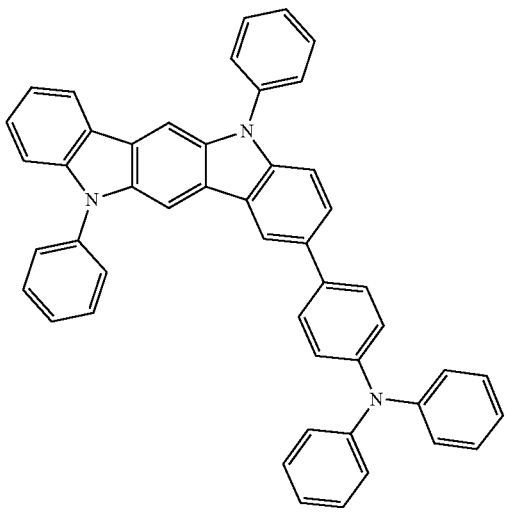
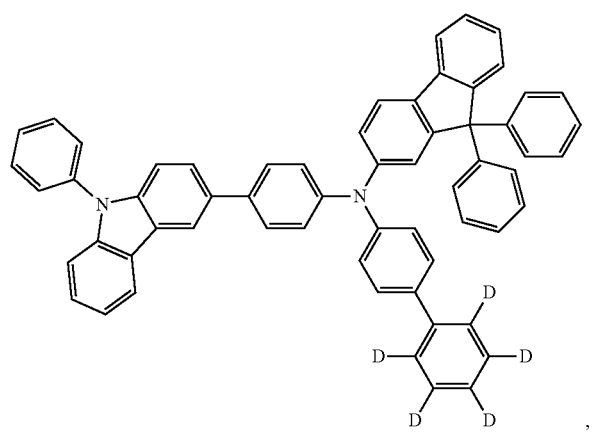
,
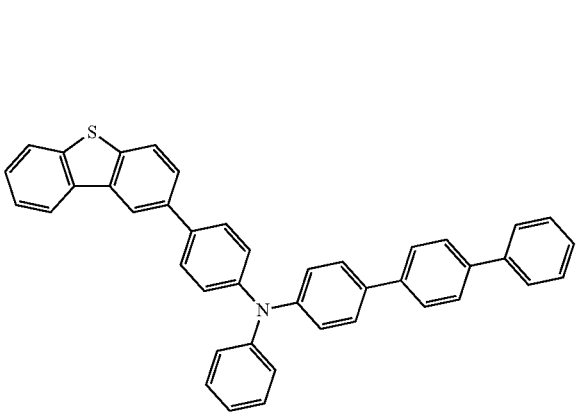
,
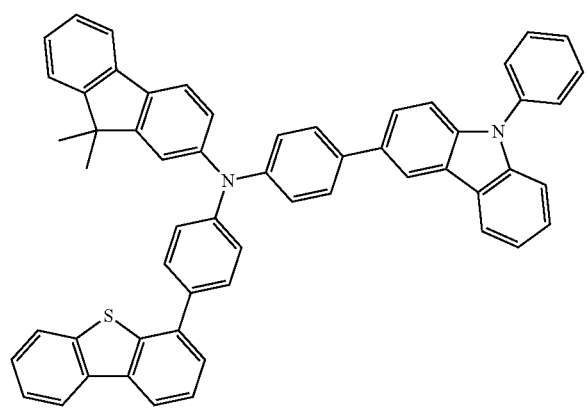
,
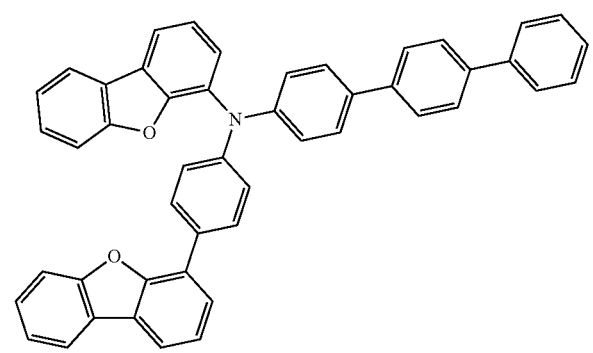
,

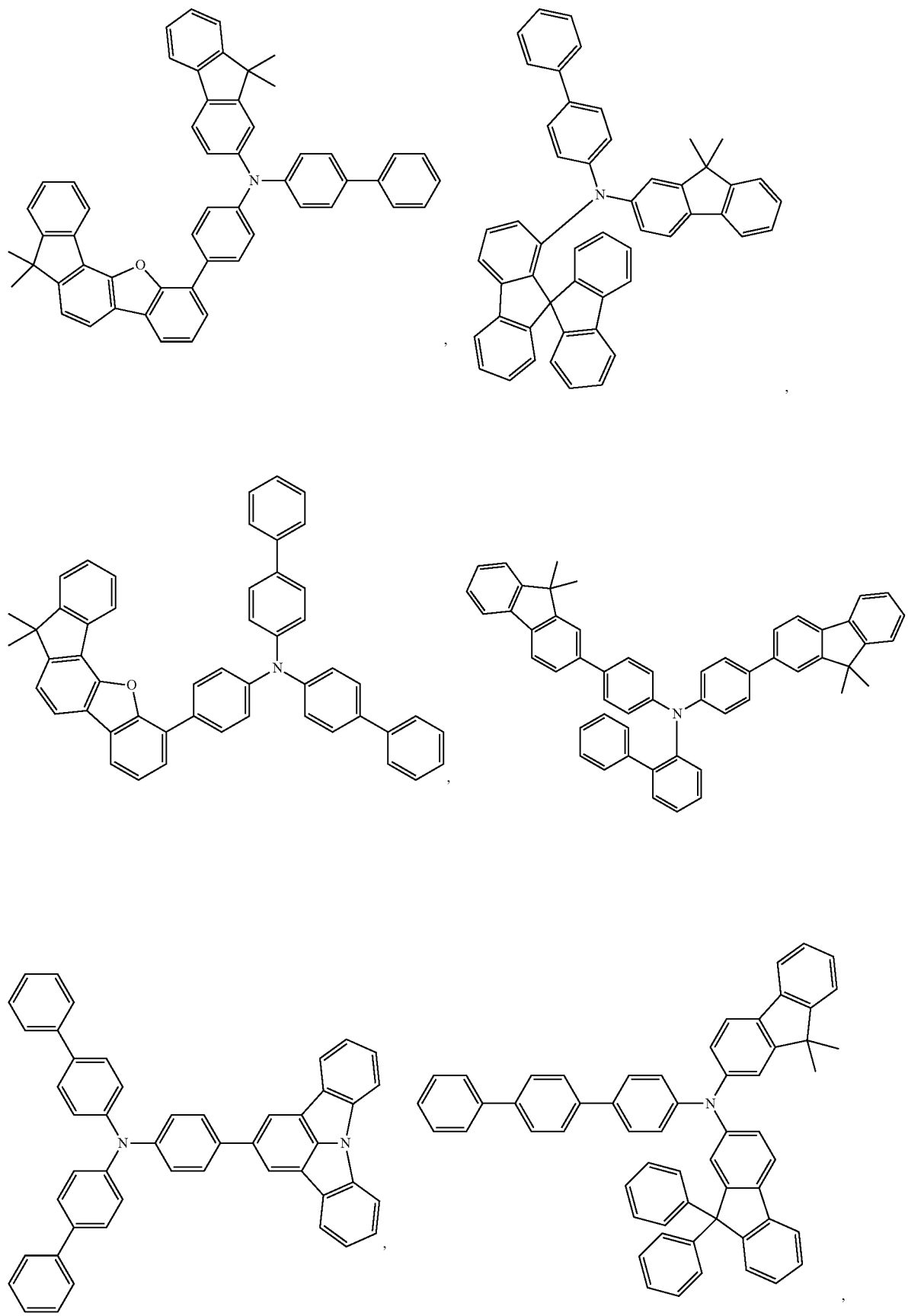

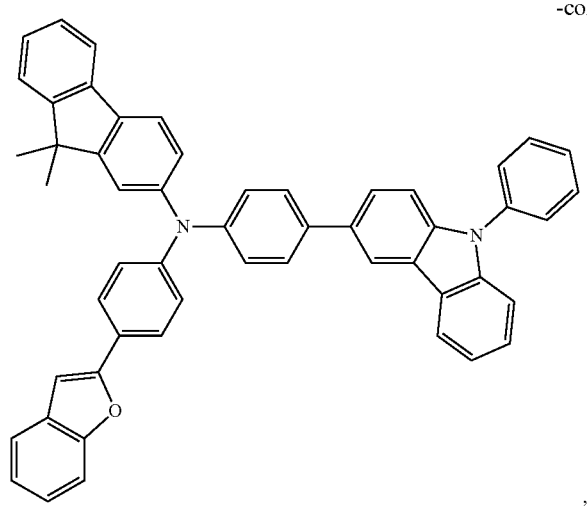
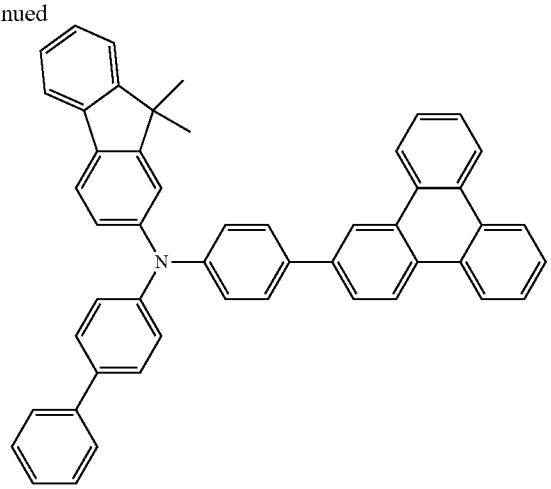
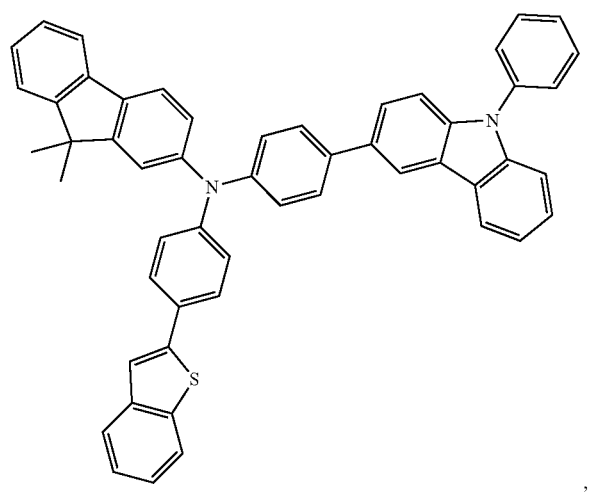
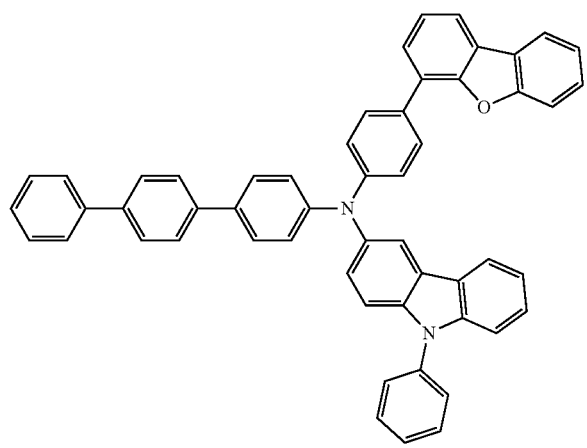
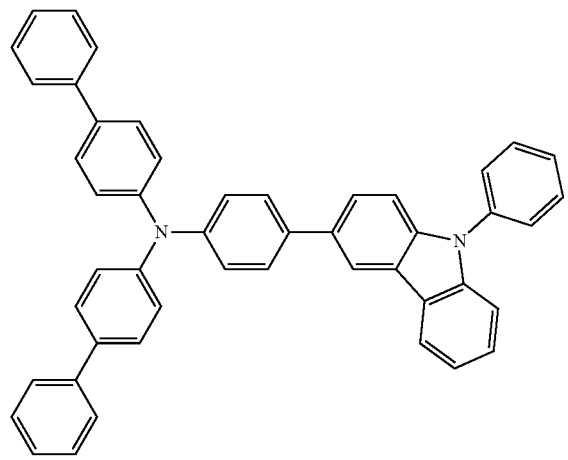
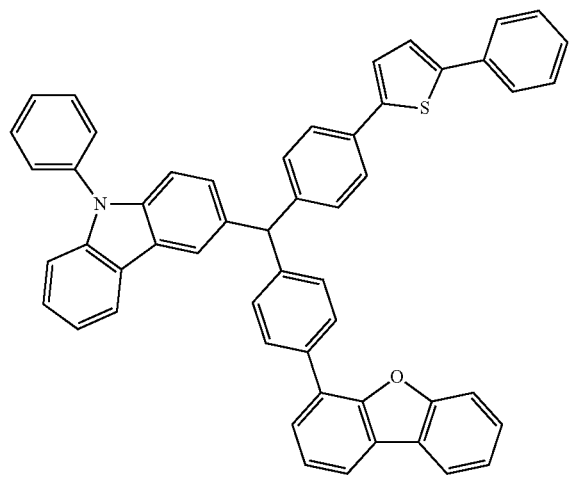

-continued
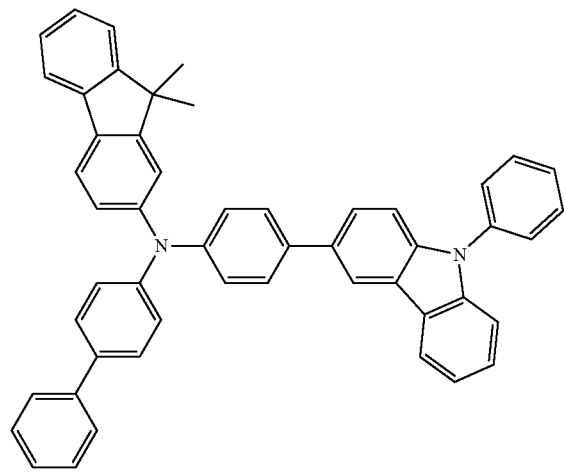
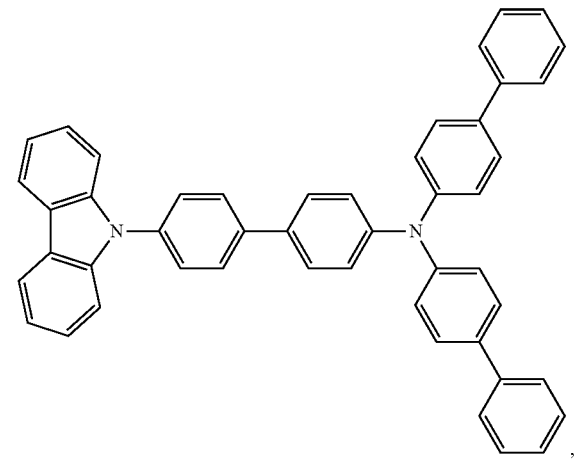
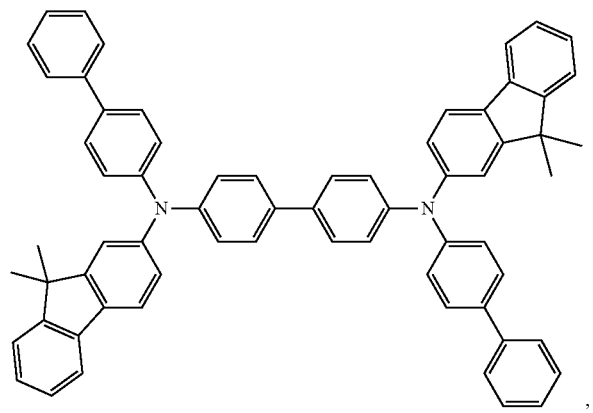
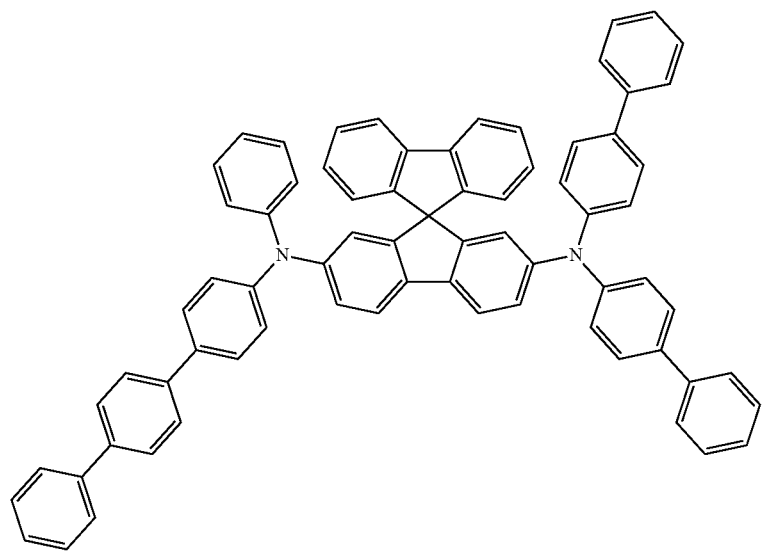

-continued
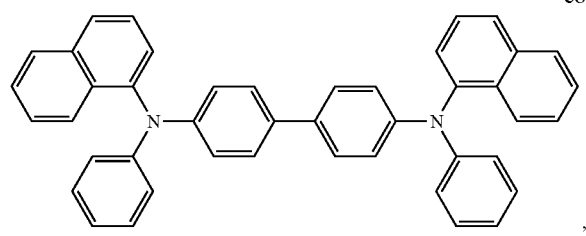
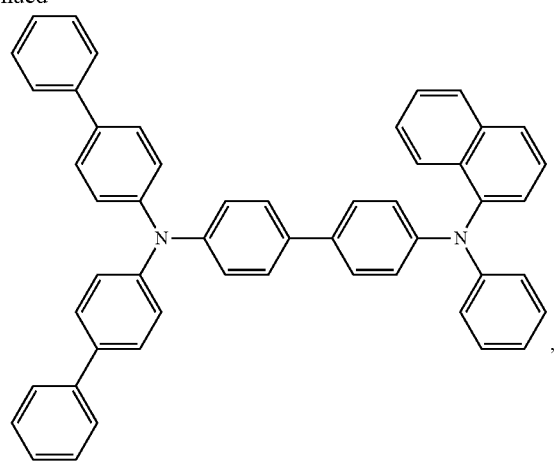
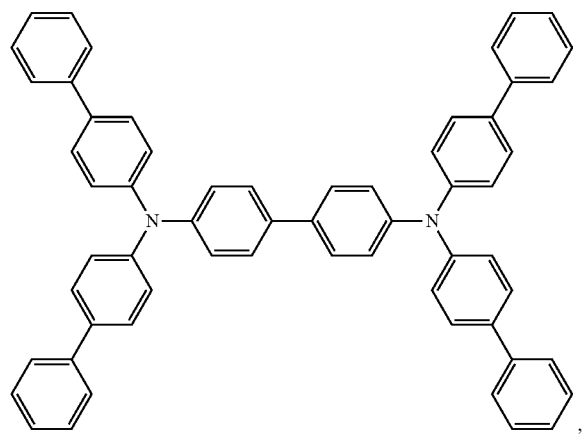
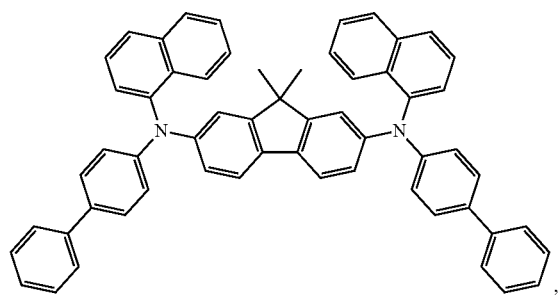
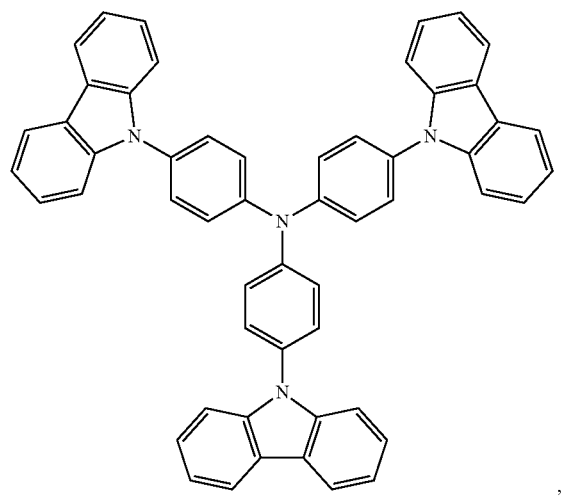
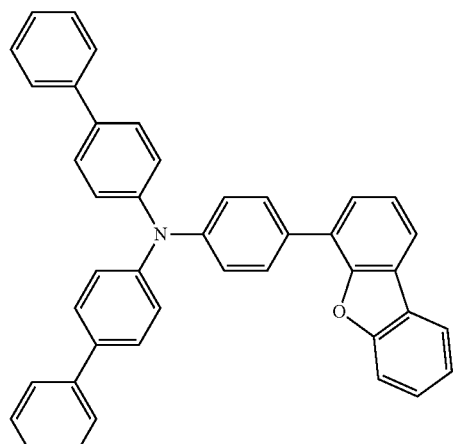

-continued

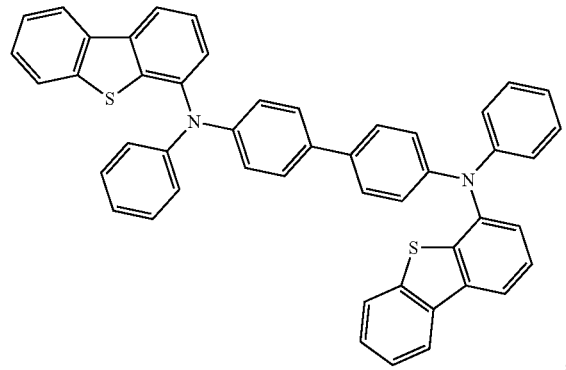

,

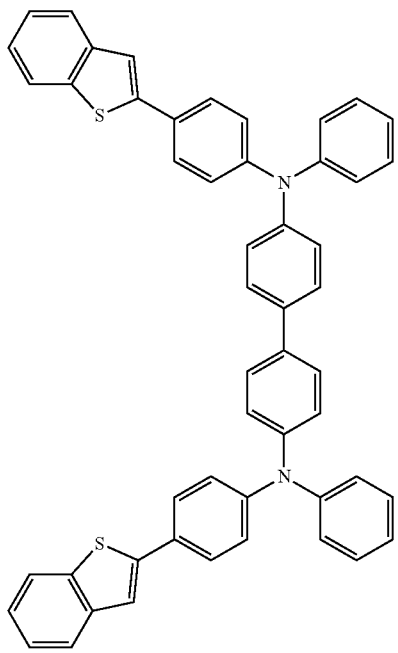

, and

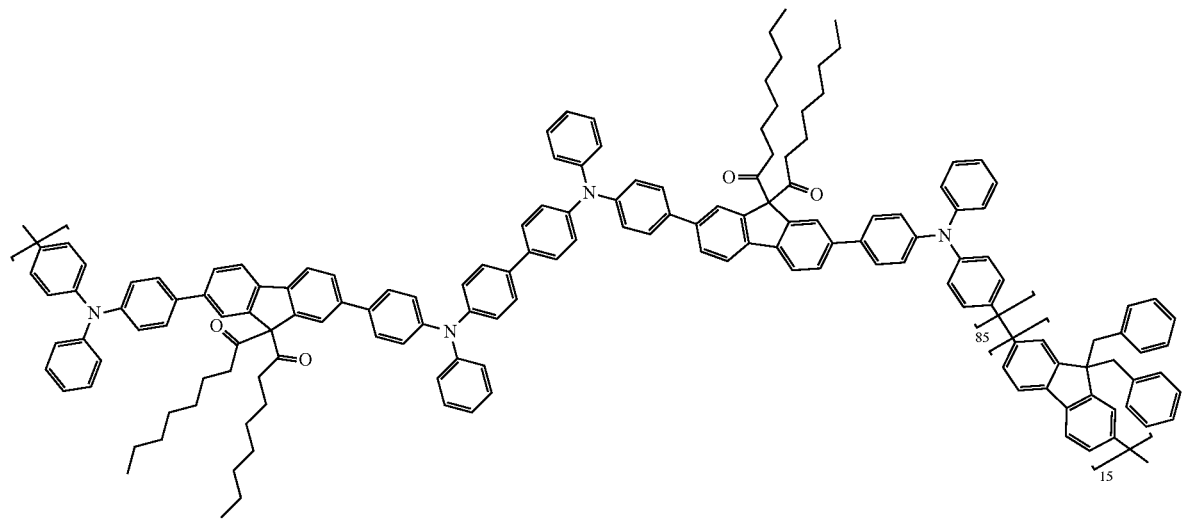

.

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

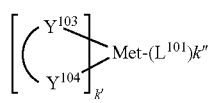

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

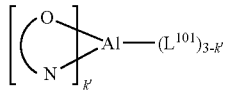 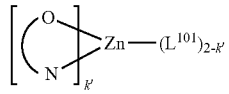

wherein (O—N) is a bidentate ligand, having metal coordinated to atoms O and N.

In another aspect, Met is selected from Ir and Pt. In a further aspect, ($Y^{103}$-$Y^{104}$) is a carbene ligand.

In one aspect, the host compound contains at least one of the following groups selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, the host compound contains at least one of the following groups in the molecule:

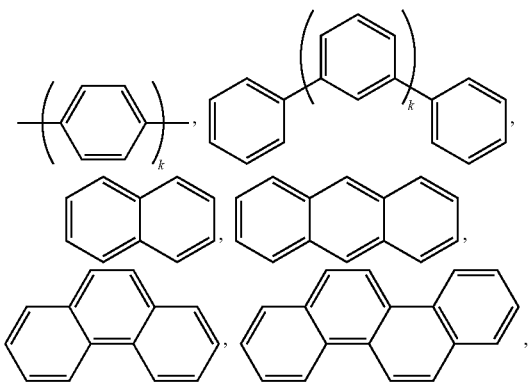

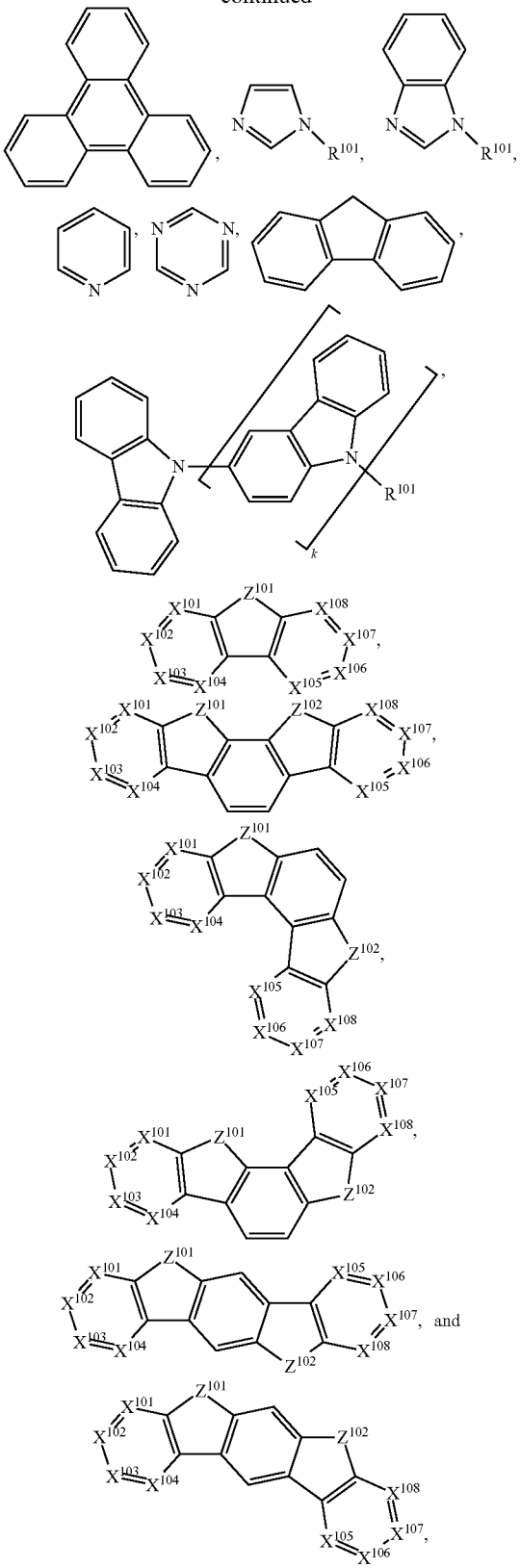

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803,

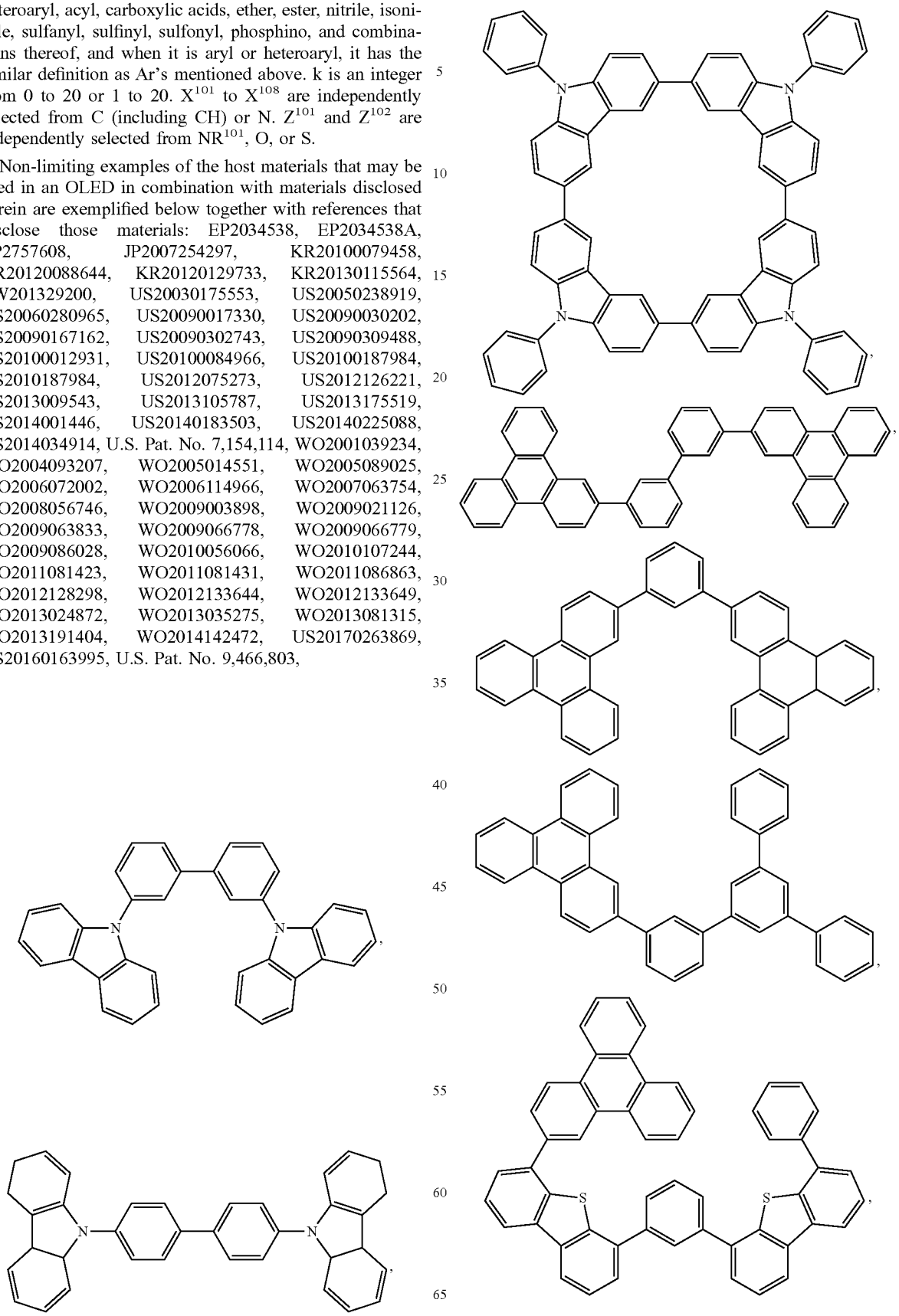

77
-continued
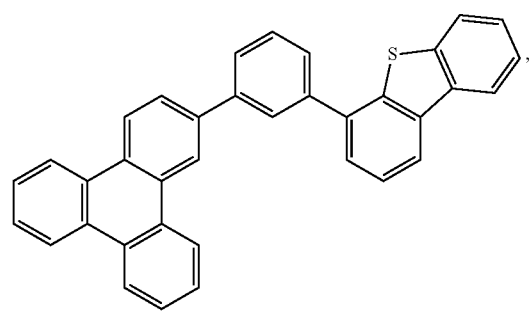
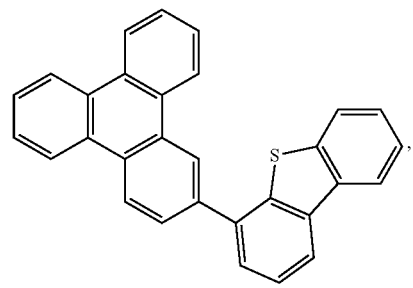
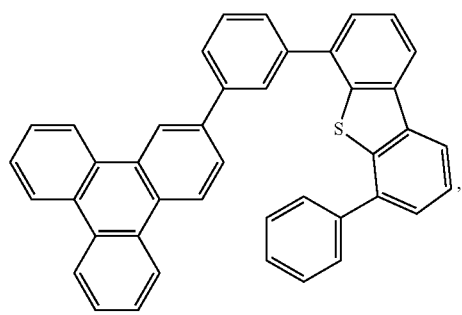
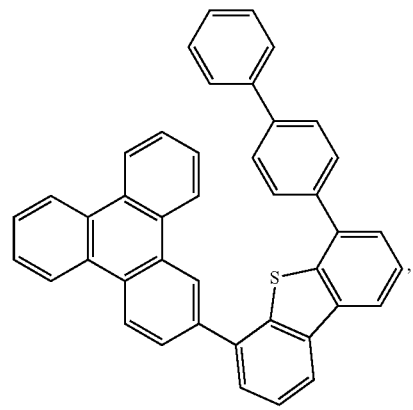
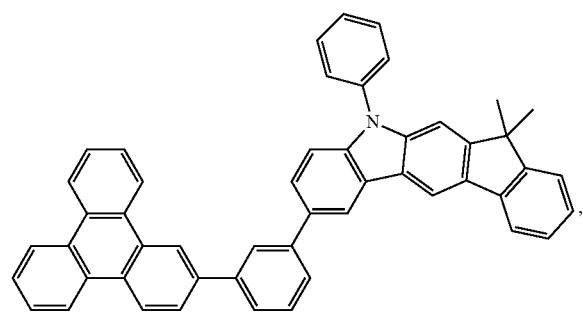
78
-continued
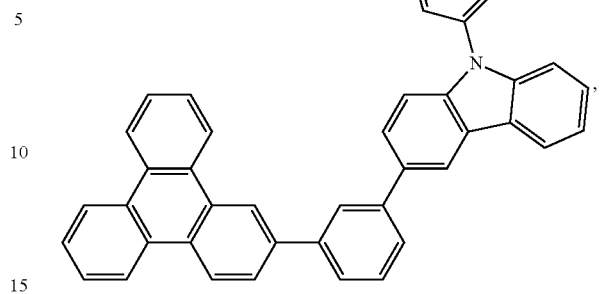
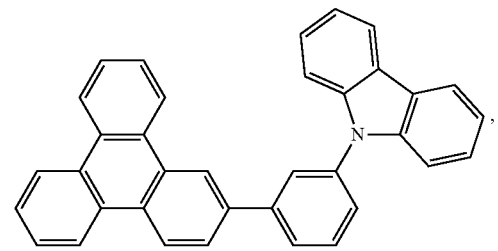
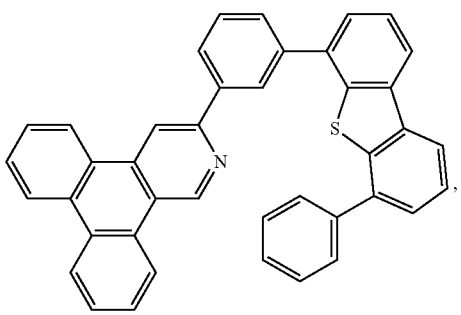
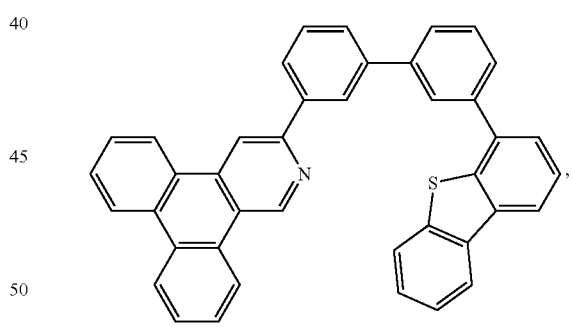
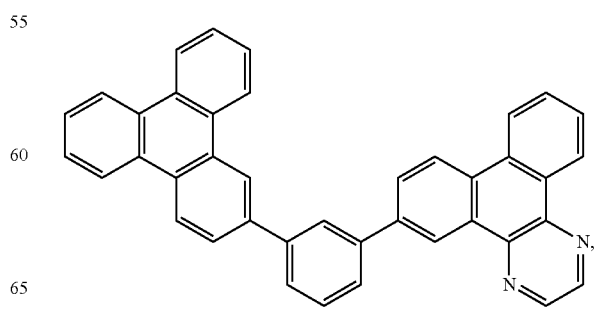

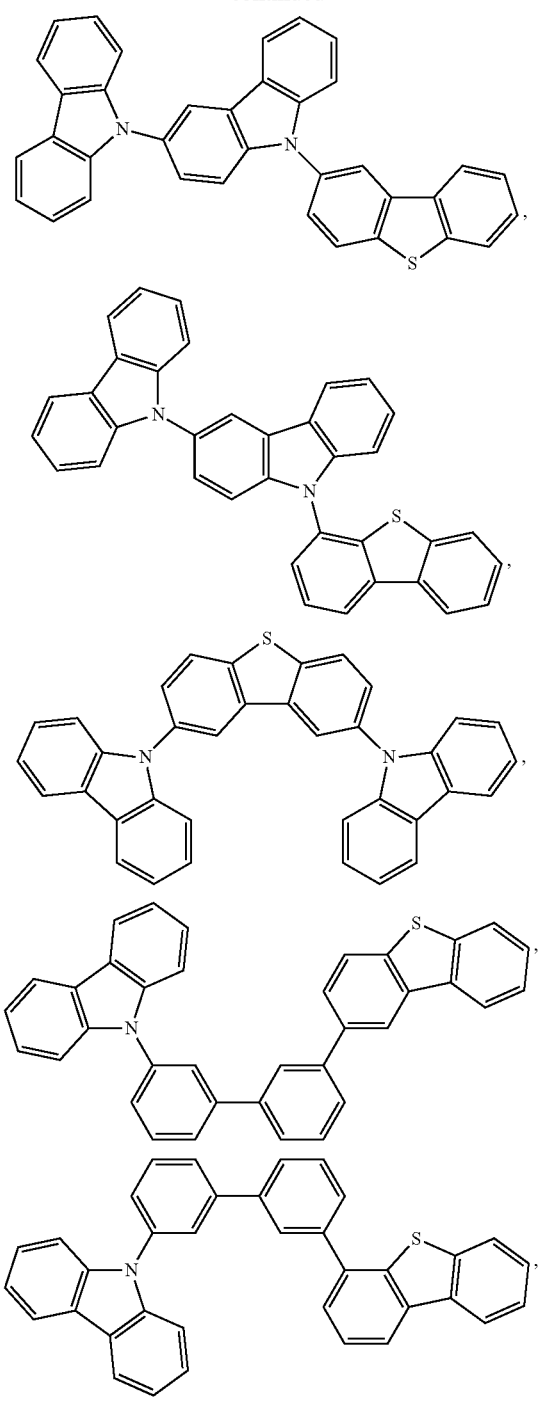
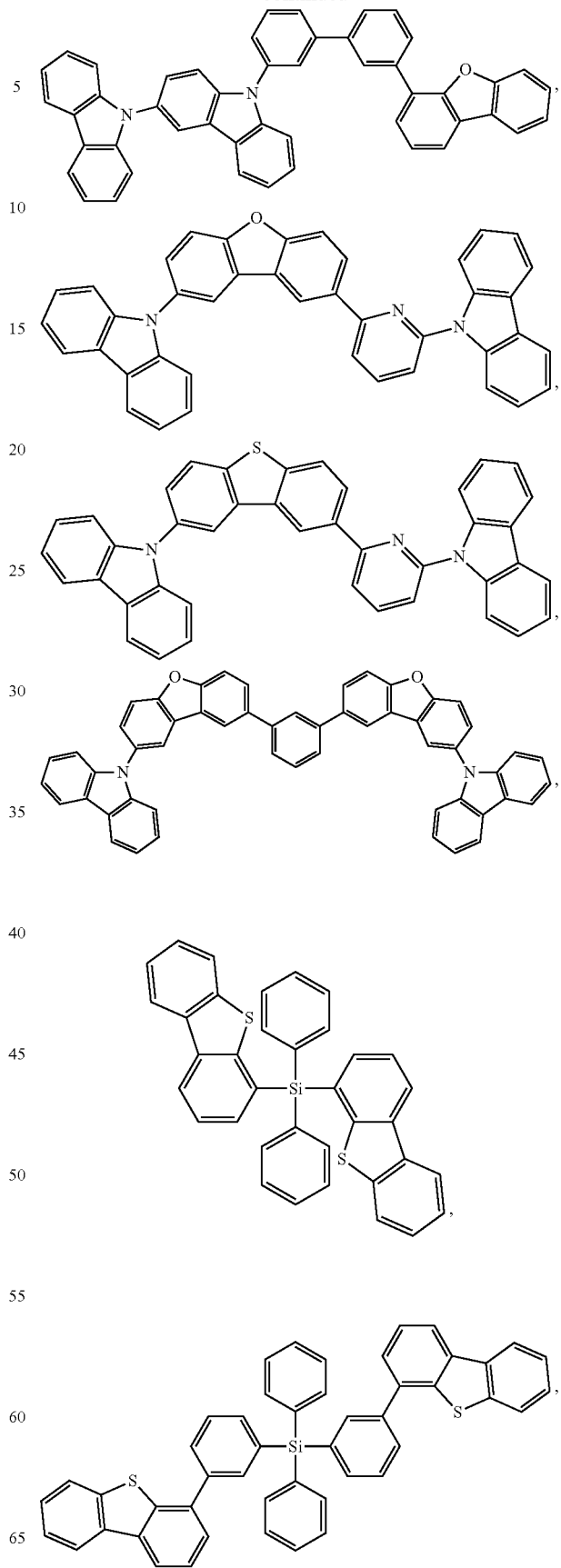

81
-continued
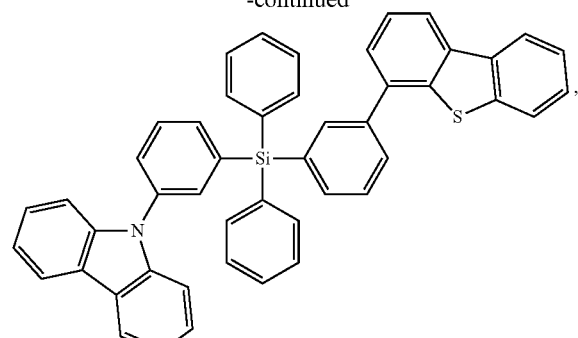
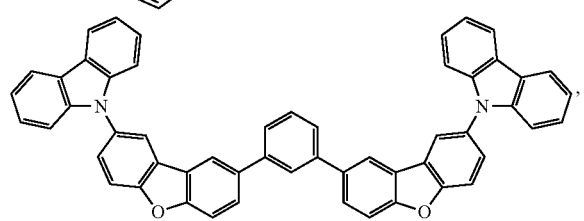
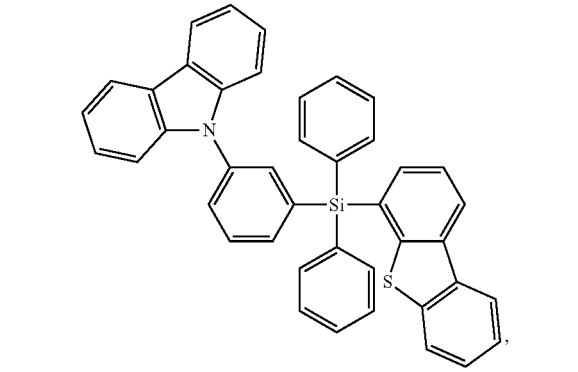
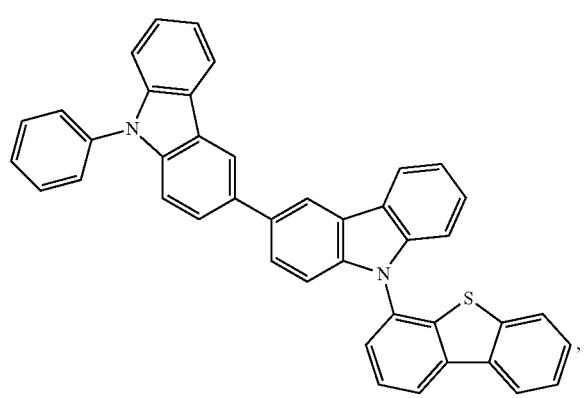
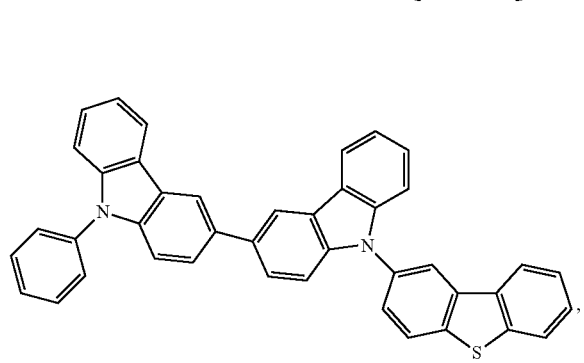
82
-continued
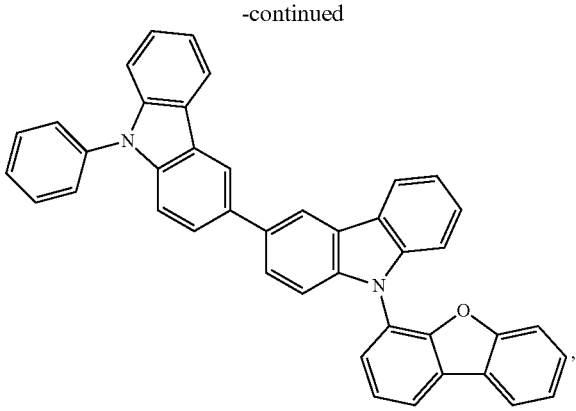
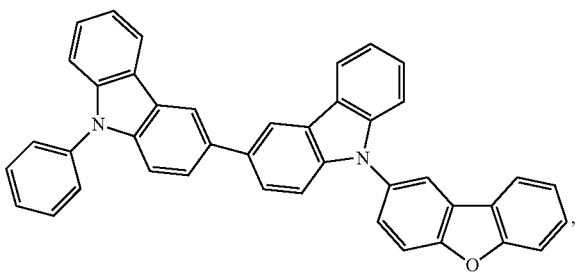
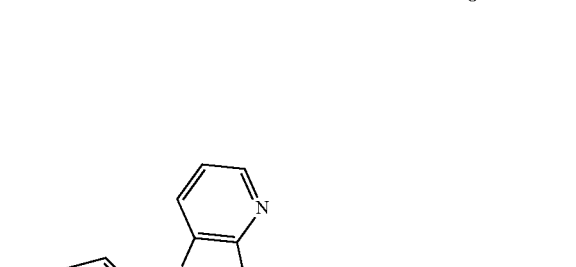
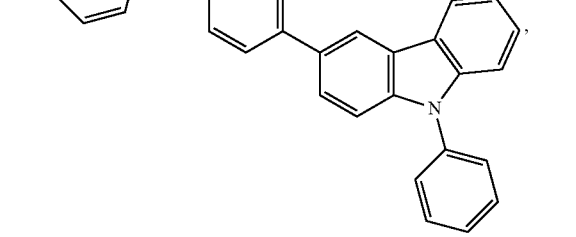
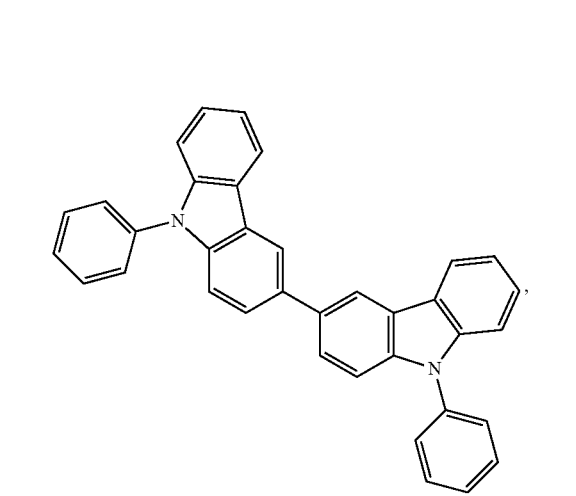

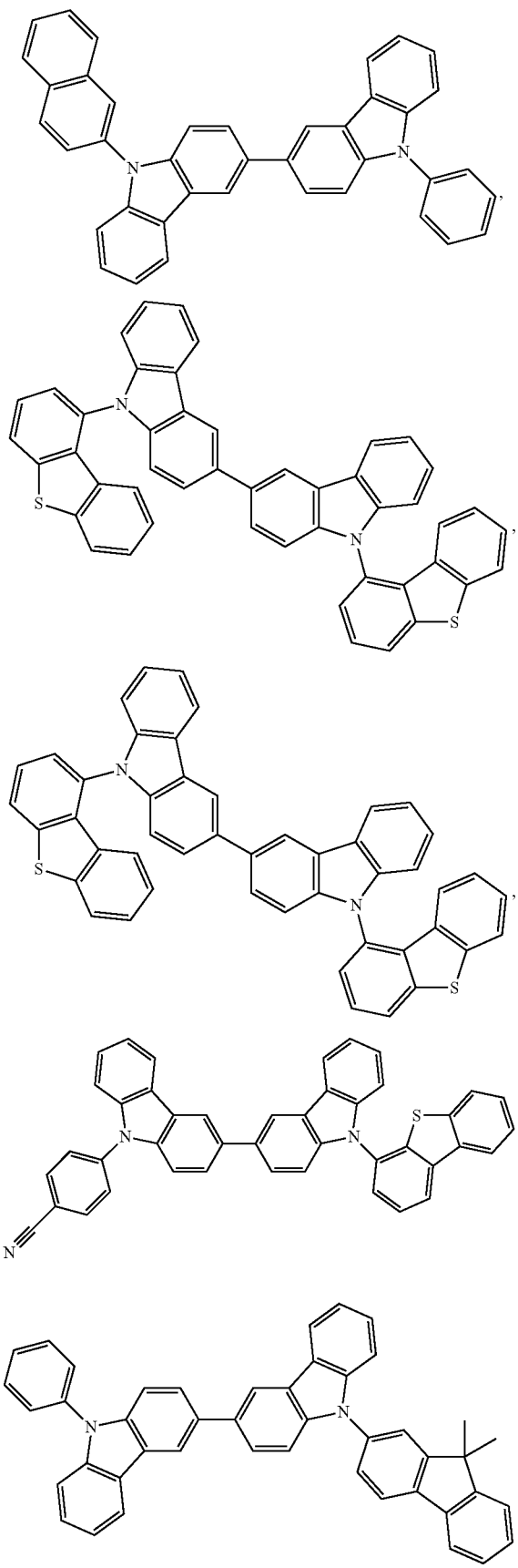
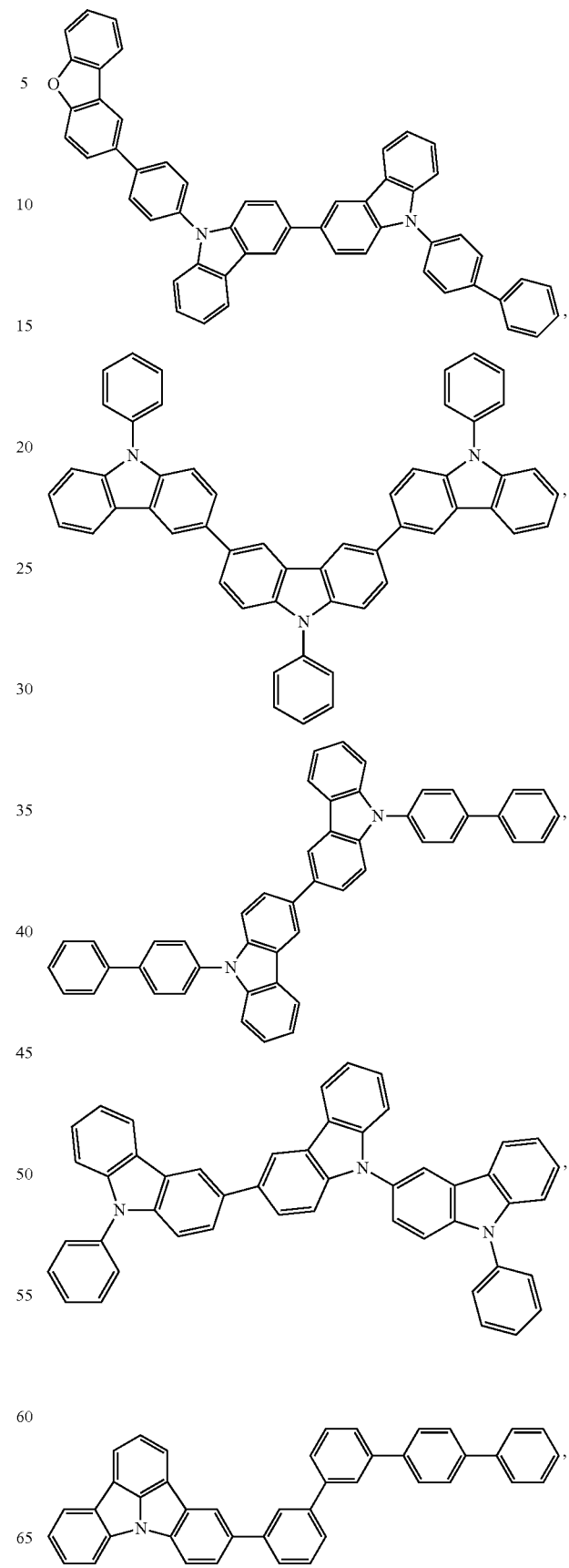

-continued
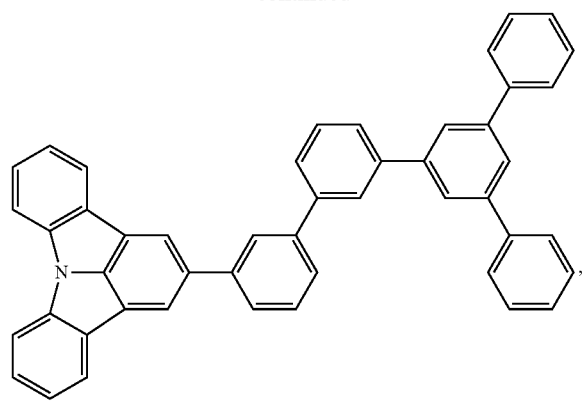
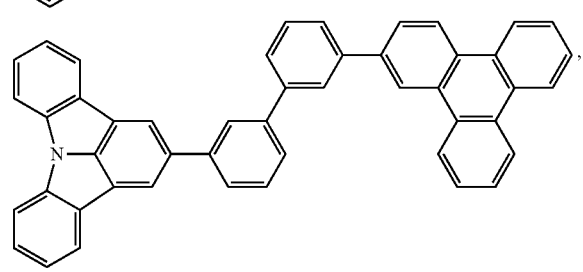
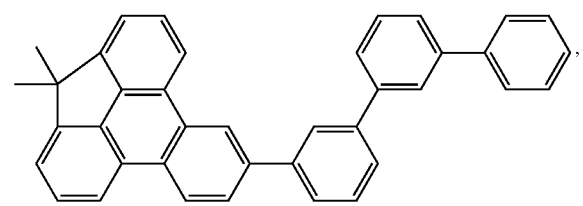
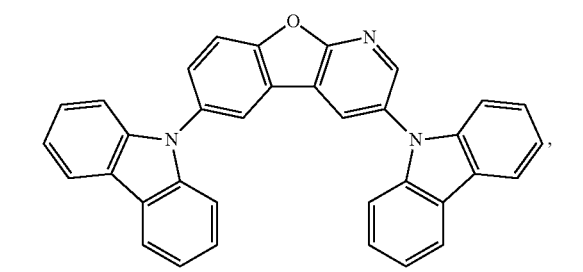
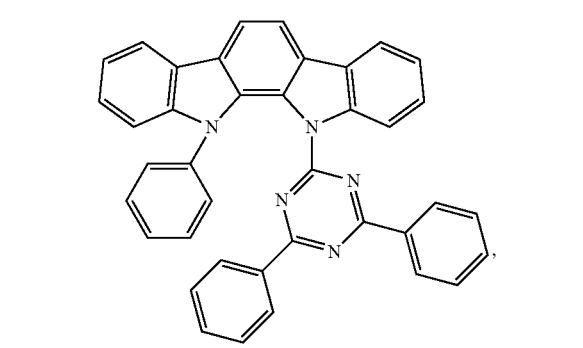
-continued
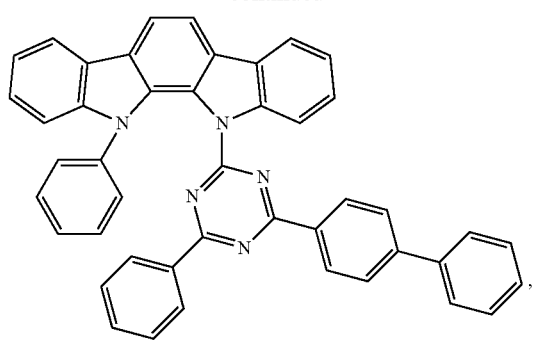
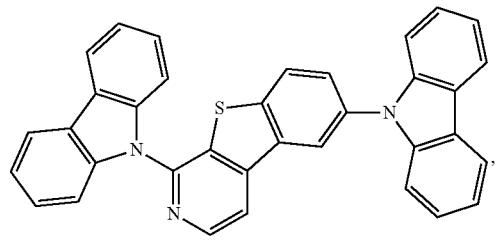
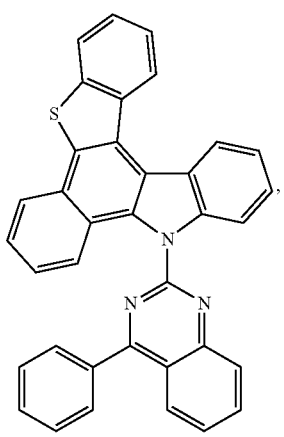
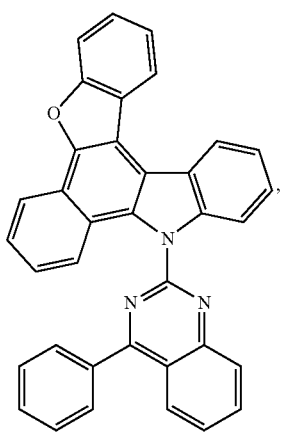

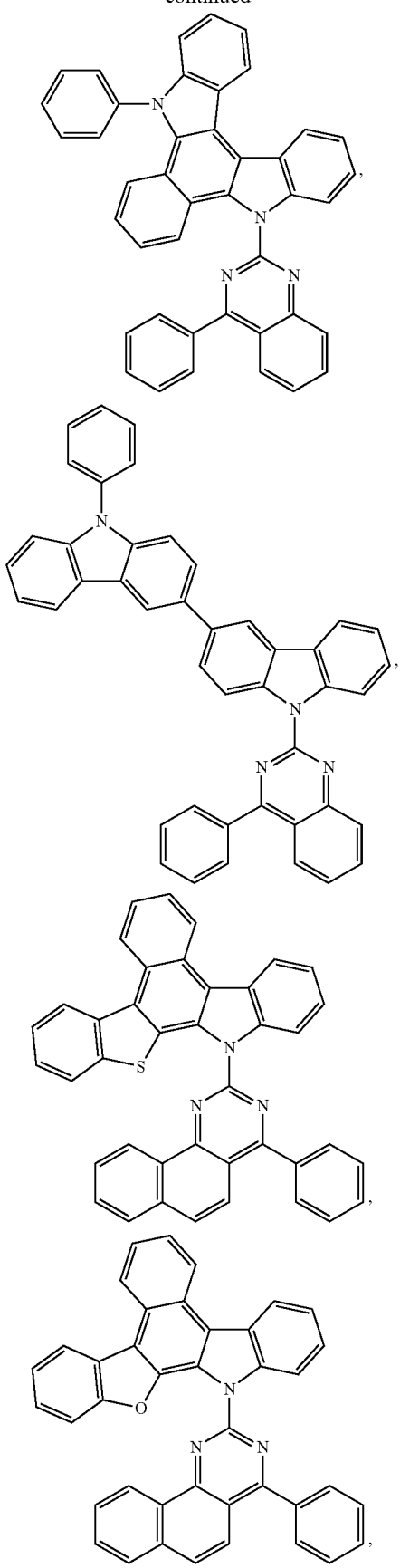
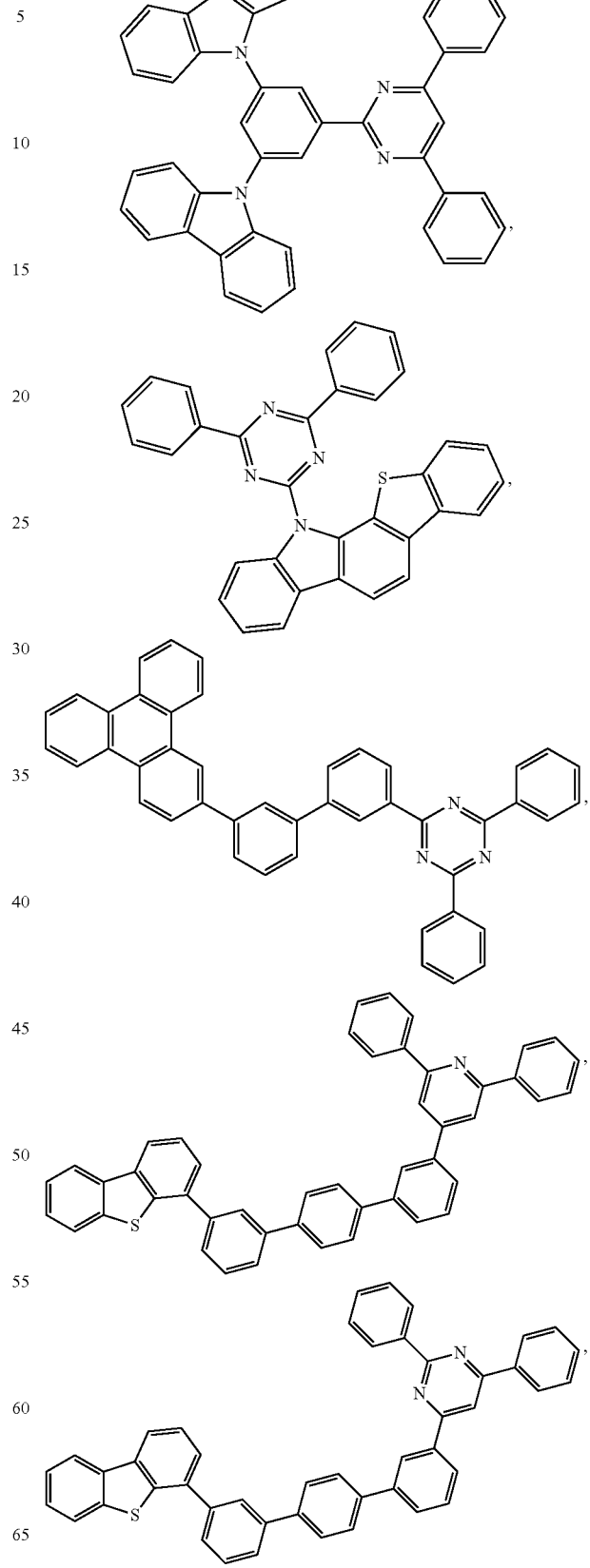

-continued

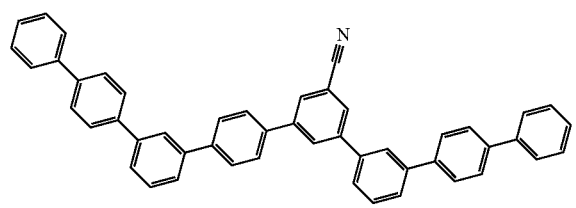,

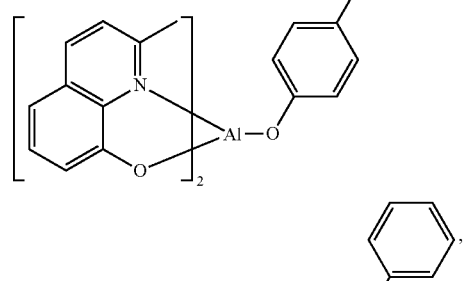,

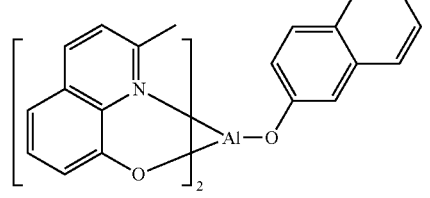,

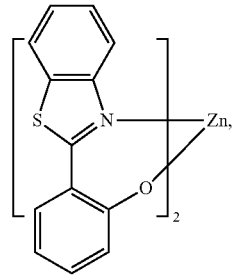,

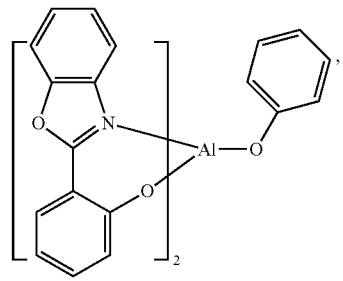,

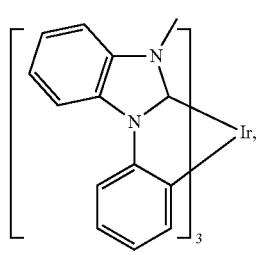,

-continued

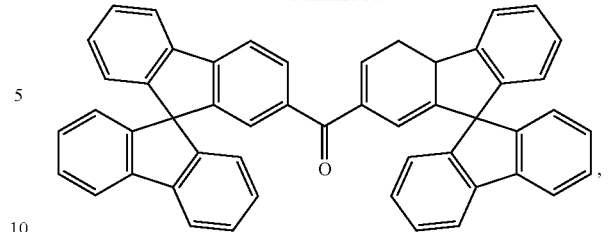,

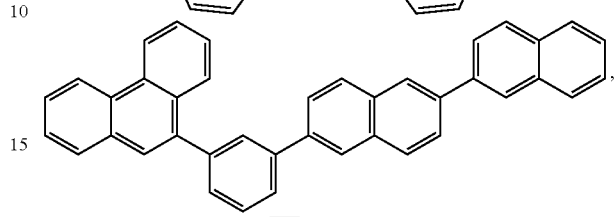,

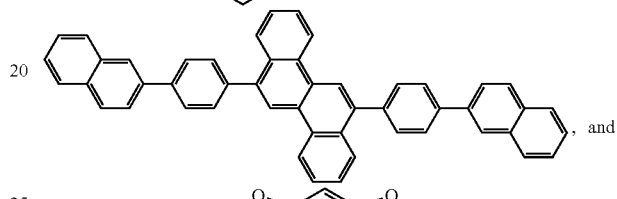, and

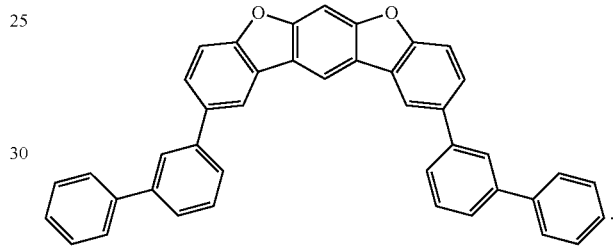.

Additional Emitters:

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, US06699599, US06916554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.
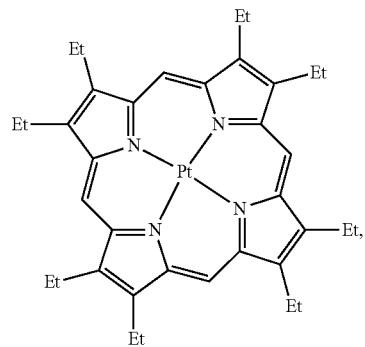
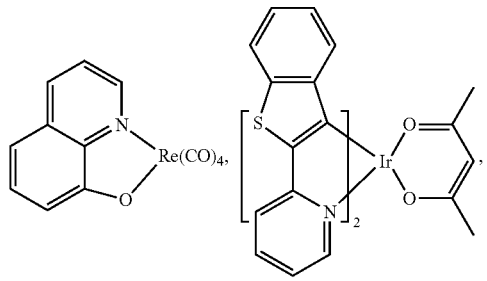
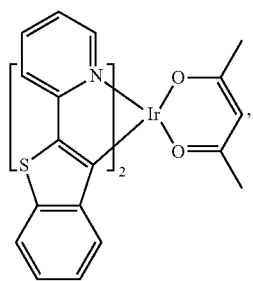
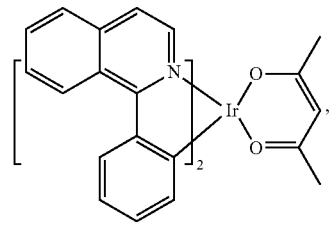
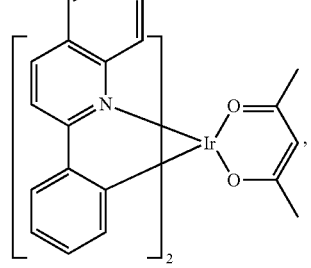
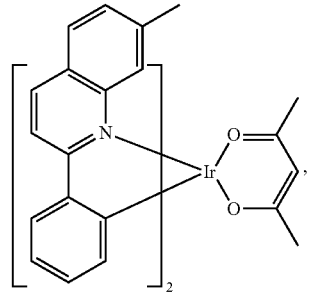
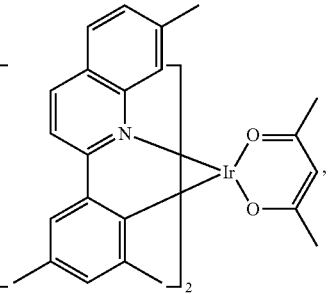
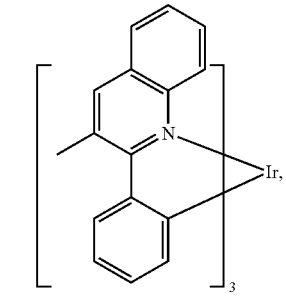
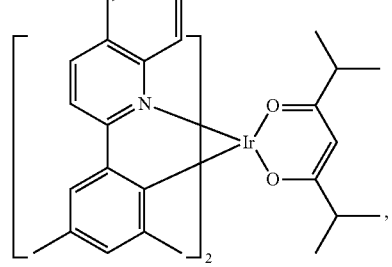

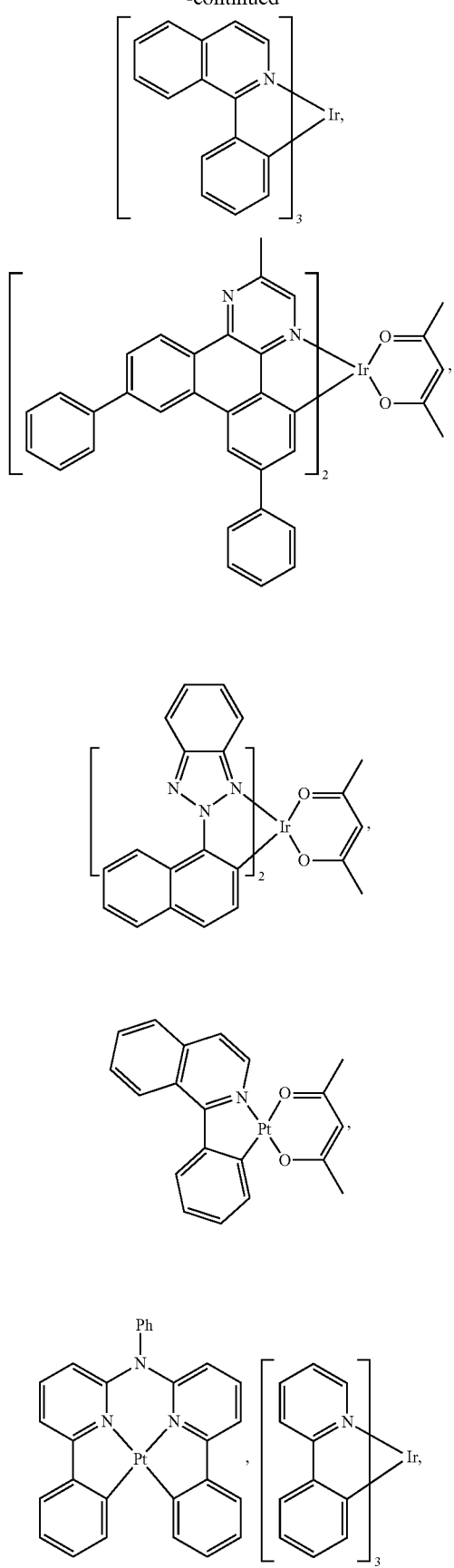
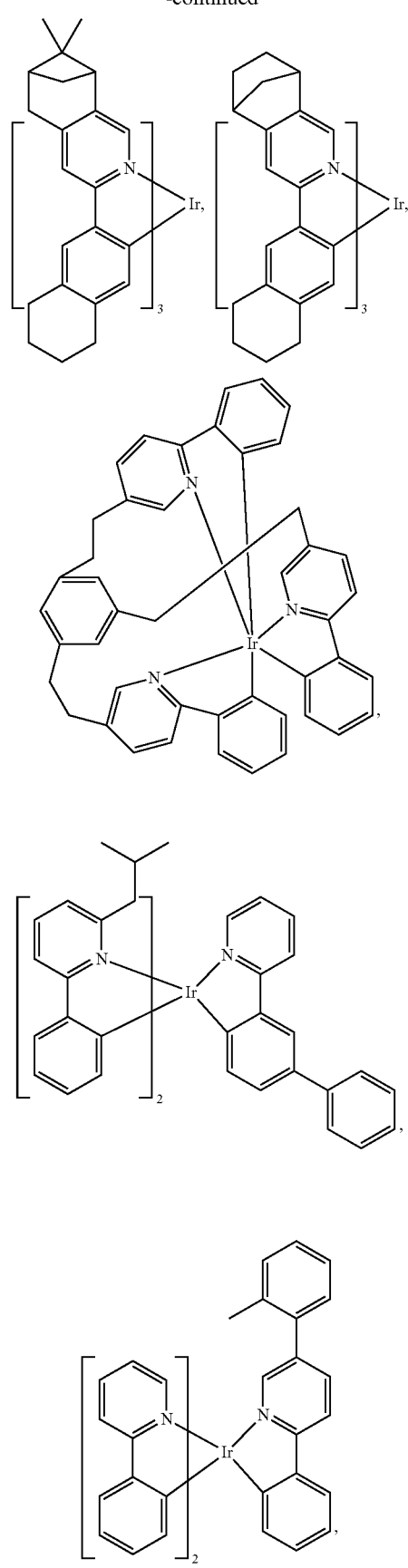

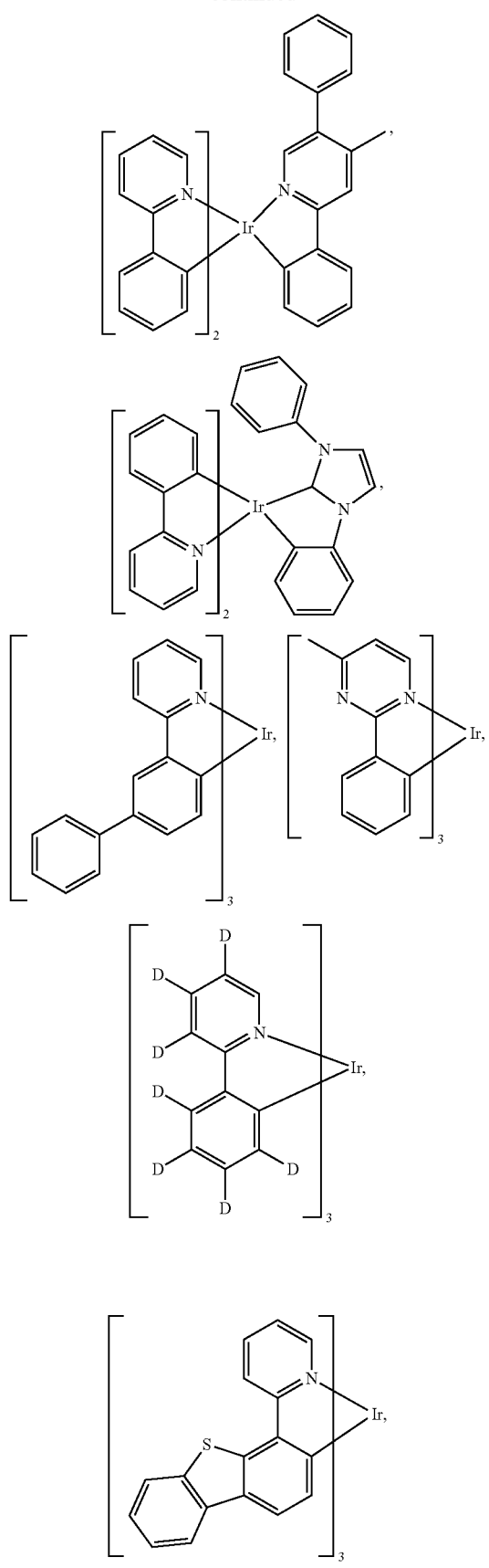
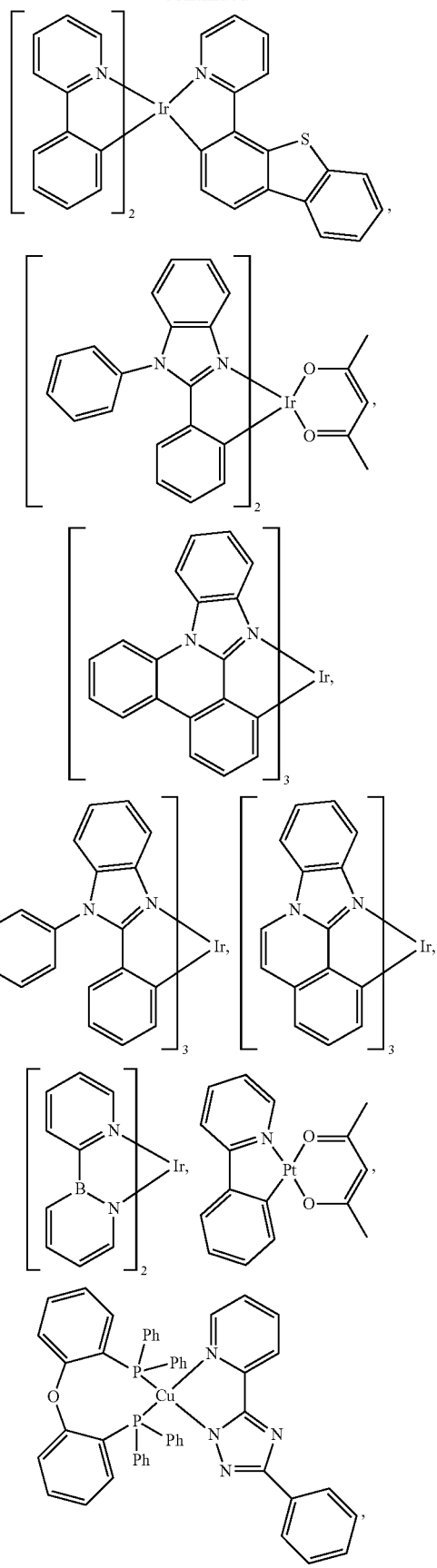

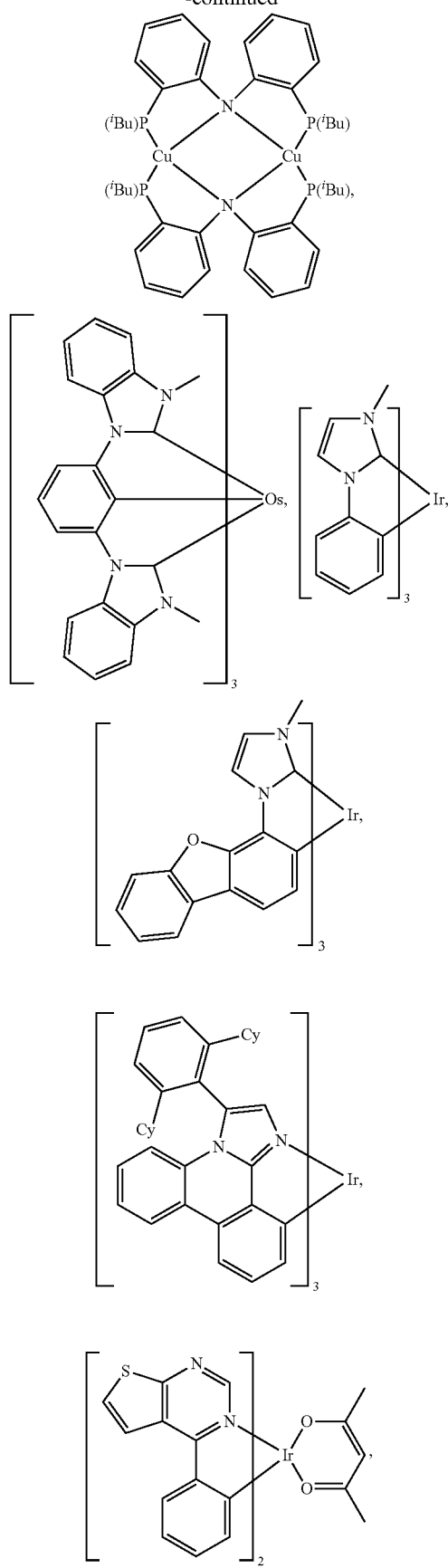

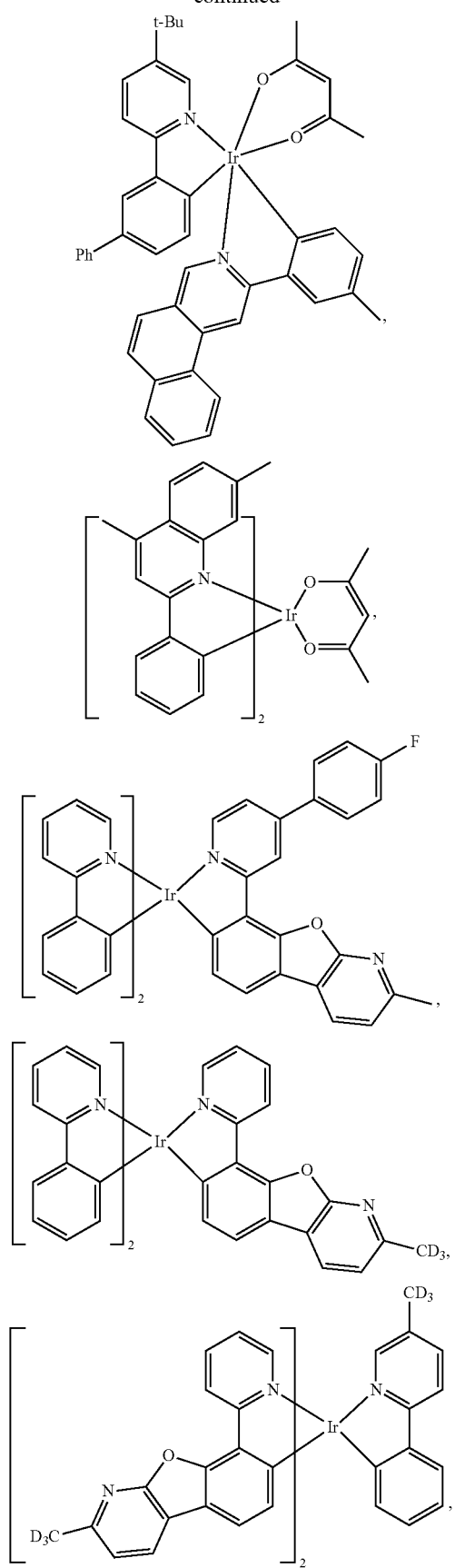
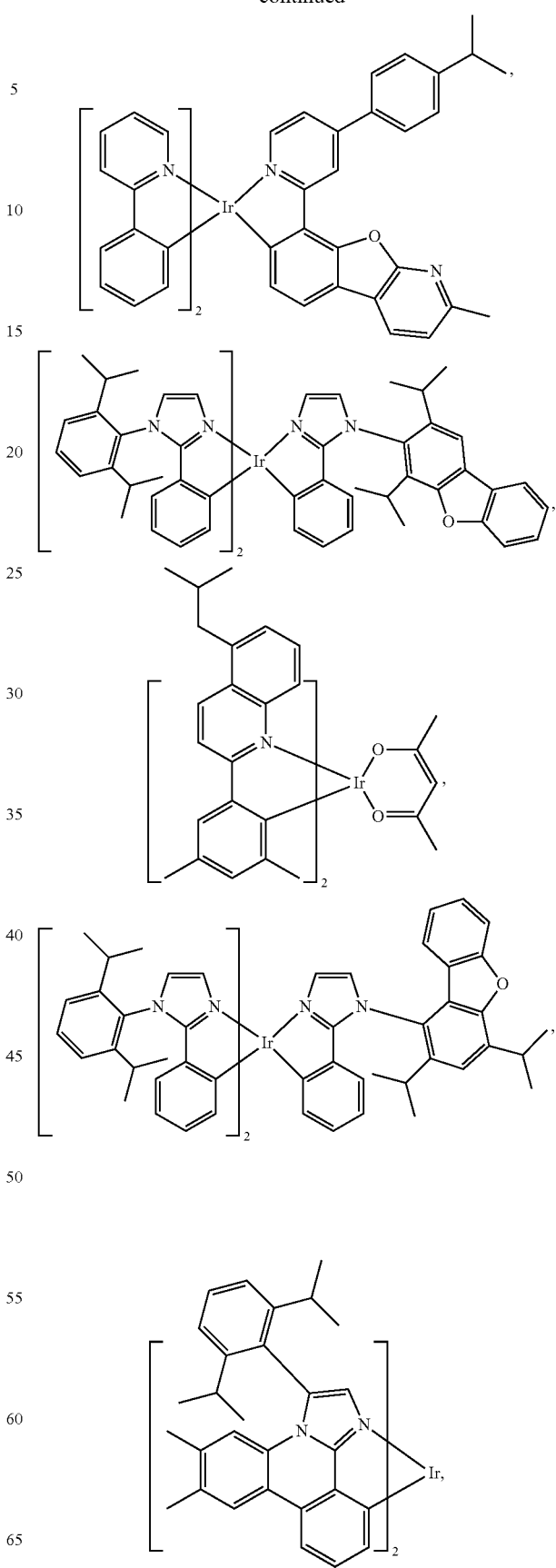

101
-continued
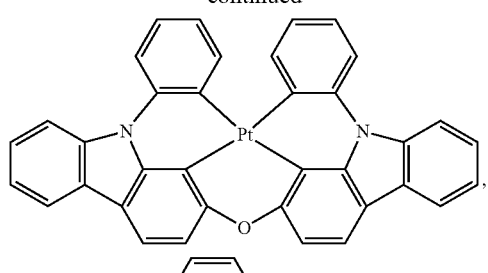
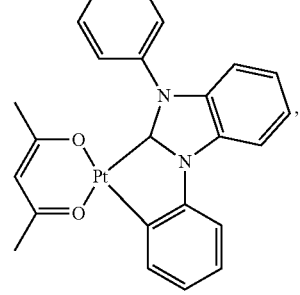
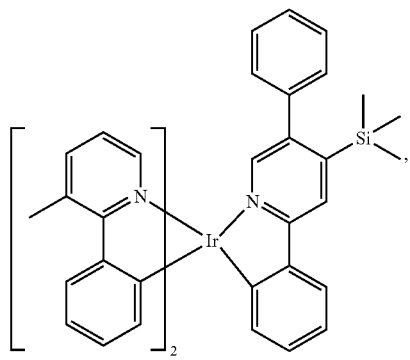
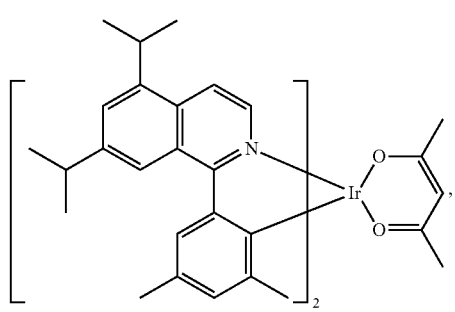
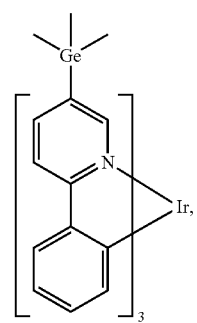
102
-continued
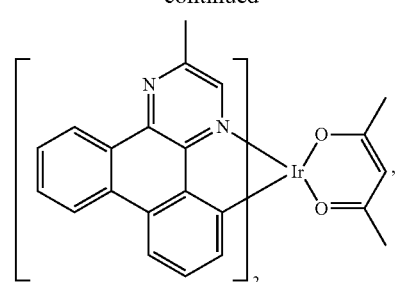
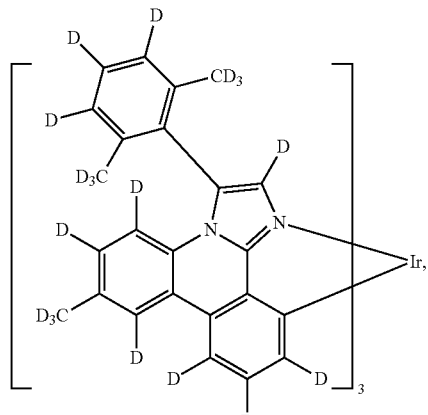
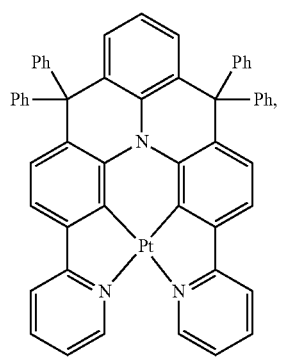
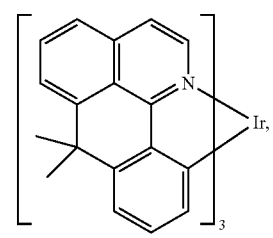
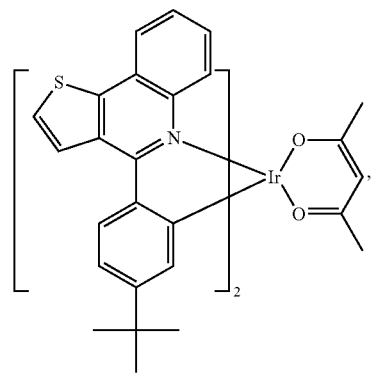

103
-continued
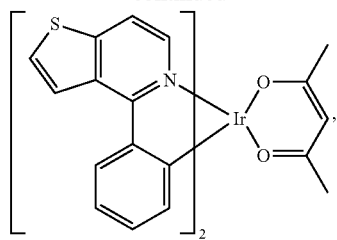
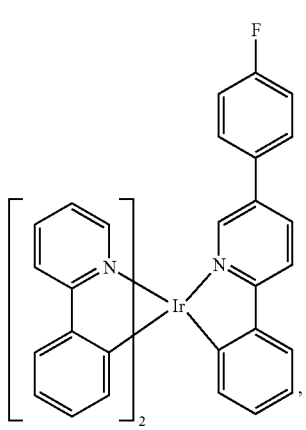
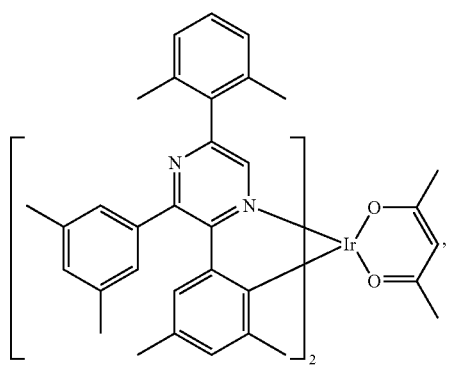
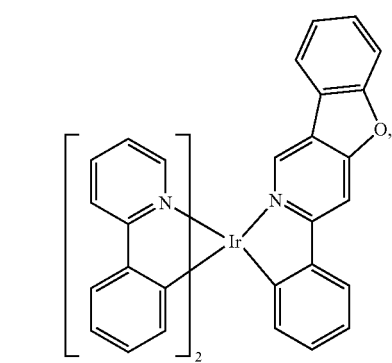
104
-continued
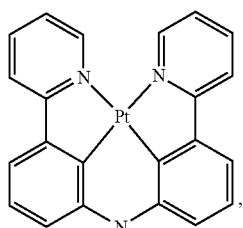
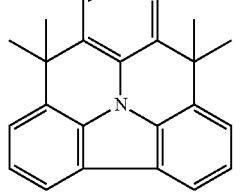
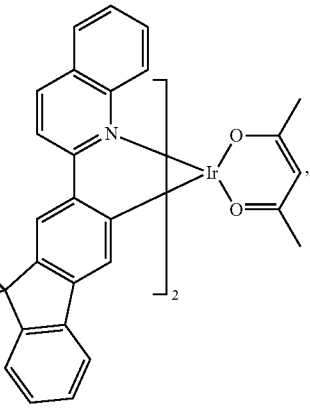
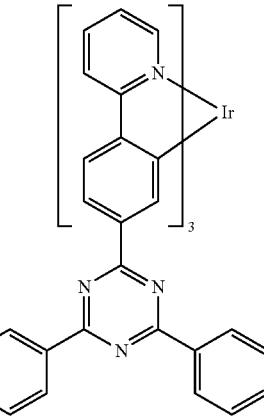
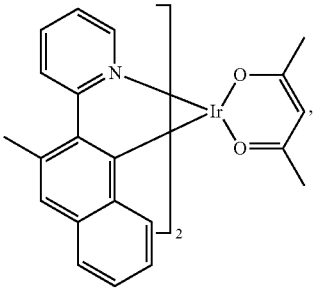

105
-continued
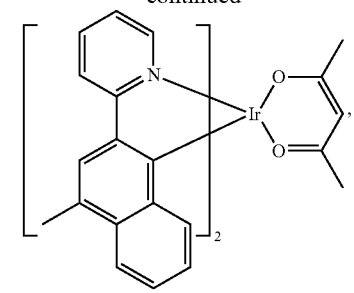
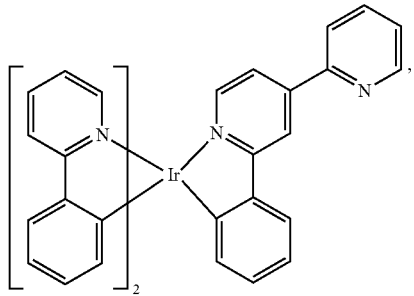
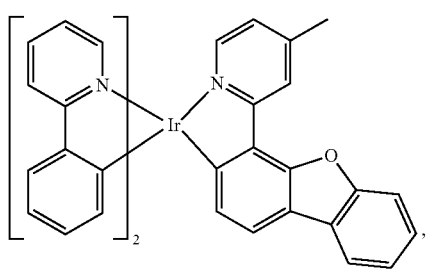
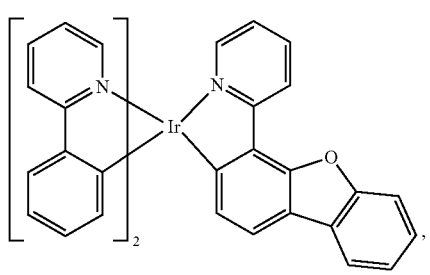
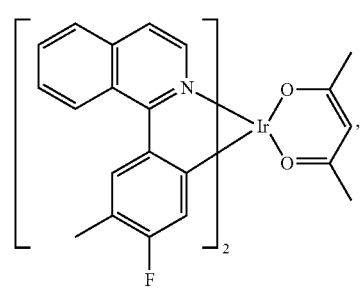
106
-continued
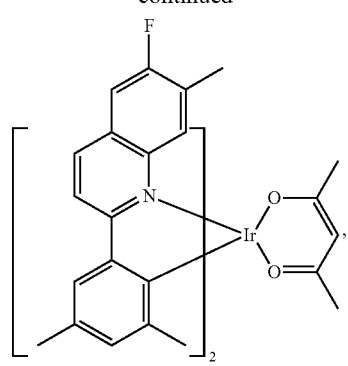
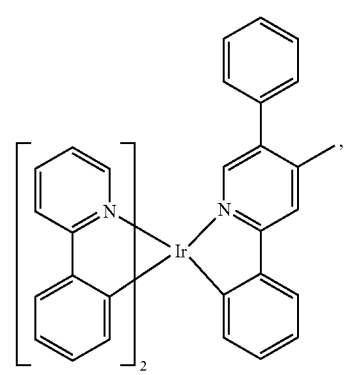
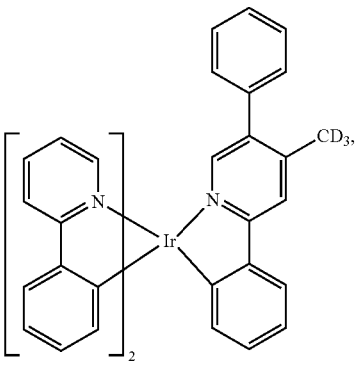
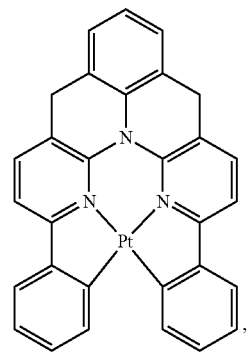

107
-continued
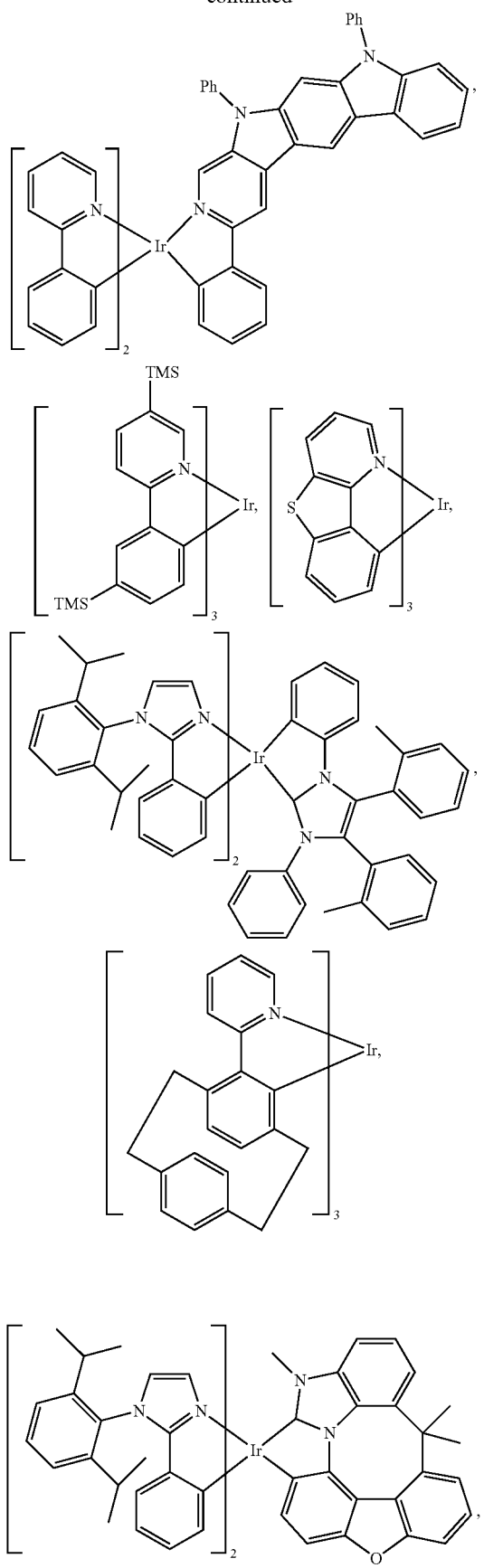
108
-continued
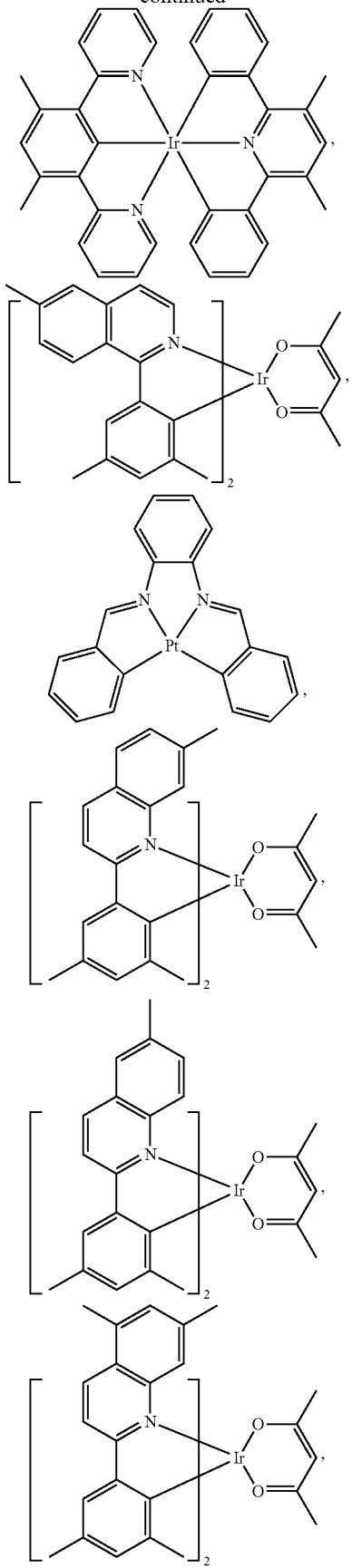

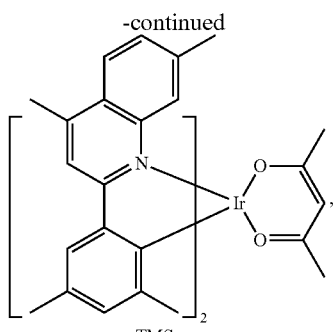
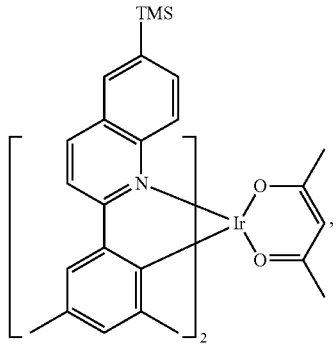
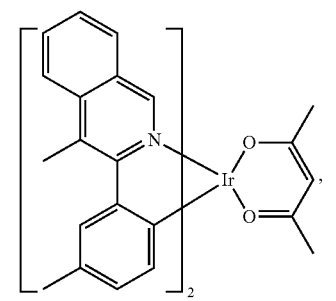
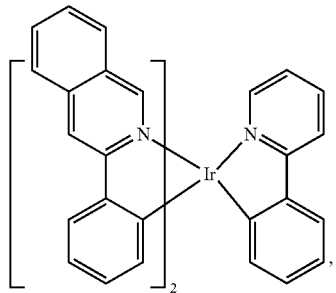
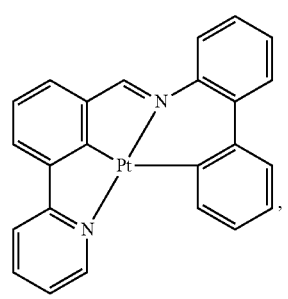
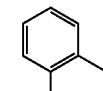
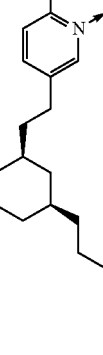
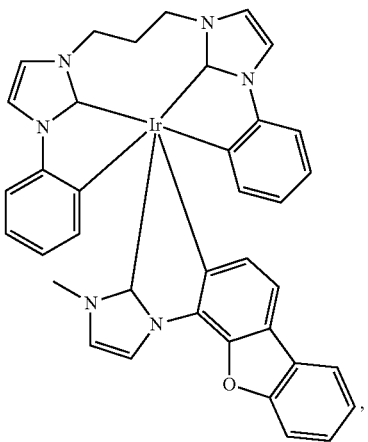
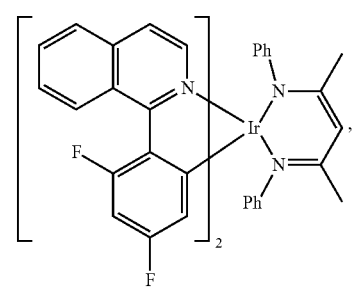
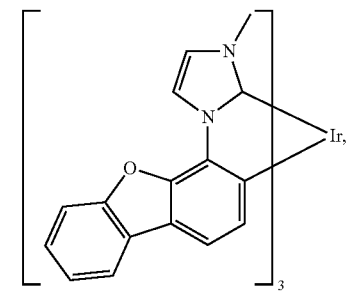

111
-continued
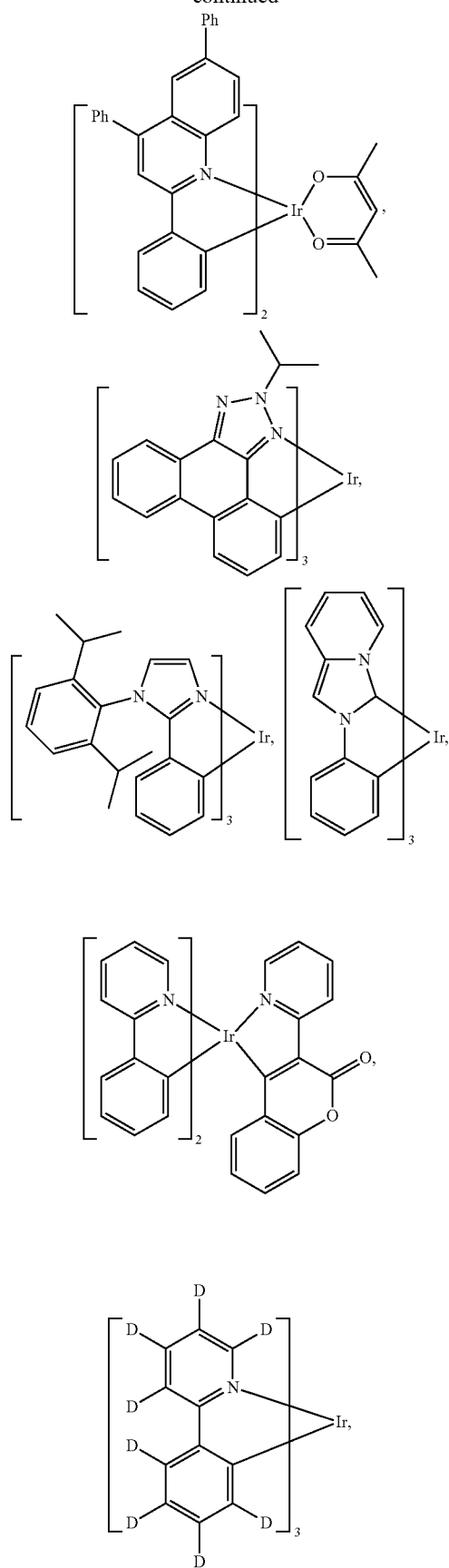
112
-continued
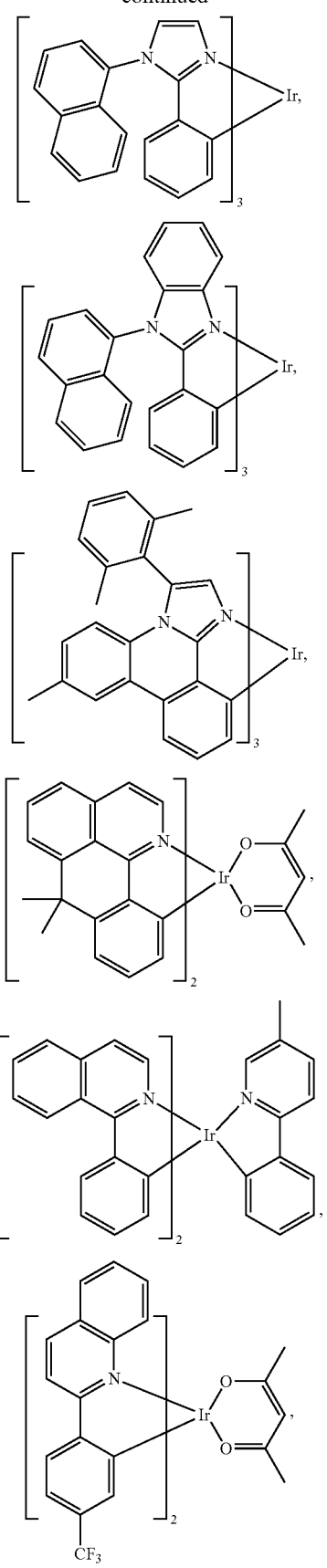

-continued

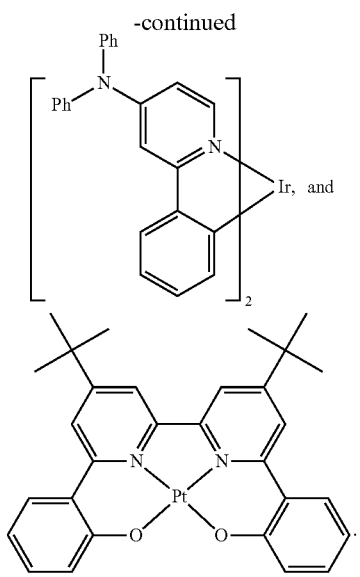

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

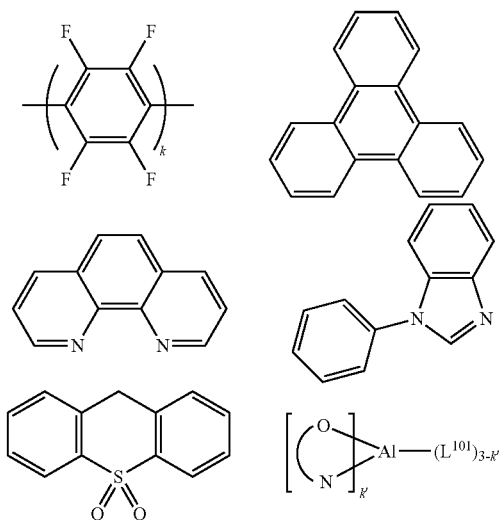

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

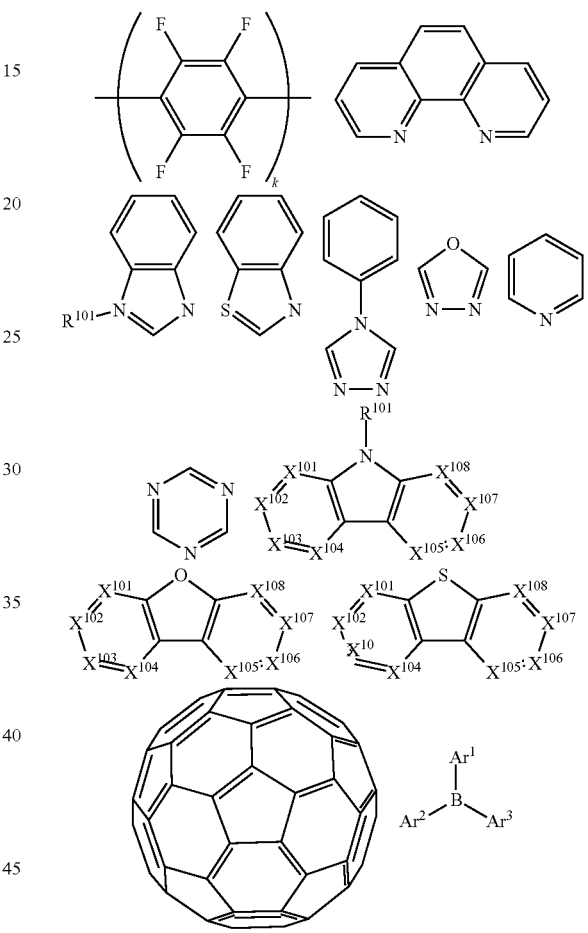

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

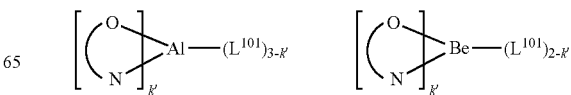

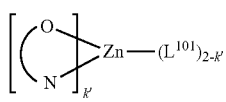 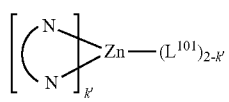

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-22334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

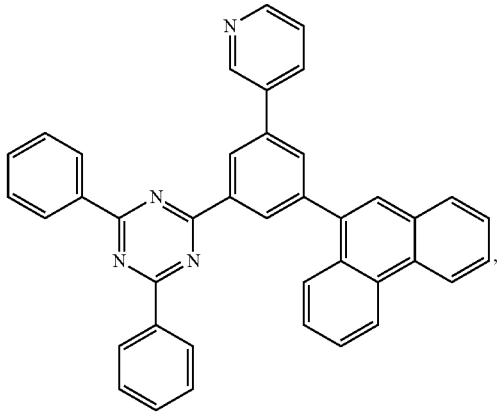

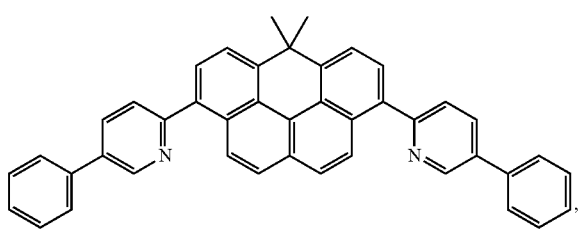

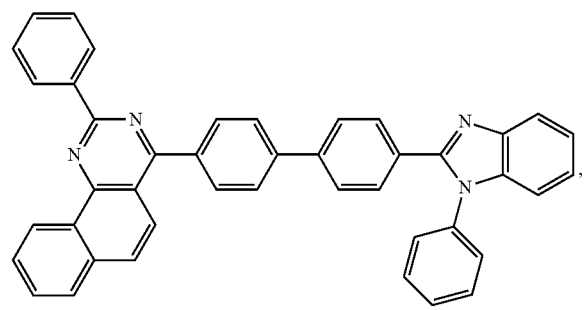

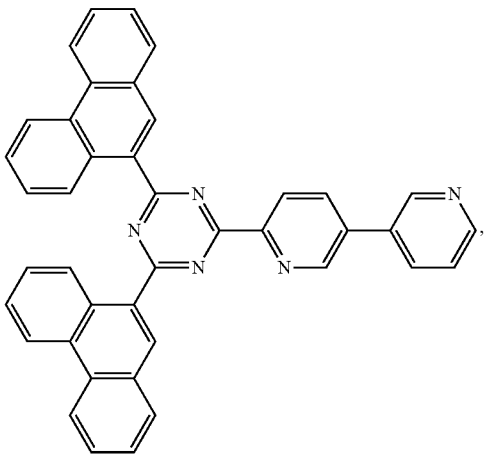

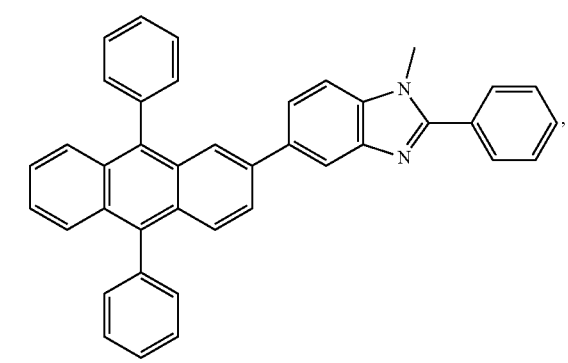

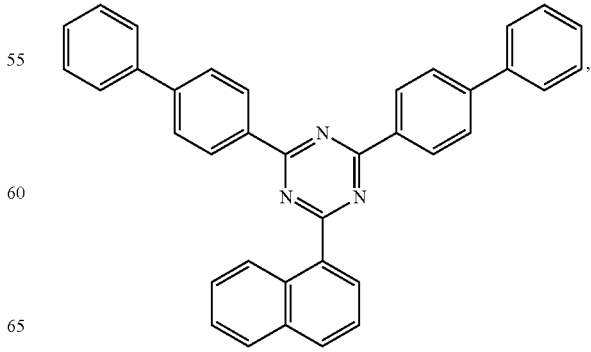

117
-continued
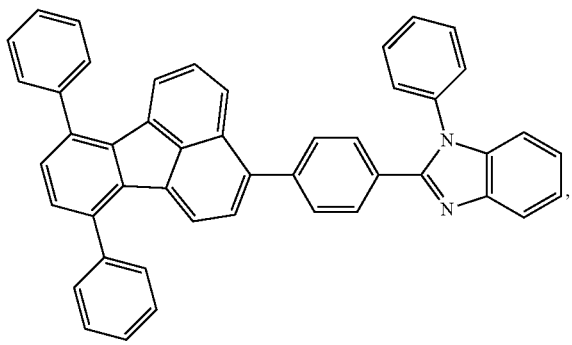
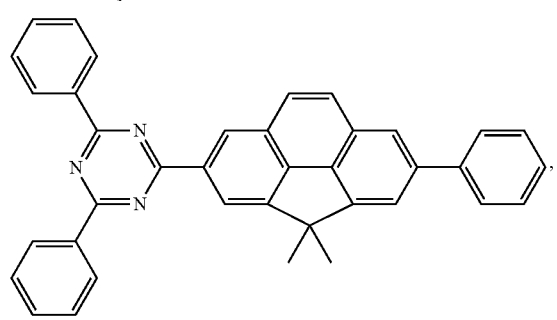
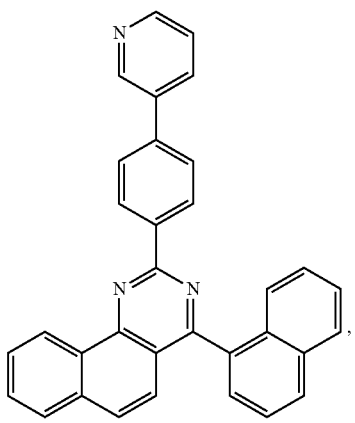
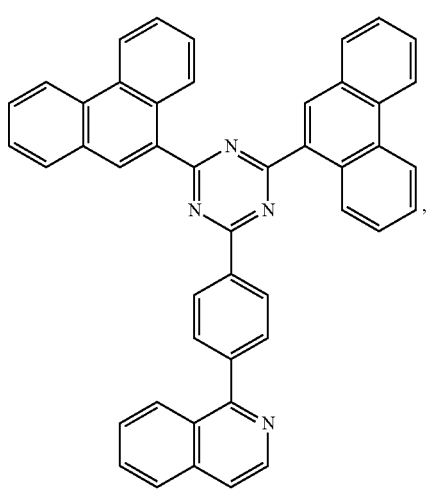
118
-continued
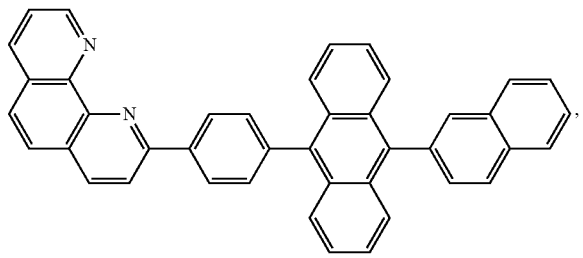
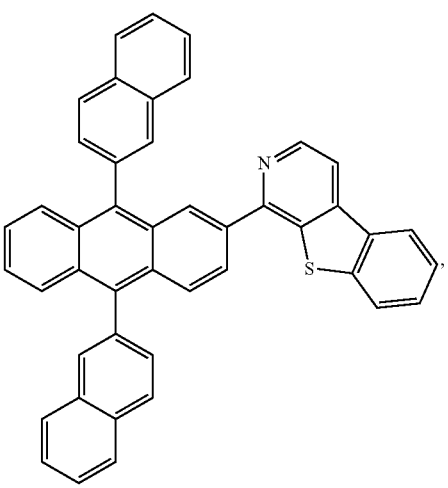
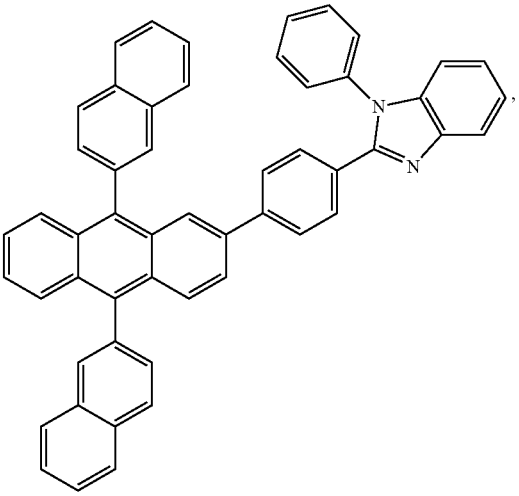
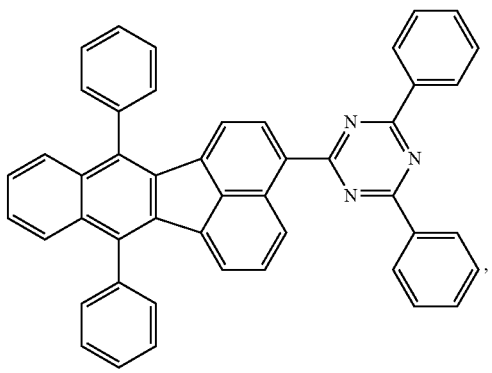

119
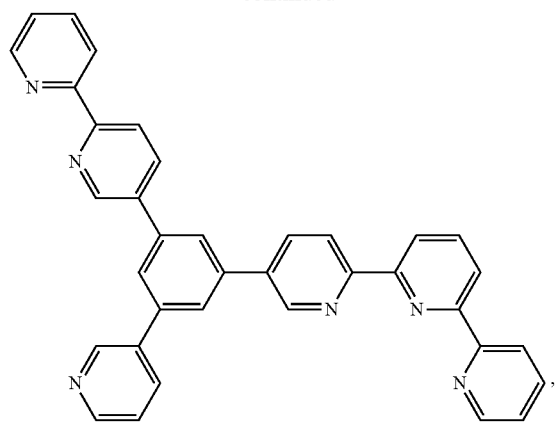
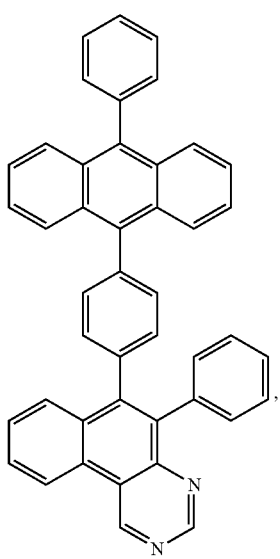
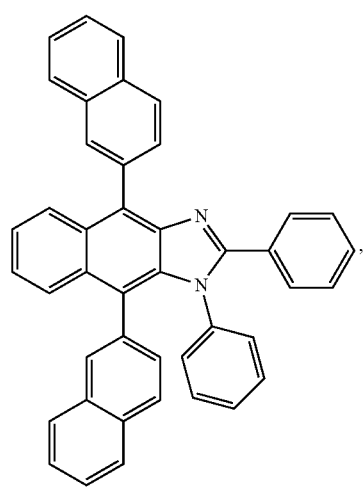
120
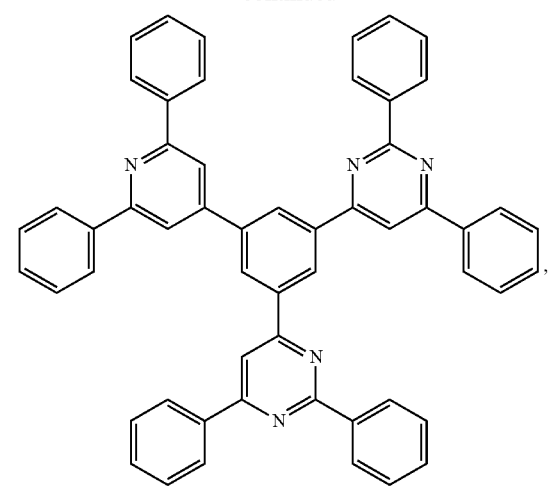
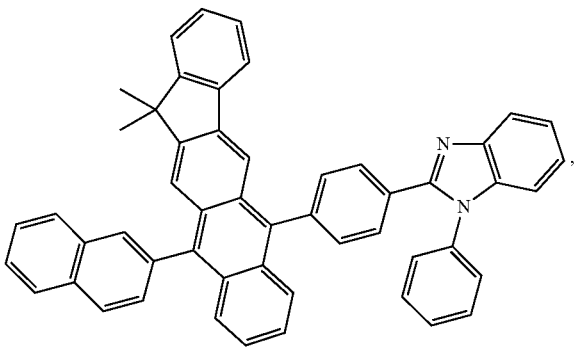

121
-continued
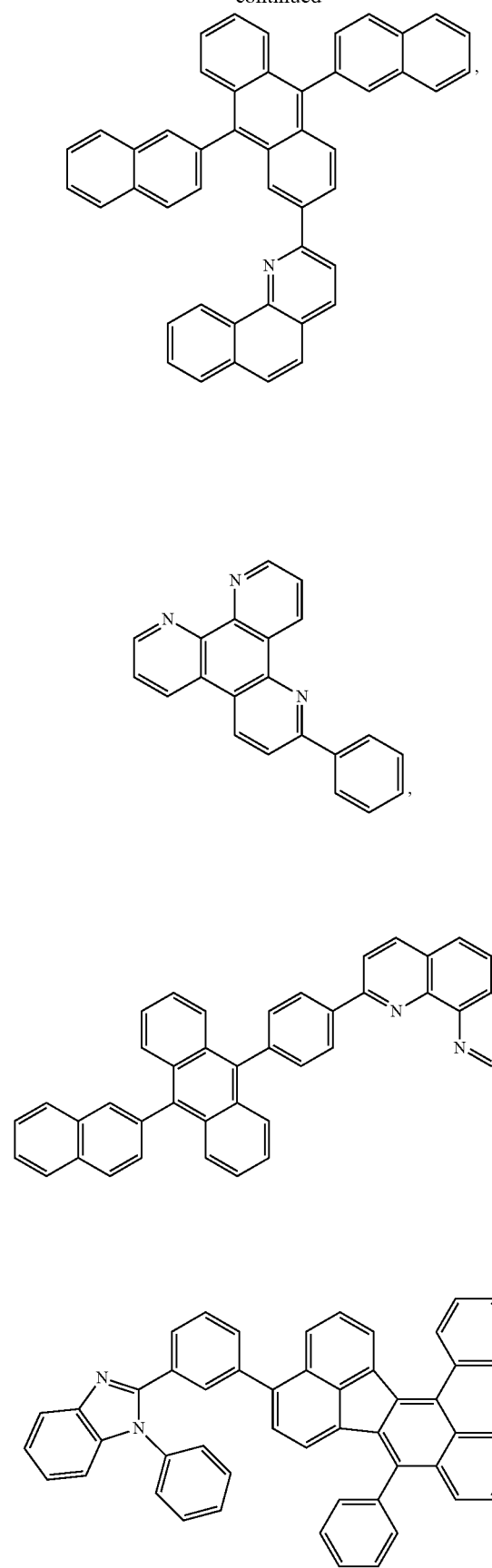
122
-continued
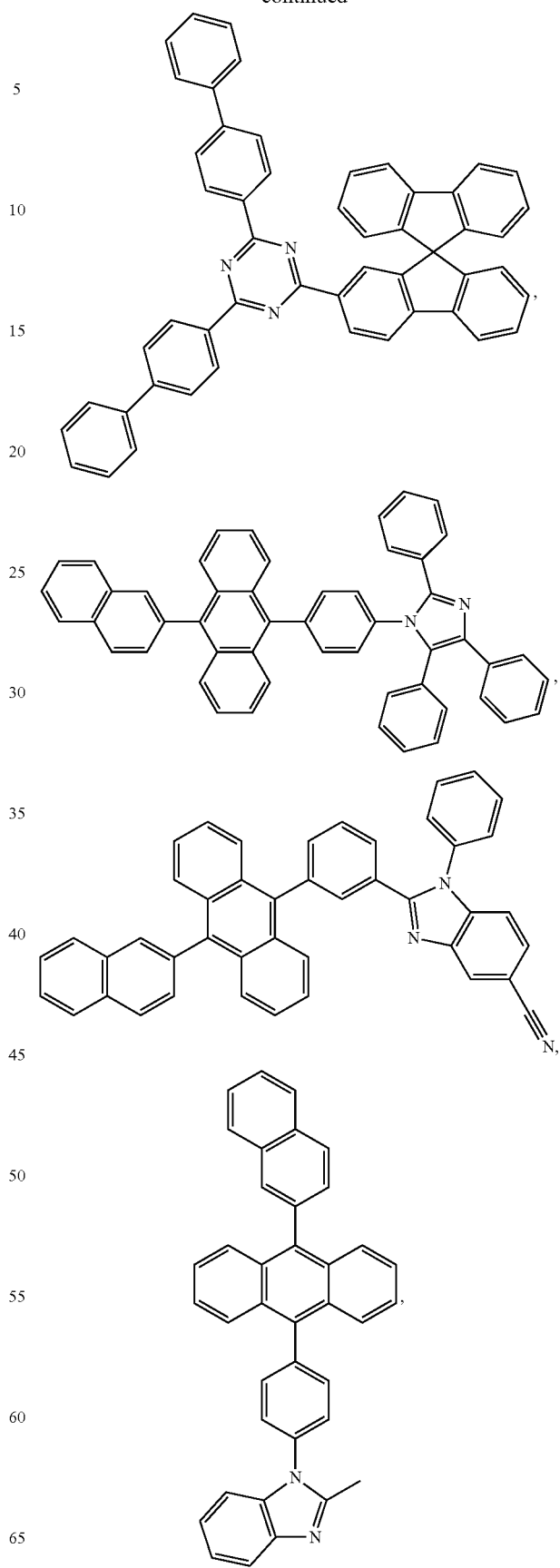

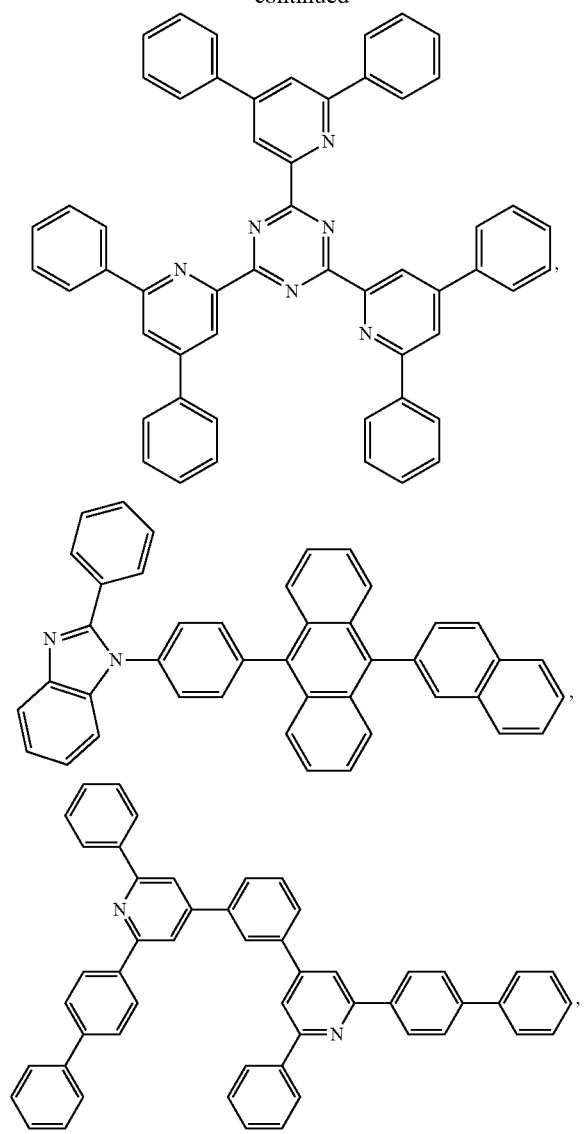

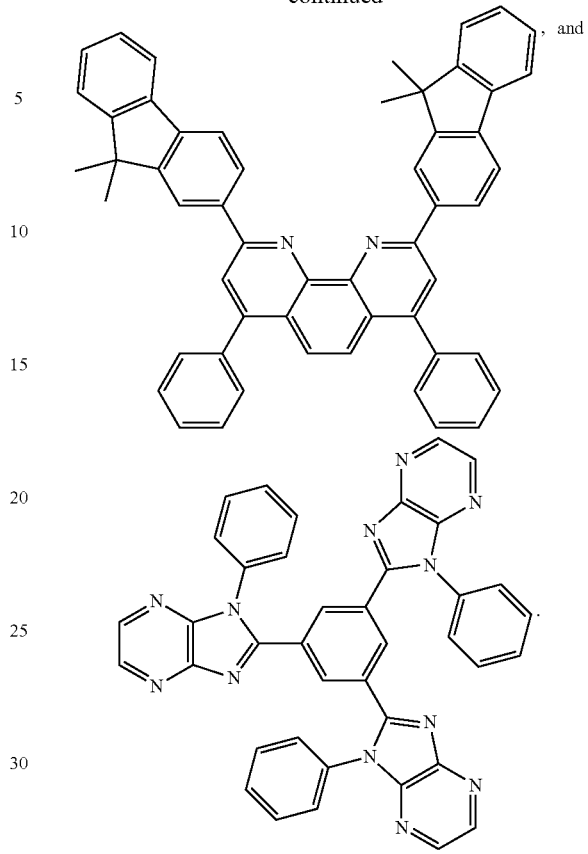

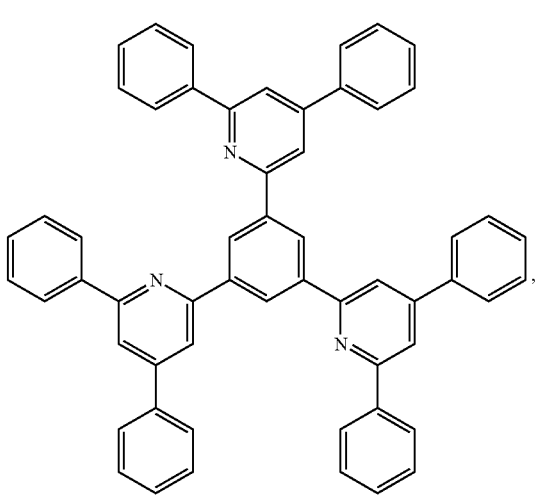

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Janus-Type Carbenes for Luminescent Two-Coordinated Metal Complexes

Figure 3:
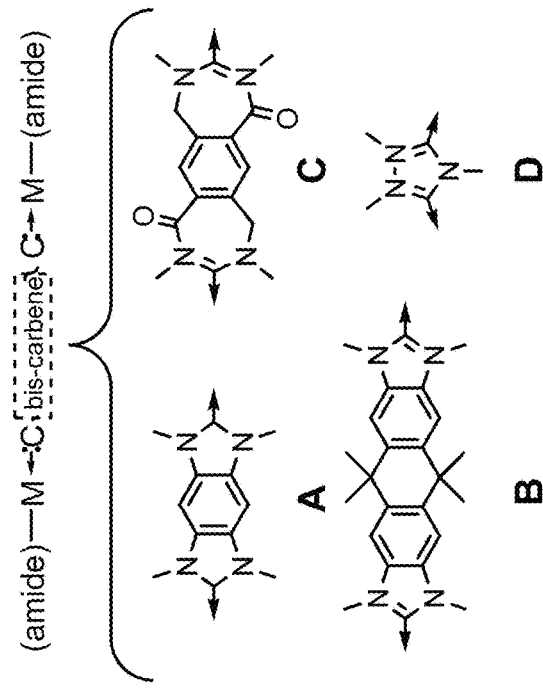
FIG. 3 depicts exemplary compounds of the invention, including a schematic illustration of Janus-type carbene phosphors using bis-carbene acceptors and examples of bis-carbene ligands.
Figure 4:
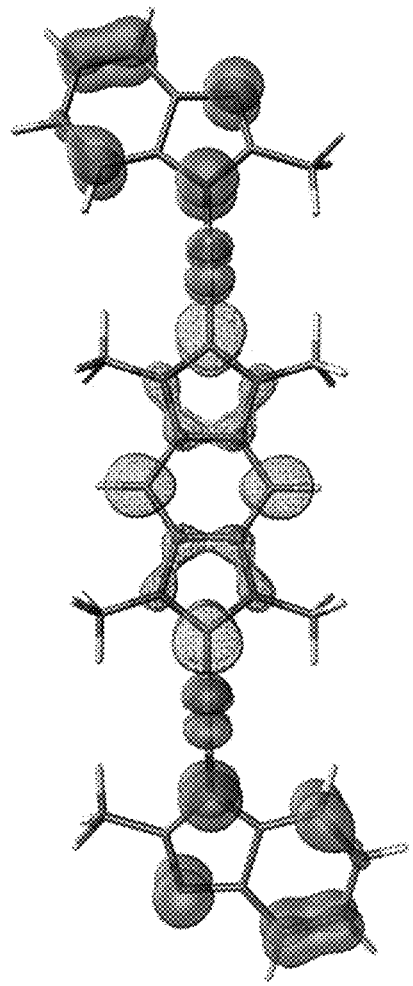
FIG. 4 depicts HOMO-LUMO contours for an exemplary bimetallic two-coordinated Cu complex (HOMO=solid, LUMO=mesh).

Bimetallic derivatives of the two-coordinated complexes using Janus-type bis-carbenes can be used to increase radiative rates for emission. Examples of these types of ditopic ligands are shown in FIG. 3. In this invention the central ligand is a bis-carbene ligand, bound to two metal(amide) moieties. The basic mononuclear (carbene)M(amide) structure, where M=Cu, Ag and Au, has been the subject of several disclosures and filed patents. The basic ligand structures for the amide functionality are meant to include those that have already been described in the (carbene)M(amide) disclosures and patents. The ditopic ligand D represents a means to decrease the emission lifetime form a bimetallic complex. The amide moiety could also be a hydrocarbon (aryl and substituted aryl, such as 4-dialkylamino-phenyl, an alkoxide, a sulfide or a phosphide). The choice of biscarbene and monoanionic ligand will determine the excited state energy and thus the emission color. The co-linear (A-C) or near co-linear (D) arrangement of CT donor-acceptor moieties will lead to strong intramolecular dipole-dipole coupling. Simple exciton theory predicts the transition dipoles in such a donor-acceptor-donor motif will undergo Davydov splitting into energetically higher (forbidden) and lower (allowed) transitions, where the latter transition will have a 2-4-fold higher oscillator strength than the mononuclear complex. The splitting of singlet energy levels into higher and lower energies, along with a similar splitting for the triplet states, will also lead to an overall decrease in $\Delta E_{ST}$. The combined effects of a decrease in $\Delta E_{ST}$ and increase in oscillator strength for the singlet state will increase radiative decay rates for dinuclear complexes relative to their mononuclear counterparts (Schinabeck, et al., Chem. Mater. 2019, 31 (12), 4392-4404). The combined effects of a smaller $\Delta E_{ST}$ and faster singlet should push radiative lifetimes to 100 ns or below for Cu, Ag and Au complexes. For example, a six-fold increase in the radiative decay rate for CAACMCz would give emission lifetimes in the 100-200 ns regime for Ag and Au based emitters. One drawback to ligands A and D is a decrease in their LUMO energies necessitating the use of electron deficient donor groups such as 1-benzimidazolyl to achieve blue emission (FIG. 1—bottom). However, the LUMO energies for ligands B and C are similar to their monomers allowing for a greater range of donor ligands. Clearly, the use of tailored donors (1.) and macrocycles to control stability (2.) and structure (3.) can be used to compliment the positive role of the Janus-type carbenes.

Figure 5:
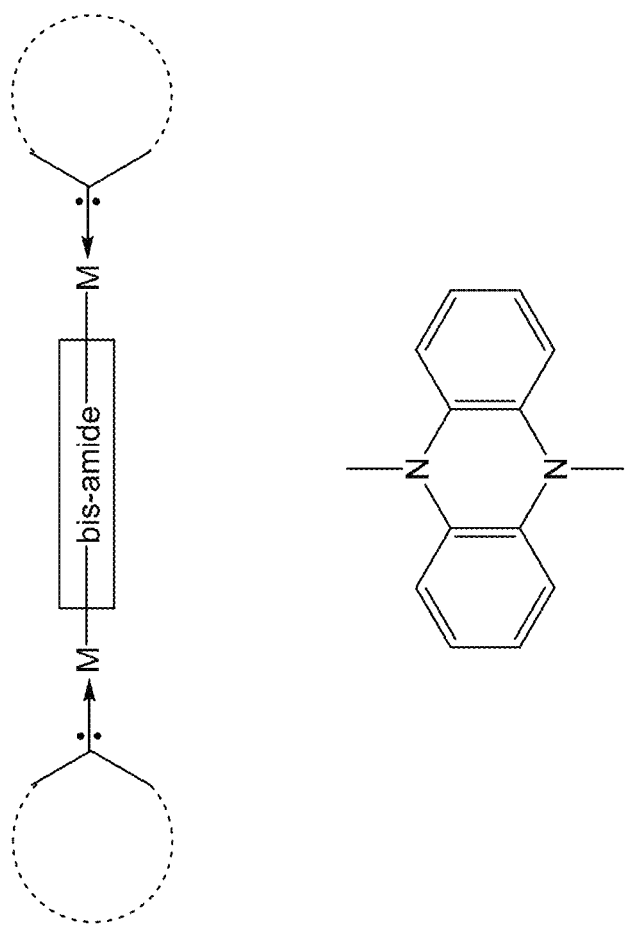
FIG. 5 depicts exemplary compounds of the invention, including a schematic illustration of Janus-type carbene phosphors with using a bis-amide donor and the bis-amide 5,10-dihydrophenazine.

The same principle can be applied to bimetallic complexes using Janus-type bis-amide donors and carbene acceptors. An example of such a bis-amide is 5,10-dihydrophenazine (FIG. 5). These complexes will undergo the same dipole-dipole interactions as described above for the bis-carbenes and thus will similarly display accelerated radiative rates for emission. The ligand be may be symmetric, i.e. the two N-atom donors may be isoelectronic and that nitrogens can be deprotonated to form a dianionic, ditopic ligand.

Figure 6:
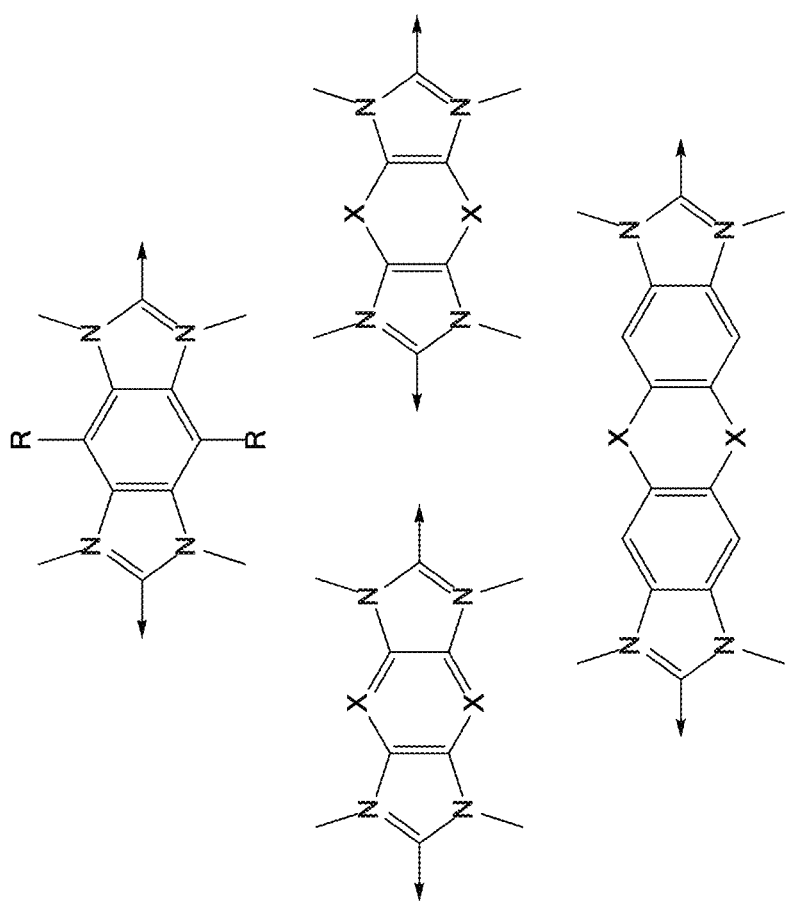
FIG. 6 depicts exemplary bridging structures for bis-carbenes. R=alkyl, aryl, alkoxy, etc. X=O, S, $CR_2$, NR, etc.

Generic depictions of bridging structures for the bis-carbenes are shown in FIG. 6.

Other examples of bridging structures for the bis-carbenes are shown in FIG. 7. Derivatives like these (where R=n-butyl, R'=tert-butyl) have been prepared (Prades, et al. Organometallics 2012, 31 (12), 4623-4626; Gonell, et al. Chemistry—a European Journal 2014, 20 (31), 9716-9724). The same concept will also work, albeit less effectively, with tris-carbene derivatives, examples of which are show in FIG. 8 (Ibanez, et al., Chemical Communications 2017, 53 (26), 3733-3736).

Figure 9:
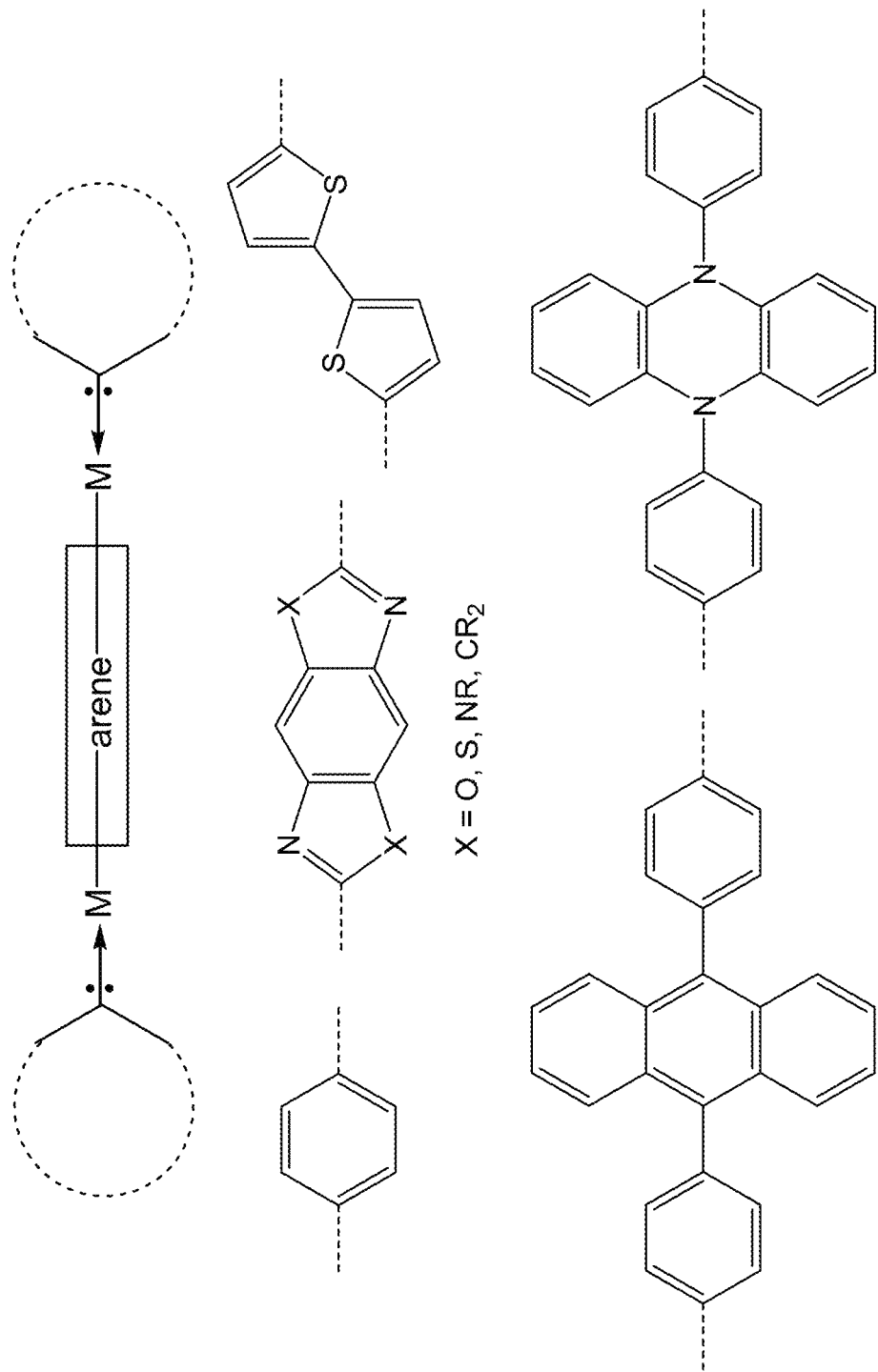
FIG. 9 is a schematic illustration of a Janus-type carbene phosphor using an arene donor with exemplary arene donors.

The same principle can be applied to bimetallic complexes using Janus-type arene donors and carbene acceptors. Examples of such arene donors are shown in FIG. 9. These complexes will undergo the same dipole-dipole interactions as described above for the bis-carbenes and thus will similarly display accelerated radiative rates for emission. In this case all of the carbenes listed in previous disclosures and patent filings are meant to be included and the arene can have a large range of structures, with the only requirements being that the ligand be symmetric, i.e. both C-atom donors are isoelectronic and that the carbons can be deprotonated to form a dianionic, ditopic ligand.

Several bimetallic copper complexes have been prepared using amide donors related to the example shown in FIG. 5, along with a bimetallic gold complex with a biphenyl donor.

Example 1: iCz(Cu-IPr)$_2$:

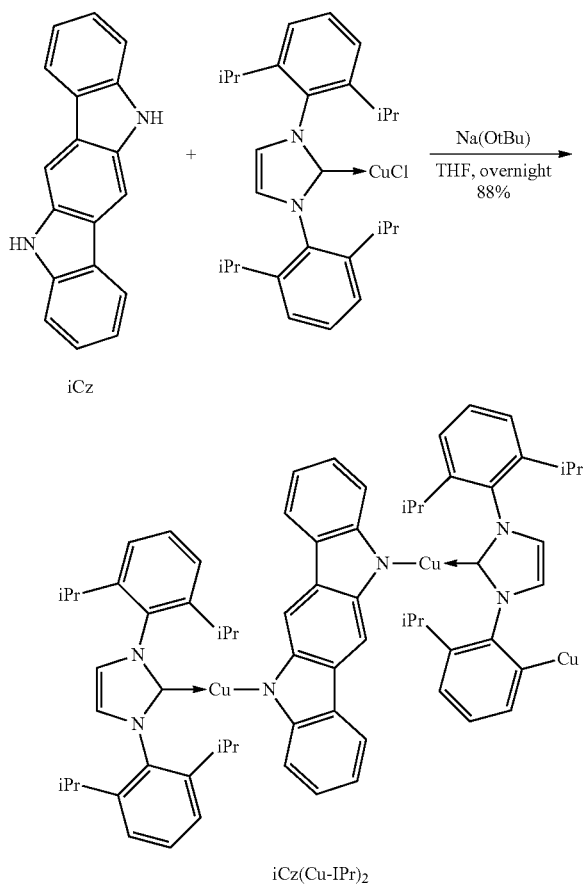

Under a dry nitrogen atmosphere, sodium tert-butoxide (11.3 mg, 117.1 µmol) was added in a 50-mL Schlenk flask containing dry THF (7 mL) solution of indolocarbazole (15 mg, 58.52 µmol). The green-yellowish emissive mixture was stirred at rt for one hour before the addition of IPrCuCl (57 mg, 117 µmol) and the stirring was continued overnight. The solution was filtered through a plug of celite and volatiles were removed under reduced pressures (Schlenk line vacuum). The residue was copiously washed with pentane to yield a yellow solid (60 mg, 88% yield).

Figure 10:
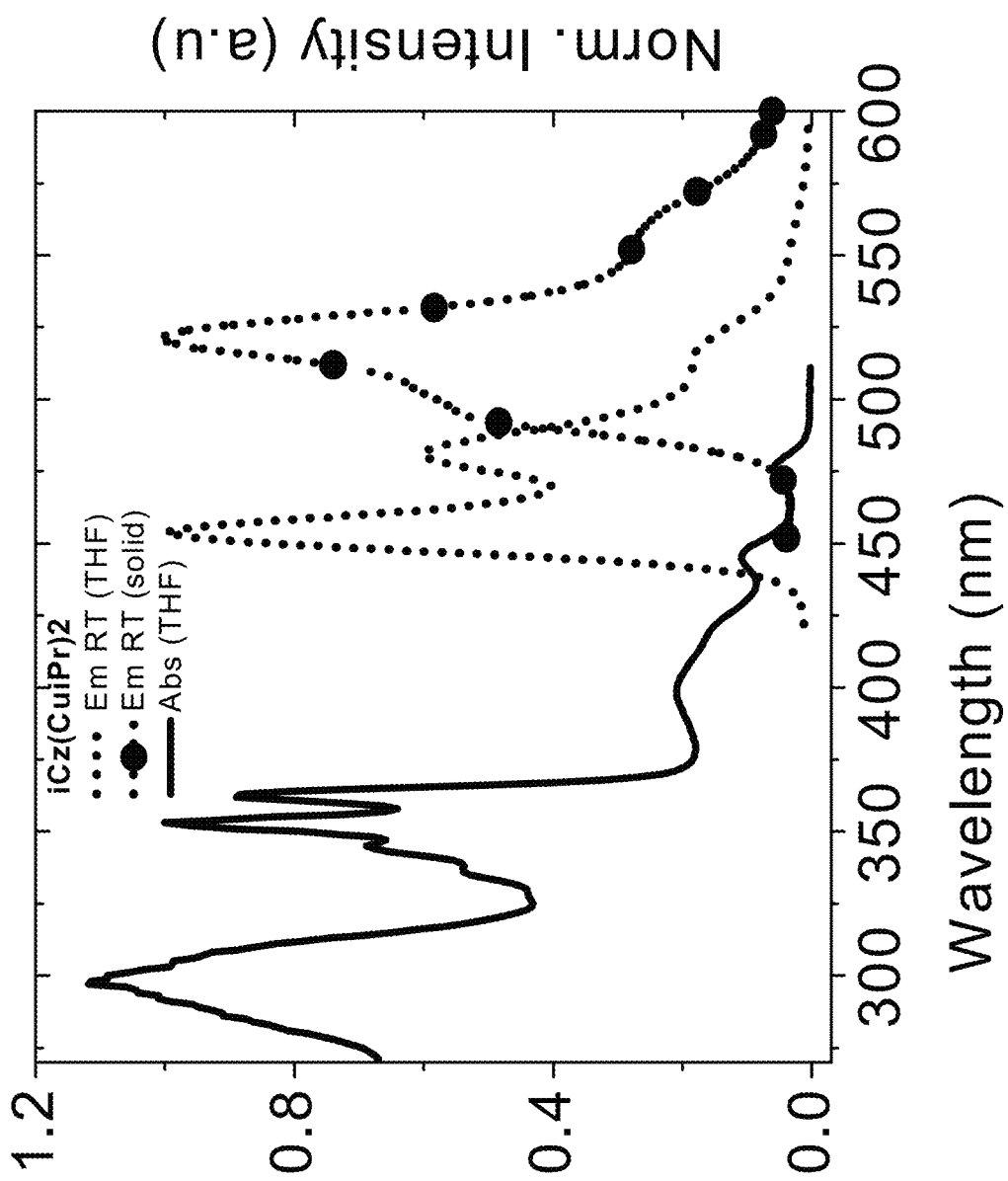
FIG. 10 is a plot of the absorption and emission spectra for $iCz(Cu-IPr)_2$.

This complex has an indolocarbazolyl (iCz) donor and N,N-(1,3-diisopropylphenyl)imidazolyl (IPr) carbene acceptor bridged with Cu atoms [iCz(Cu-IPr)$_2$]. The absorption and luminescence spectra for the iCz(Cu-IPr)$_2$ complex in tetrahydrofuran (THF) solution and emission as a neat solid are shown in FIG. 10; the emission properties in the solid state are given in Table 1 along with those for the mononuclear carbazolyl (Cz) analog CzCu-IPr.

TABLE 1

Emission properties of iCz(Cu-IPR)$_2$ and CzCu-IPr.

|  | Φ | τ (μs) | $k_r$ ($s^{-1}$) | $k_{nr}$ ($s^{-1}$) |
| --- | --- | --- | --- | --- |
| CzCu-IPr (solid) | 0.34 | 26 | $1.3 \times 10^7$ | $2.5 \times 10^7$ |
| iCz(Cu-IPr)$_2$ (solid) | 0.09 | 3.2 ns (29%), 9.3 ns (71%) | $1.2 \times 10^7$ | $1.2 \times 10^8$ |

The luminescence lifetimes and radiative rate constant ($k_r$) for iCz(Cu-IPr)$_2$ are consistent with fluorescence. The luminescence properties for this particular derivative do not appear to indicate any enhancement in the radiative rate constant caused by dipole-dipole coupling relative to the mononuclear derivative (CzCu-IPr). The IPr carbene is not a strong enough electron acceptor, and the charge transfer transitions needed to enhance the radiative decay rate lie at energies greater than the lowest excited state localized on the iCz donor moiety.

Example 2: bCz(Cu-IPr)$_2$

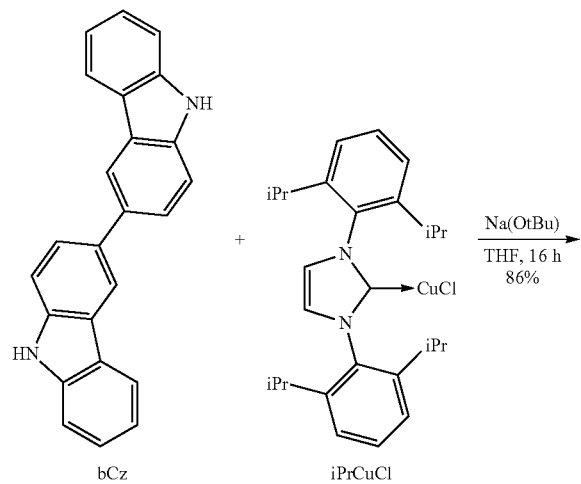

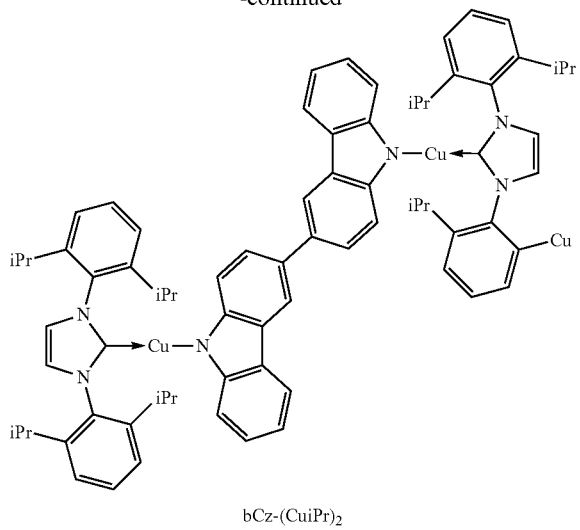

bCz-(CuiPr)$_2$

Under a dry nitrogen atmosphere, 1.5 mL of Na(OtBu) (0.1 M in THF, 154.2 μmol) was injected in a 50-mL Schlenk flask containing 10 mL THF solution of 3,3'-bicarbazole (25 mg, 75.2 μmol). The resulting yellow-emissive mixture was stirred at rt for 30 minutes before adding IPrCuCl (75.0 mg, 154.2 μmol). After 16 hours of continuous stirring, the mixture was filtered through a pad of celite and the solvents were removed under reduced pressure on a Schlenk line. The residue was redissolved in a minimum amount of dry dichloromethane, and 15 mL of pentane was added to precipitate out a white solid, which was collected by vacuum filtration to give 80 mg (86%) of the white solid. $^1$H NMR (400 MHz, Acetone-d6) δ=8.06 (dd, J=1.9, 0.7 Hz, 2H), 7.88 (m, 5H), 7.74 (t, 4H), 7.57 (d, J=7.8 Hz, 8H), 7.23 (dd, J=8.4, 1.9 Hz, 2H), 6.86 (ddd, J=8.2, 6.9, 1.3 Hz, 2H), 6.75 (ddd, J=7.8, 6.9, 1.0 Hz, 2H), 6.39 (dd, J=8.4, 0.6 Hz, 2H), 6.33 (dd, J=8.1, 0.9 Hz, 2H), 2.84 (hept, 8H), 1.32 (dd, J=6.9, 3.8 Hz, 49H).

Figure 11:
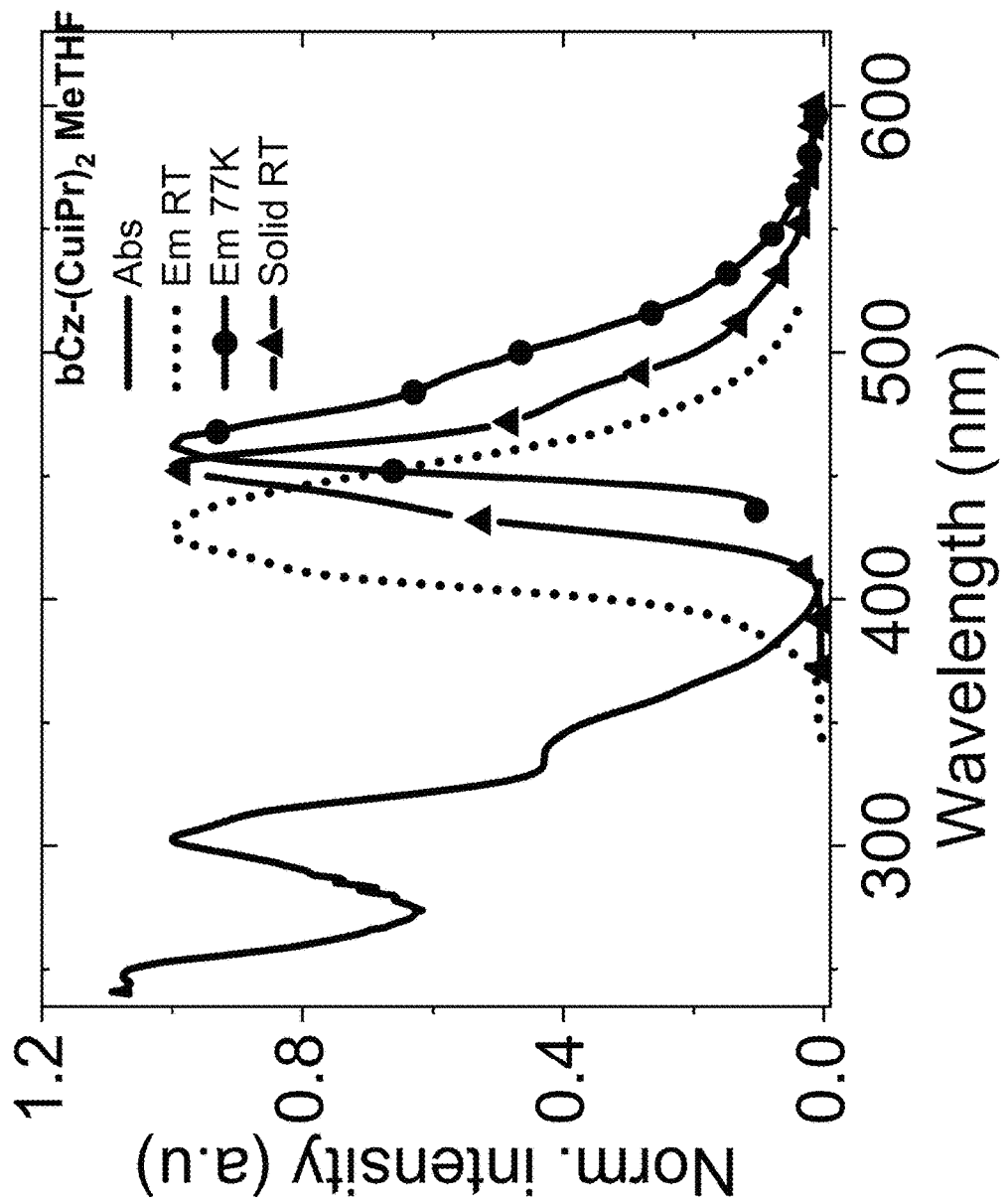
FIG. 11 is a plot of the absorption and emission spectra for bCz(Cu-IPr).

This complex has a 4,4'-bicarbazolyl (bCz) donor and N,N-(1,3-diisopropylphenyl)imidazolyl (IPr) carbene acceptor bridged with Cu atoms [bCz(Cu-IPr)$_2$]. The absorption and luminescence spectra for the bCz(Cu-IPr)$_2$ complex in methyltetrahydrofuran (MeTHF) solution and emission as a neat solid are shown in FIG. 11; the emission properties in the solid state are given in Table 2 along with those for the mononuclear carbazolyl (Cz) analog CzCu-IPr.

TABLE 2

Emission properties of bCz(Cu-IPr)$_2$ and CzCu-IPr.

|  | Φ | τ (μs) | $k_r$ ($s^{-1}$) | $k_{nr}$ ($s^{-1}$) |
| --- | --- | --- | --- | --- |
| CzCu-IPr (solid) | 0.34 | 26 | $1.3 \times 10^7$ | $2.5 \times 10^8$ |
| bCz(Cu-IPr)$_2$ (solid) | 0.08 | 1.8 | $4.4 \times 10^7$ | $5.1 \times 10^8$ |

The luminescence lifetimes and radiative rate constant ($k_r$) for bCz(Cu-IPr)$_2$ are consistent with fluorescence. The luminescence properties for this particular derivative show an enhancement in the radiative rate constant caused by dipole-dipole coupling relative to the mononuclear derivative (CzCu-IPr). The IPr carbene is a strong enough electron acceptor to provide charge transfer transitions needed to enhance the radiative decay rate.

Example 3: bCz(Cu-MAC)$_2$

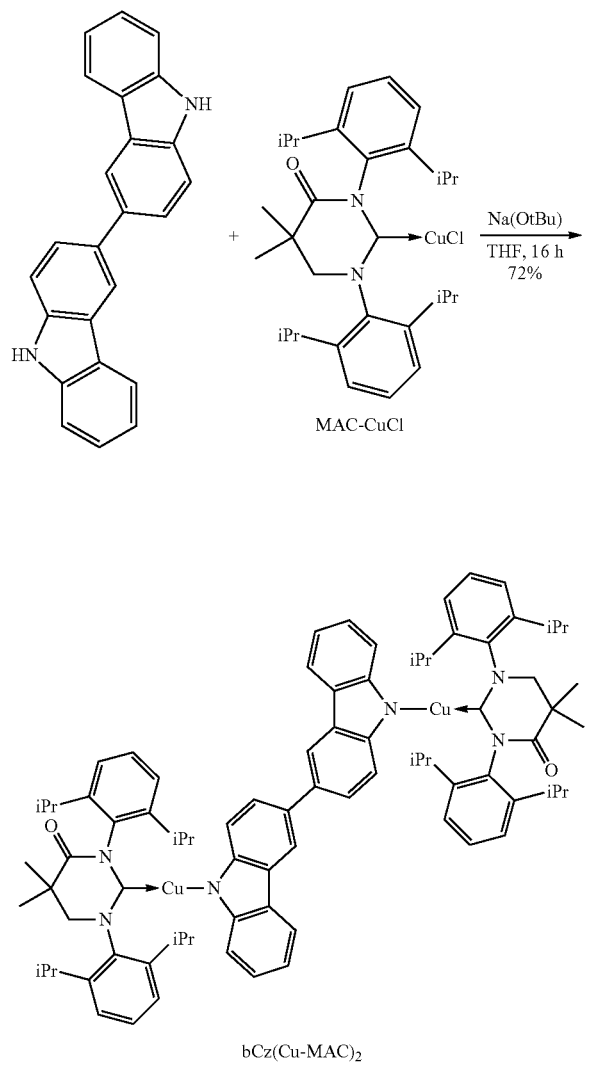

TABLE 3

Emission properties for bCz(Cu-MAC)$_2$ and CzCu-MAC

| | Φ | τ (μs) | k$_r$ (s$^{-1}$) | k$_{nr}$ (s$^{-1}$) |
|---|---|---|---|---|
| CzCu-MAC (MeTHF) | 0.55 | 1.1 | 5.0 × 10$^5$ | 4.1 × 10$^5$ |
| CzCu-MAC (solid) | 0.53 | 0.84 | 6.3 × 10$^5$ | 5.5 × 10$^4$ |
| bCz(Cu-MAC)$_2$ (MeTHF) | 0.03 | 0.032 | 9.4 × 10$^5$ | 3.0 × 10$^7$ |
| bCz(Cu-MAC)$_2$ (solid) | 0.08 | 0.056 | 1.4 × 10$^6$ | 1.6 × 10$^7$ |

The luminescence lifetimes and radiative rate constant (k$_r$) for bCz(Cu-MAC)$_2$ are consistent with phosphorescence. The luminescence properties for this particular derivative show an enhancement in the radiative rate constant caused by dipole-dipole coupling relative to the mononuclear derivative (CzCu-MAC). The MAC carbene is a strong enough electron acceptor to provide charge transfer transitions needed to enhance the radiative decay rate.

Example 4: DPPT(Cu-IPr)$_2$

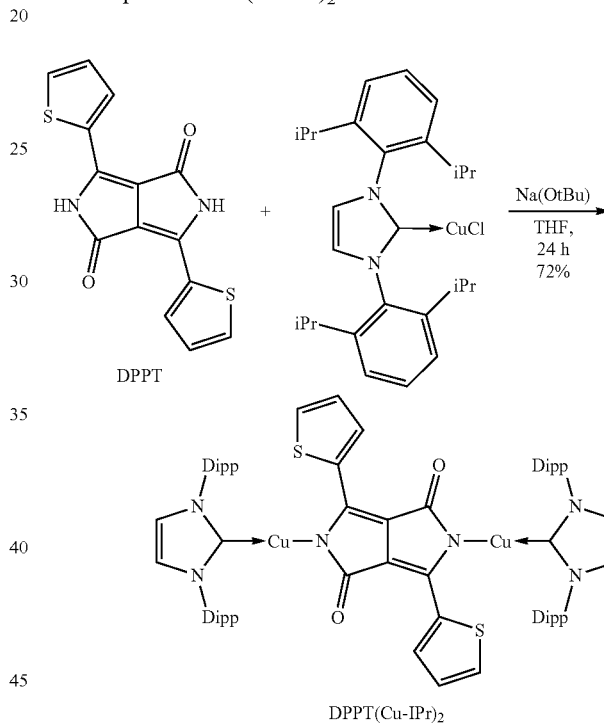

A 50-mL Schlenk flask under nitrogen atmosphere was charged with THF (10 mL), 3,3'-bicarbazole (25 mg, 75.2 μmol) and Na(OtBu) (15.2 mg, 158 μmol). The mixture was stirred at rt for 30 minutes before adding MAC-CuCl (87 mg, 155.7 μmol). After 16 hours of continuous stirring, the solution was filtered through a plug of celite and volatiles were removed under reduced pressure. A minimum amount of dry dichloromethane was added to the residue to make a concentrate solution. After adding 20 mL of dry hexane, a precipitate developed, and was collect by vacuum filtration, washed with more hexane, and dried under vacuum to yield a dark purple solid (79 mg, 72% yield).

Figure 12:
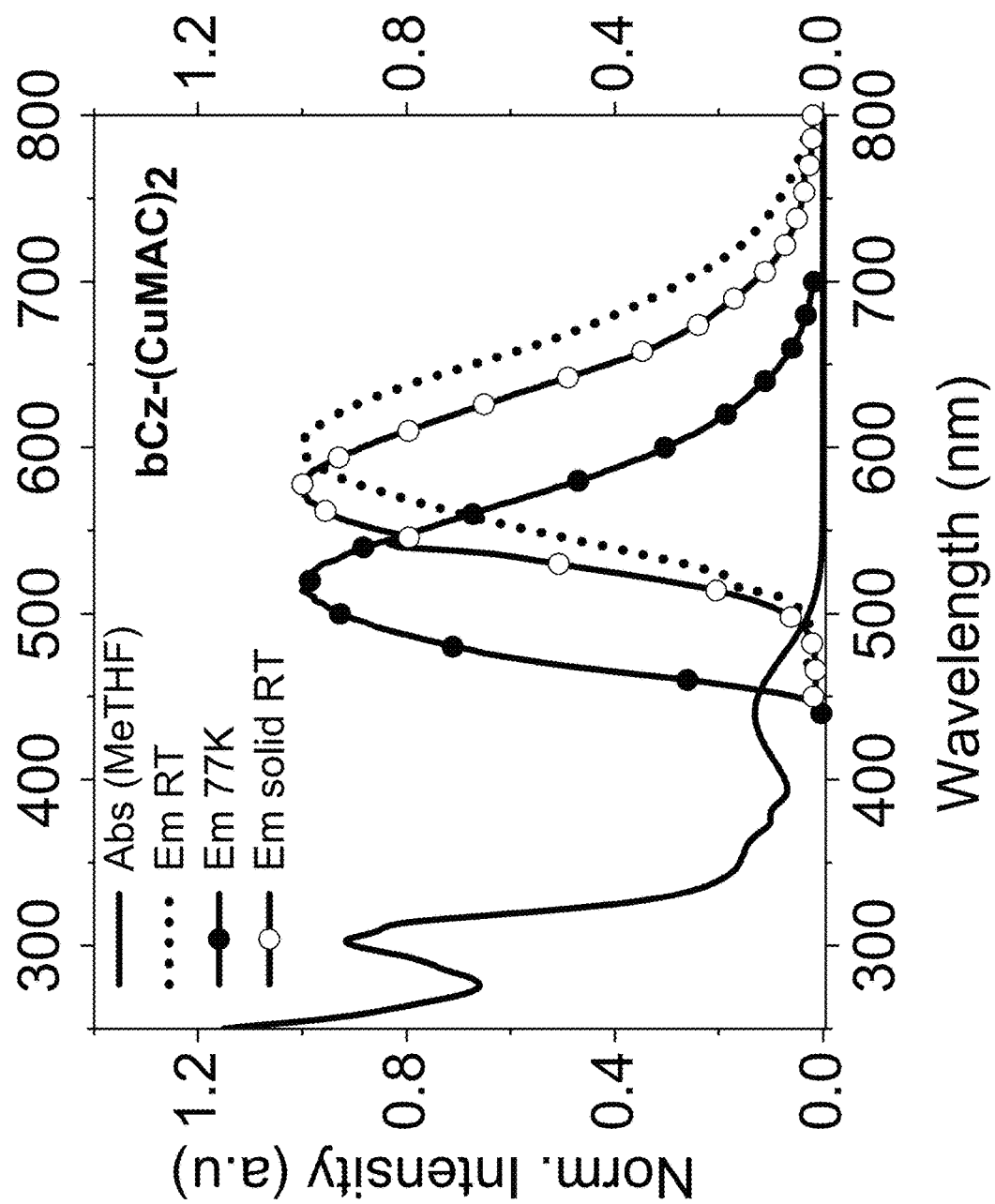
FIG. 12 is a plot of the absorption and emission spectra for $bCz(Cu-MAC)_2$.

This complex has a 4,4'-bicarbazolyl (bCz) donor and N,N'-bis(diisopropylphenyl)-5,5-dimethyl-4-keto-tetrahydropyr-imidin-2-ylidene) (MAC) carbene acceptor bridged with Cu atoms [bCz(Cu-MAC)$_2$]. The absorption and luminescence spectra for the bCz(Cu-MAC)$_2$ complex in methyltetrahydrofuran (MeTHF) solution and emission as a neat solid are shown in FIG. 12; the emission properties in the solid state are given in Table 3 along with those for the mononuclear carbazolyl (Cz) analog CzCu-MAC.

Under nitrogen atmosphere, a 100-mL Schlenk flask was charged with THF (25 mL), diketopyrrolopyrrole (50 mg, 166.47 μmol) and sodium tert-butoxide (37.4 mg, 332.9 μmol) and then stirred at rt for 30 minutes. IPrCuCl (167.2 mg, 342.9 μmol) was then added and the reaction was continued overnight 24 hours. After the completion of the reaction, the solution was filtered through a plug of celite and the filtrate volatiles were removed under reduced pressure. The crude solid was dissolved a minimum amount of dichloromethane, and the precipitate was encouraged by adding 20 mL of hexane. The vacuum filtration and drying of the precipitate yielded 144 mg (72%). $^1$H NMR (400 MHz, acetone-d6) δ=8.48 (dd, J=3.5, 1.4 Hz, 2H), 7.68 (s, 4H), 7.49 (t, J=7.7 Hz, 4H), 7.35 (d, J=7.8 Hz, 8H), 6.89 (m, 4H), 2.77 (hept, 8H), 1.28 (d, J=6.9 Hz, 12H), 1.21 (d, J=6.9 Hz, 12H).

This complex has a diketopyrrolopyrrole-dithiophene amide (DPPT) donor and N,N-(1,3-diisopropylphenyl)imidazolyl (IPr) carbene acceptor bridged with Cu atoms

Figure 13:
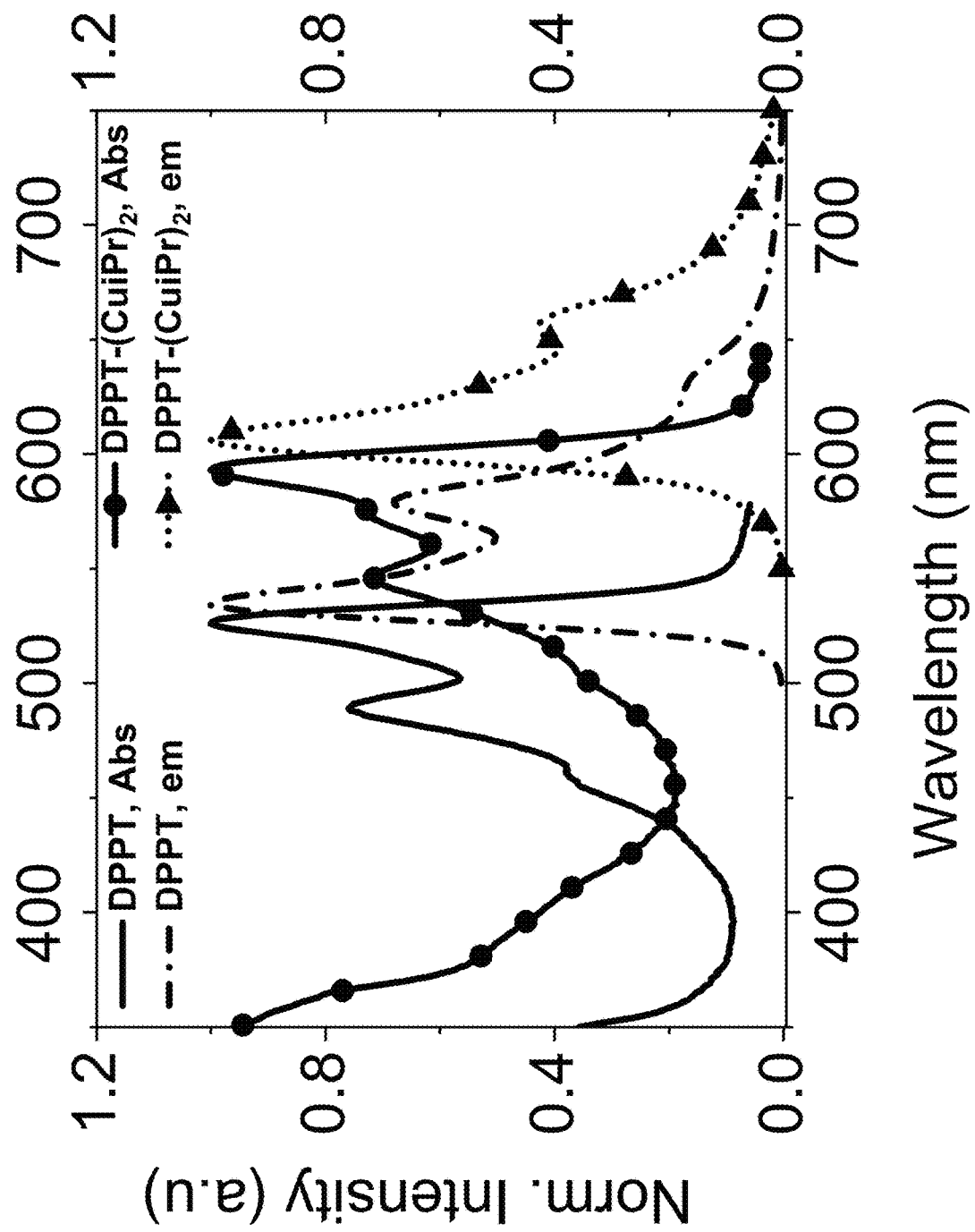
FIG. 13 is a plot of the absorption and emission spectra for DPPT and $DPPT(Cu-IPr)_2$.

[DPPT(Cu-IPr)$_2$]. The absorption and luminescence spectra for the DPPT(Cu-IPr)$_2$ complex and DPPT in methyltetrahydrofuran (MeTHF) solution are shown in FIG. 13; the emission properties in MeTHF solution are given in Table 4.

TABLE 4

Emission properties for [DPPT(Cu-IPr)$_2$]

| | Φ | τ (μs) | k$_r$ (s$^{-1}$) | k$_{nr}$ (s$^{-1}$) |
|---|---|---|---|---|
| DPPT(Cu-IPr)$_2$ | 0.45 | 0.006 | 7.5 × 10$^7$ | 9.2 × 10$^7$ |

The luminescence lifetimes and radiative rate constant (k$_r$) for DPPT(Cu-IPr)$_2$ are consistent with fluorescence. The luminescence properties for this particular derivative do not indicate any enhancement in the radiative rate constant caused by dipole-dipole coupling. The IPr carbene is not a strong enough electron acceptor and the charge transfer transitions needed to enhance the radiative decay rate lie at energies greater than the lowest excited state localized on the DPPT donor moiety.

Example 5: Bimetallic (MAC)Au(4,4'-biphenyl)Au (MAC) Complexes

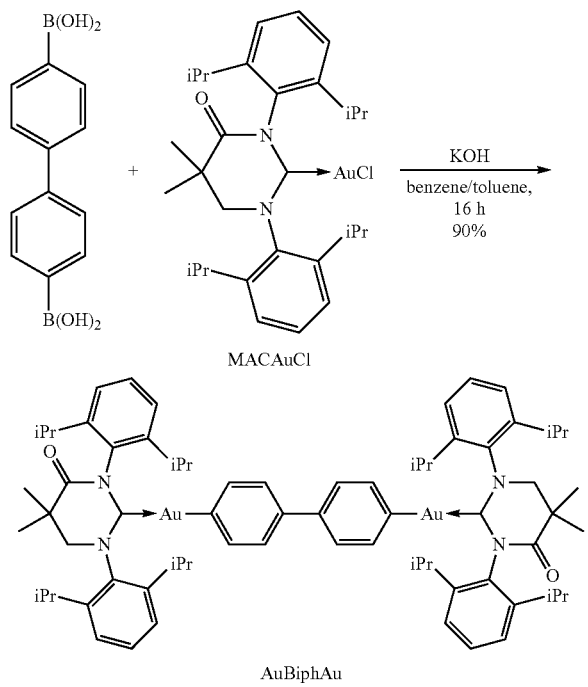

The (MAC)AuCl (100 mg), 4,4'-biphenyldiboronic acid (0.5 equiv.) and KOH (2 equiv.) are inserted in an oven dried dram vial. The system is evacuated and refilled three times with N$_2$. A mixture of toluene and benzene (2 ml, 1:1 v/v) is injected and the suspension is stirred at room temperature overnight. The suspension is filtered through a pad of Celite to obtain a clear filtrate. Excess amount of pentane is added, providing the desired product as white crystalline powder. The final product is purified by recrystallization using CH$_2$Cl$_2$ and pentane.

(MAC)Au(Biphenyl)Au(MAC) (AuBiphAu): white crystalline powder, 96 mg, yield 90%. $^1$H NMR (400 MHz, CDCl$_3$) δ 7.41 (t, J=7.7 Hz, 4H), 7.26-7.21 (m, 8H), 6.97 (t, J=8.9 Hz, 4H), 6.57 (d, J=8.1 Hz, 4H), 3.71 (s, 4H), 3.19 (dq, J=13.8, 6.9 Hz, 4H), 3.02-2.89 (m, 4H), 1.54 (s, 12H), 1.42 (d, J=6.8 Hz, 12H), 1.37 (d, J=6.9 Hz, 12H), 1.33 (d, J=6.9 Hz, 12H), 1.18 (d, J=6.9 Hz, 12H). $^{13}$C NMR (101 MHz, CDCl$_3$) δ 222.61, 171.81, 164.62, 145.24, 144.26, 140.15, 139.74, 138.40, 135.27, 129.72, 129.54, 124.92, 124.90, 123.97, 77.20, 61.98, 37.87, 29.12, 28.67, 24.69, 24.64, 24.24, 23.78.

Figure 14:
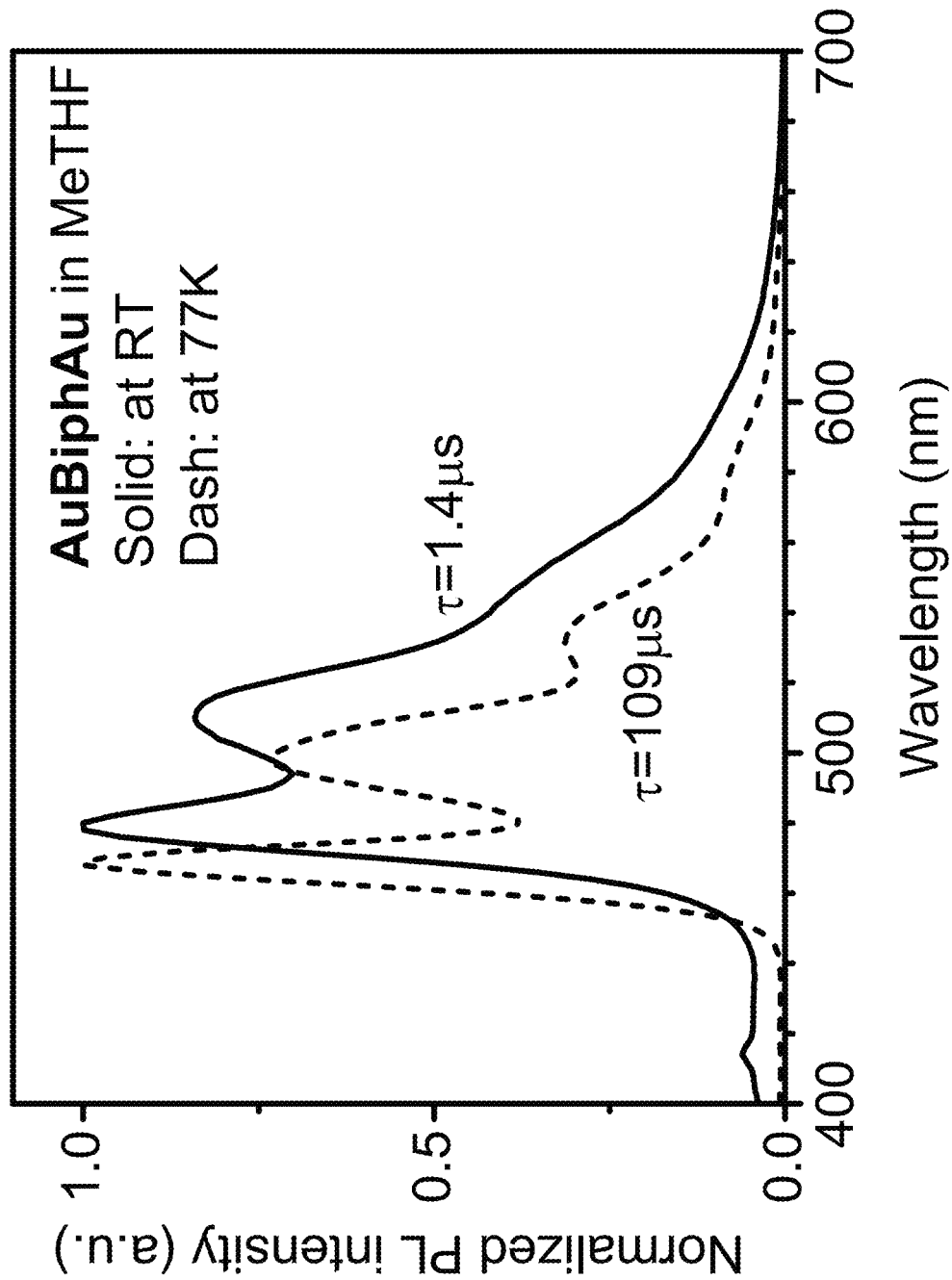
FIG. 14 is a plot of the emission spectra of AuBiphAu in methyltetrahydrofuran (MeTHF) solution.
Figure 15:
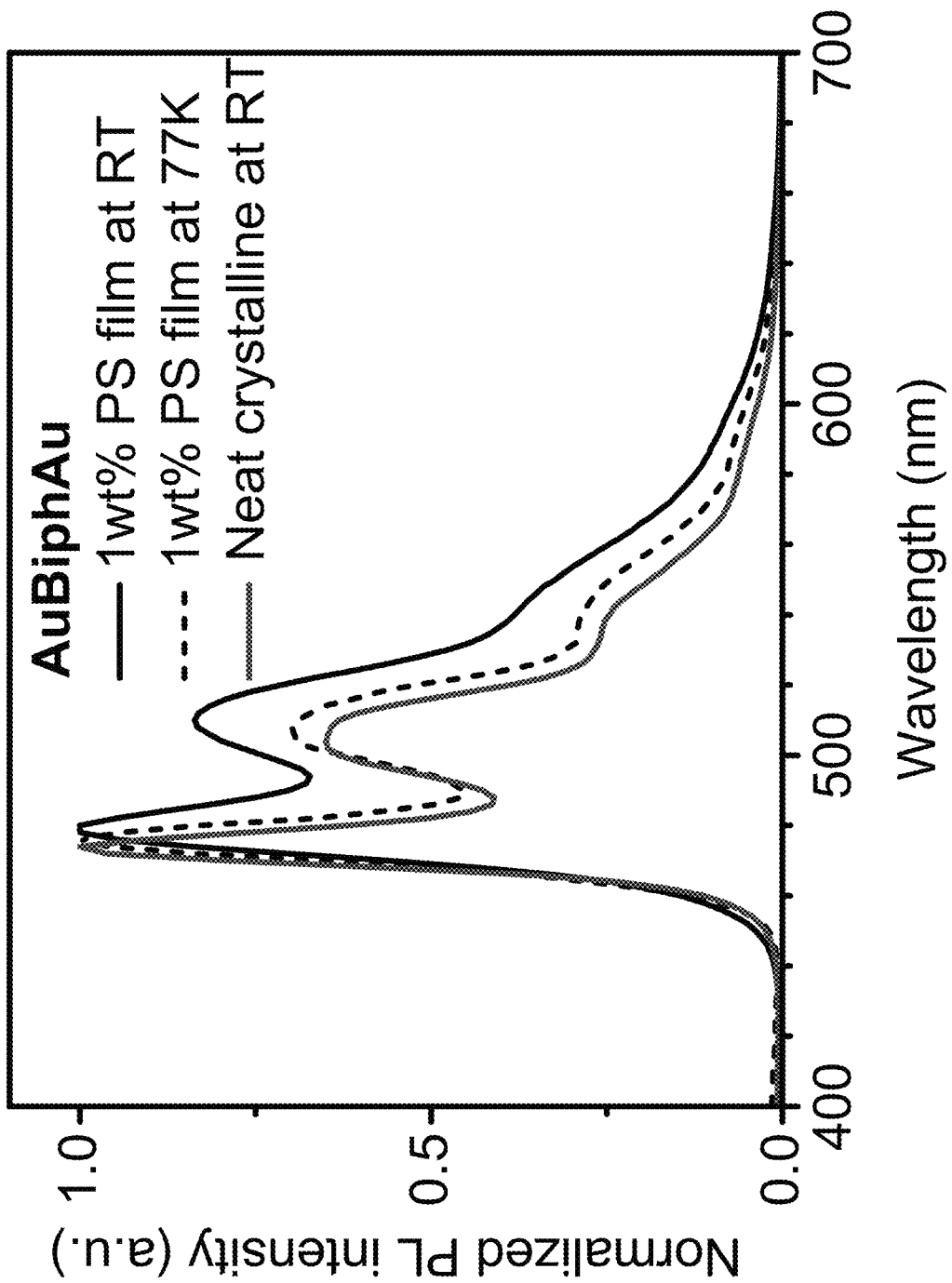
FIG. 15 is a plot of the emission spectra of AuBiphAu in polystyrene (PS) film and neat solid.
Figure 16:
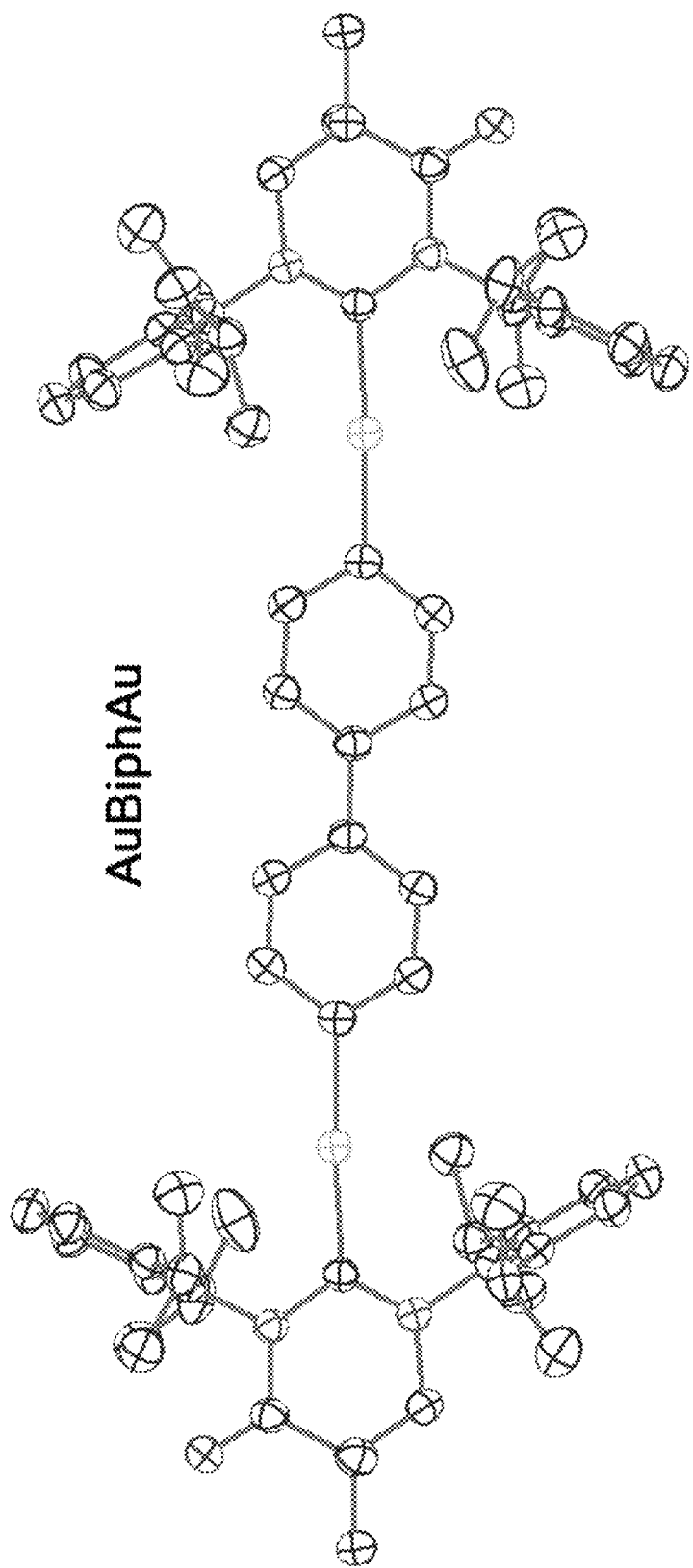
FIG. 16 is an X-ray crystal structure of AuBiphAu.

This complex has a 4,4'-biphenyl (Biph) donor and N,N'-bis(diisopropylphenyl)-5,5-dimethyl-4-keto-tetrahydropyrimidin-2-ylidene) (MAC) carbene acceptor bridged with Au atoms (AuBiphAu). The luminescence spectra for the AuBiphAu complex methyltetrahydrofuran (MeTHF) solution is shown in FIG. 14, and the luminescence spectra in in polystyrene (PS) film and neat solid are shown in FIG. 15. An X-ray structure of AuBiphAu is shown in FIG. 16. The emission properties in the polystyrene (PS) film are given in Table 5 along with those for the mononuclear 4-biphenyl (Biph) analog AuBiph.

TABLE 5

Emission properties of AuBiphAu and AuBiph in 1 wt % doped PS film

| | λ$_{em}$ (nm) | Φ | τ (μs) | k$_r$ (s$^{-1}$) | k$_{nr}$ (s$^{-1}$) |
|---|---|---|---|---|---|
| AuBiph | 460, 490 | 0.048 | 43 | 1.1 × 10$^3$ | 22.1 × 10$^3$ |
| AuBiphAu | 480, 510 | 0.311 | 55 | 5.7 × 10$^3$ | 12.5 × 10$^3$ |

The luminescence lifetimes and radiative rate constant (k$_r$) for AuBiphAu are consistent with phosphorescence. The luminescence properties for this particular derivative show an enhancement in the radiative rate constant caused by dipole-dipole coupling relative to the mononuclear AuBiph complex. The MAC carbene is a strong enough electron acceptor to provide charge transfer transitions needed to enhance the radiative decay rate.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A compound of Formula III or Formula IV:

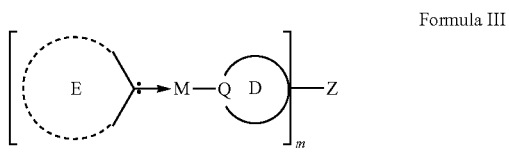

Formula III

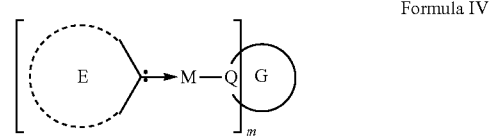

Formula IV wherein E is a carbene coordinated to metal M, wherein E has the structure:

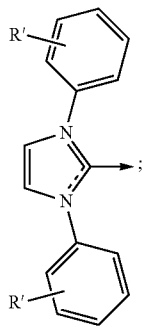

each E can be the same or different;

each ring D is independently a single or fused carbocyclic ring or heterocyclic ring, which may be saturated or unsaturated, which is bound covalently bound to Z, wherein each ring D may be the same or different, and wherein each ring D is independently substituted with R;

Z is a linking group selected from the group consisting of a single bond, aryl, heteroaryl, alkyl, O, S, NR, and combinations thereof;

m is 2, 3, or 4;

G is a single or fused heterocyclic ring, which may be saturated or unsaturated; which comprises m atoms Q; and which may be optionally substituted with one or more R, each occurrence of R and R' is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

each occurrence of Q is independently C or N; and

M is Au, Ag, or Cu.

2. The compound of claim 1, wherein the compound is a compound of Formula IIIa or Formula IVa Formula IIIa

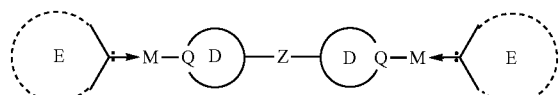

Formula IVa

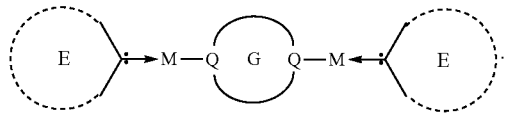

3. The compound of claim 1, wherein m is 2.

4. The compound of claim 1, wherein G is selected from the group consisting of

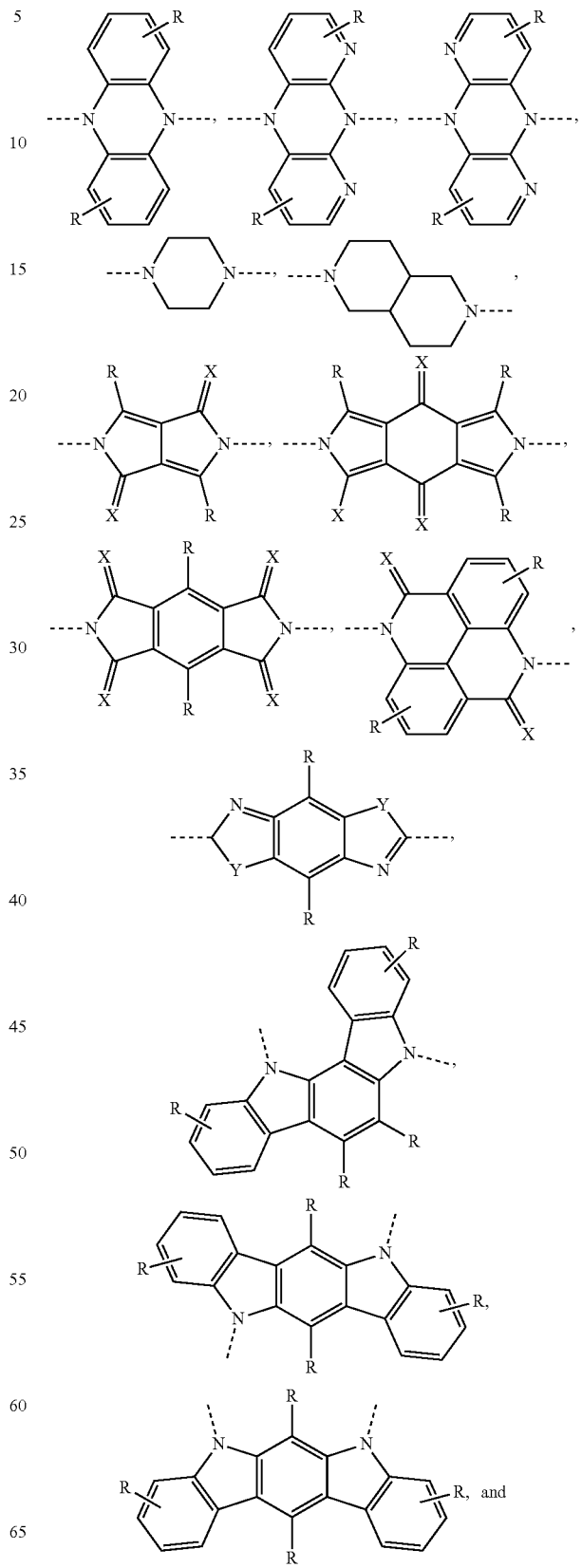

-continued

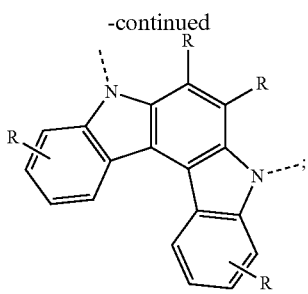

wherein dashed lines indicate coordination to the metal M;

X is O, S, or $C(R^6)_2$;

Y is O, S, or $C(R^6)_2$;

each occurrence of $R^6$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and two $R^6$ may optionally together form a ring.

5. The compound of claim 1, wherein each D is independently selected from the group consisting of phenyl, fluorene, naphthalene, triphenylene, dibenzothiophene, dibenzofuran, dibenzoselenophene, carbazole, indolocarbazole, imidazole, pyridine, triazine, and benzimidazole.

6. The compound of claim 2, wherein

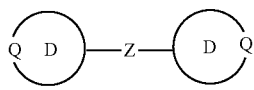

is represented by

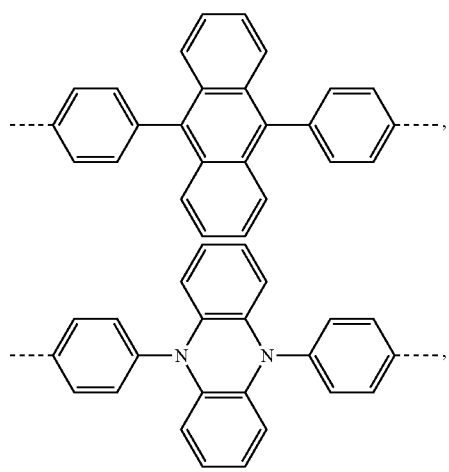

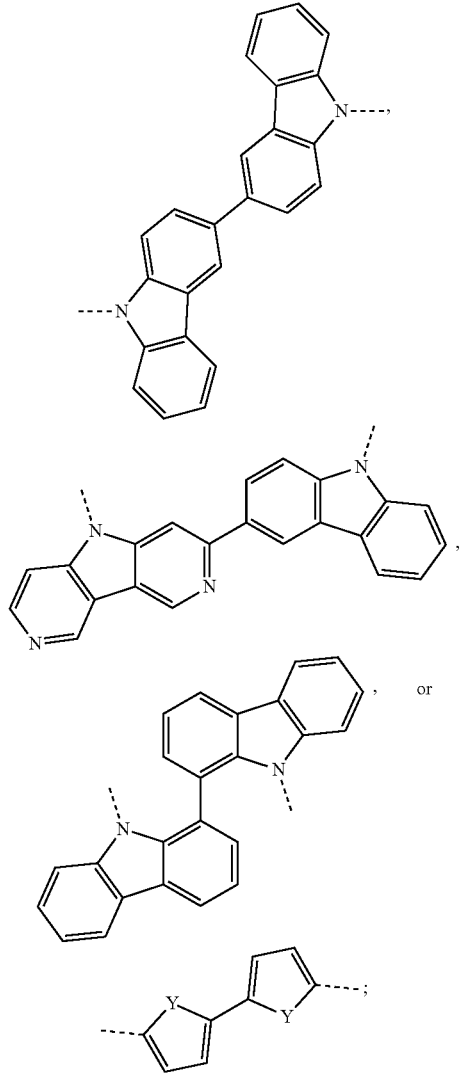

wherein arrows indicate coordination to the metal M;

Y is O, S, SO, $SO_2$, $NR^7$, or $C(R^7)_2$;

each occurrence of $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and two $R^7$ may optionally together form a ring.

7. An organic light emitting device (OLED) comprising:
an anode;
a cathode; and
an organic layer, disposed between the anode and the cathode, comprising a compound according to claim 1.

8. A formulation comprising the compound of claim 1.

* * * * *